US010052365B2

(12) United States Patent
Rincon et al.

(10) Patent No.: US 10,052,365 B2
(45) Date of Patent: Aug. 21, 2018

(54) METHODS AND PRODUCTS RELATING TO GSK3β REGULATION

(71) Applicant: University of Vermont and State Agricultural College, Burlington, VT (US)

(72) Inventors: Mercedes Rincon, Burlington, VT (US); Tina M. Thornton, Essex Junction, VT (US)

(73) Assignee: University of Vermont and State Agricultural College, Burlington, VT (US)

( * ) Notice: Subject to any disclaimer, the term of this patent is extended or adjusted under 35 U.S.C. 154(b) by 0 days.

(21) Appl. No.: 14/561,524

(22) Filed: Dec. 5, 2014

(65) Prior Publication Data

US 2015/0150950 A1 Jun. 4, 2015
US 2017/0151312 A9 Jun. 1, 2017

Related U.S. Application Data

(63) Continuation of application No. 13/887,679, filed on May 6, 2013, now abandoned, which is a continuation of application No. 12/989,901, filed as application No. PCT/US2009/002609 on Apr. 29, 2009, now Pat. No. 8,445,648.

(60) Provisional application No. 61/126,133, filed on Apr. 30, 2008.

(51) Int. Cl.

| | |
|---|---|
| ***A61K 38/45*** | (2006.01) |
| ***C12Q 1/48*** | (2006.01) |
| ***A61K 45/06*** | (2006.01) |
| ***C12N 9/12*** | (2006.01) |

(52) U.S. Cl.

CPC .............. *A61K 38/45* (2013.01); *A61K 45/06* (2013.01); *C12N 9/12* (2013.01); *C12Q 1/485* (2013.01); *C12Y 207/11026* (2013.01); *G01N 2333/91205* (2013.01); *G01N 2440/14* (2013.01); *G01N 2500/04* (2013.01); *G01N 2500/20* (2013.01)

(58) Field of Classification Search

None

See application file for complete search history.

(56) References Cited

U.S. PATENT DOCUMENTS

| | | | |
|---|---|---|---|
| 6,949,544 | B2 | 9/2005 | Bethiel et al. |
| 8,445,648 | B2 | 5/2013 | Rincon et al. |
| 2002/0098511 | A1 | 7/2002 | Heichman et al. |
| 2013/0224212 | A1 | 8/2013 | Rincon et al. |

FOREIGN PATENT DOCUMENTS

WO WO2009134370 A2 11/2009

OTHER PUBLICATIONS

Heitz et al., Twenty years of cell-penetrating peptides: from molecular mechanisms to therapeutics, 2009, British Journal of Pharmacology 157:195-206.*

Brancho, D. et al., "Mechanism of p38 MAP kinase activation in vivo", Genes & Development, Jun. 2003, vol. 17, pp. 1969-1978.

Buescher, J. et al., "A Noncatalytic Domain of Glycogen Synthase Kinase-3 (GSK-3) Is Essential for Activity", The Journal of Biological Chemistry, Mar. 2010, vol. 285, No. 11, pp. 7957-7963.

Cross, D. et al., "Inhibition of glycogen synthase kinase-3 by insulin mediated by protein kinase B", Nature, Dec. 1995, vol. 378. pp. 785-789.

Dajani, R. et al., "Crystal Structure of Glycogen Synthase Kinase 3B:Structural Basis for Phosphate-Primed Substrate Specificity and Autoinhibition", Cell, Jun. 2001, vol. 105, pp. 721-732.

Derijard B. et al., "JNK1: a protein kinase stimulated by UV light and Ha-Ras that binds and phosphorylates the c-Jun activation domain", Cell, Mar. 1994, vol. 76, pp. 1025-1037.

Diehl, N. et al., "Activation of the p38 Mitogen-activated Protein Kinase Pathway Arrests Cell Cycle Progression and Differentiation of Immature Thymocytes in Vivo", J. Exp. Med, Jan. 2000, vol. 191, No. 2, pp. 321-334.

Ding, Q. et al., "Erk Associates with and Primes GSK-3B for its Inactivation Resulting in Upregulation of B-Catenin", Molecular Cell, Jul. 2005, vol. 19, pp. 159-170.

Dmitrieva, N. et al., "Rapid activation of G2/M checkpoint after hypertonic stress in renal inner medullary epithelial cells is protective and requires p38 kinase", PNAS, Jan. 2002, vol. 99, No. 1, pp. 184-189.

Doble B. et al., "GSK-3: tricks of the trade fora multi-tasking kinase", Journal of Cell Science, 2003, vol. 116, pp. 1175-1186.

Doble, B. et al., "Functional Redundancy of GSK-3x and GSK-3β in Wnt/β-Catenin Signaling Shown by Using an Allelic Series of Embryonic Stem Cell Lines", Developmental Cell, Jun. 2007, vol. 12, pp. 957-971.

Farley, N. et al., "p38 Mitogen-Activated Protein Kinase Mediates the Fas-Induced Mitochondrial Death Pathway in CD8+ T Cells" Molecular and Cellular Biology, Mar. 2006, vol. 26, No. 6, pp. 2118-2129.

Filali, M. et al., "Wnt-3A/B-Catenin Signaling Induces Transcription from the LEF-1 Promoter", The Journal of Biological Chemistry, Sep. 2002, vol. 277, No. 36, pp. 33398-33410.

Frame S. et al., "GSK3 takes centre stage more than 20 years after its discovery", Biochem. J., 2001, vol. 359, pp. 1-16.

Genbank NCBI Submission; Accession No. NM_002093, submitted Apr. 20, 2008.

Genbank NCBI Submission; Accession No. NP_062801, submitted Apr. 29, 2008.

Genbank NCBI Submission; Accession No. NM_019827, submitted Apr. 29. 2008.

(Continued)

*Primary Examiner* — John D Ulm

(74) *Attorney, Agent, or Firm* — Pierce Atwood LLP

(57) ABSTRACT

The invention relates to methods and compositions for regulation of GSK3β activity. The invention provides phosphorylated GSK3β polypeptides and antibodies that recognize such polypeptides. The invention further includes methods for treating disorders that are associated with elevated or reduced GSK3β activity.

6 Claims, 16 Drawing Sheets

(56) References Cited

OTHER PUBLICATIONS

Gounari, F. et al., "Somatic activation of beta-catenin bypasses pre-TCR signaling and TCR selection in thymocyte development", Nature Immunology, Sep. 2001, vol. 2, No. 9, pp. 863-869.
He, T. et al., "The Identification of c-MYC as a Target of the APC Pathway", Science; Sep. 1998, vol. 281, pp. 1509-1512.
Hoffman, B. et al., "The proto-oncogene c-myc in hematopoietic development and leukemogenesis" Oncogene 2002, vol. 21, pp. 3414-3421.
Ikeda et al., "Axin, a negative regulator of the Wnt signaling pathway, forms a complex with GSK-3β and β-catenin and promotes GSK-3β-dependent phosphorylation of β-catenin", The EMBO Journal, 1998, vol. 17, No. 5, pp. 1371-1384.
Ioannidis, V. et al., "The beta-catenin-TCF-1 pathway ensures CD4(+)CD8(+) thymocyte survival", Nature Immunology, Aug. 2001, vol. 2, No. 8, pp. 691-697.
Kosuga S. et al., "GSK-3B Directly Phosphorylates and Activates MARK2/PAR-1", The Journal of Biological Chemistry, Dec. 2005, vol. 280, No. 52, pp. 42715-42722.
Kurosu, T. et al., "p38 MAP kinase plays a role in G2 checkpoint activation and inhibits apoptosis of human B cell lymphoma cells treated with etoposide", Apoptosis, Oct 2005, vol. 10, No. 5, pp. 1111-1120.
Lau, K. et al., "Expression analysis of glycogen synthase kinase-3 in human tissue", J. Peptide Res., 1999, vol. 54, pp. 85-91.
Liu, C. et al., "Control of B-Catenin Phosphorylation/Degradation by a Dual-Kinase Mechanism", Cell, Mar. 2002, vol. 108, pp. 837-847.
Ma, S. et al., "Site-specific Phosphorylation Protects Glycogen Synthase Kinase-3β from Calpain-mediated Truncation of Its N and C Termini", The Journal of Biological Chemistry, Jun. 2012, vol. 287, No. 27, pp. 22521-22532.
McManus, E. et al., "Role that phosphorylation of GSK3 plays in insulin and Wnt signalling defined by knockin analysis", The EMBO Journal, 2005; vol. 24, No. 8, pp. 1571-1583.
Mikhailov, A. et al., "The p38-Mediated Stress-Activated Checkpoint", Cell Cycle, Jan. 2005, vol. 4:1, pp. 57-62.
Pedraza-Alva, G. et al., "Activation of p38 Map kinase by DNA double-strand breaks in V(D)J recombination induces a G2/M cell cycle checkpoint", The EMBO Journal, 2006, vol. 25, pp. 763-773.
Raingeaud, J., et al., "MKK3- and MKK6-Regulated Gene Expression Is Mediated by the p38 Mitogen-Activated Protein Kinase Signal Transduction Pathway", Molecular and Cellular Biology, Mar. 1996, vol. 16, No. 3, pp. 1247-1255.
Reinhardt, H. et al., "p53 deficient cells rely on ATM and ATR-mediated checkpoint signaling through the p38 MAPK/MK2pthwy for survival after DNA damage", Cancer Cell, Feb. 2007, vol. 11(2), pp. 175-189.
Rincon, M. et al., "Reprogramming the signalling requirement for AP-1 (activator protein-1) activation during differentiation of precursor CD4+ T-cells into effector Th1 and Th2 cells", Genes and Function, Feb. 1997, pp. 51-68.
Salahshor, S. et al., "The links between axin and carcinogenesis", J. Clin Pathol, 2005, vol. 58, pp. 225-236.
Schreiber, E. et al., "Rapid detection of octamer binding proteins with "mini-extracts", prepared from a small number of cells", Nucleic Acids Research, 1989, vol. 17, No. 15, p. 6419.
She, Q. et al., "ERKs and P38 Kinase Phosphorylate p53 Protein at Serine 15 in Response to UV Radiation", The Journal of Biological Chemistry, Jul. 2000, vol. 275, No. 27, pp. 20444-20449.
Thornton, T. et al., "Phosphorylation by p38 MAPK as an Alternate Pathway for GSK3β Inactivation", Science, May 2008, vol. 320, pp. 667-670.
Tseng, A. et al., "The GSK-3 Inhibitor BIO Promotes Proliferation in Mammalian Cardiomyocytes" Chemistry & Biology, Sep. 2006, vol. 13, pp. 957-963.
UniProtKB/Swiss-Prot Submission; Accession No. P49841, submitted Apr. 8, 2008.
Van Der Heide, L. et al., "Insulin inhibits extracellular regulated kinase ½ phosphorylation in a phosphatidylinositol 3-kinase (P13) kinase-dependent manner in Neuro2a cells", Journal of Neurochemistry, 2003, vol. 86, pp. 86-91.
Zarubin, T. et al., "Activation and signaling of the p38 MAP kinase pathway", Cell Research, Jan. 2005, vol. 15 (1), pp. 11-18.
International Search Report dated Dec. 31, 2009 for International Patent Application No. PCT/US2009/002609, 5 pages.
Written Opinion of the International Searching Authority dated Dec. 31, 2009 for International Patent Application No. PCT/US2009/002609, 5 pages.
Cohen, P. and M. Goedert, "GSK3 Inhibitors: Development and Therapeutic Potential", Nature Reviews, Jun. 2004, vol. 3, pp. 479-487.
Deshayes, S. et al., "Delivery of proteins and nucleic acids using a non-covalent peptide-based strategy", Adv Drug Deliv Rev., Mar. 1, 2008, 1 page, Abstract only.
Lo, D. et al., "Intracellular protein therapy with SOCS3 inhibits inflammation and apoptosis", Nature Medicine, Aug. 2005, vol. 11, 7 pages.
Kuriyama, M. et al., "A Cell-permeable NFAT Inhibitor Peptide Prevents Pressure-Overload Cardiac Hypertrophy", Chem Biol Drug Des, 2006, vol. 67, 6 pages.
Shin, I. et al., "Proapoptotic Activity of Cell-Permeable Anti-Akt Single-Chain Antibodies", Cancer Res, Apr. 1, 2005, vol. 65, 10 pages.

* cited by examiner

SEQUENCE LISTING

```
<160> NUMBER OF SEQ ID NOS: 98

<210> SEQ ID NO 1
<211> LENGTH: 420
<212> TYPE: PRT
<213> ORGANISM: Homo sapiens

<400> SEQUENCE: 1

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95
```

-continued

```
Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Val
    290                 295                 300

Phe Arg Pro Arg Thr Pro Pro Glu Ala Ile Ala Leu Cys Ser Arg Leu
305                 310                 315                 320

Leu Glu Tyr Thr Pro Thr Ala Arg Leu Thr Pro Leu Glu Ala Cys Ala
                325                 330                 335

His Ser Phe Phe Asp Glu Leu Arg Asp Pro Asn Val Lys Leu Pro Asn
            340                 345                 350

Gly Arg Asp Thr Pro Ala Leu Phe Asn Phe Thr Thr Gln Glu Leu Ser
        355                 360                 365

Ser Asn Pro Pro Leu Ala Thr Ile Leu Ile Pro Pro His Ala Arg Ile
    370                 375                 380

Gln Ala Ala Ala Ser Thr Pro Thr Asn Ala Thr Ala Ala Ser Asp Ala
385                 390                 395                 400

Asn Thr Gly Asp Arg Gly Gln Thr Asn Asn Ala Ala Ser Ala Ser Ala
                405                 410                 415

Ser Asn Ser Thr
            420
```

<210> SEQ ID NO 2
<211> LENGTH: 7134
<212> TYPE: DNA
<213> ORGANISM: Homo sapiens

<400> SEQUENCE: 2

```
cgggcttgtg ccgccgccgc cgccgccgcc gcccgggcca agtgacaaag gaaggaagga     60

agcgaggagg agccggcccc gcagccgctg acagggctct gggctggggc aaagcgcgga    120

cacttcctga gcgggcaccg agcagagccg aggggcggga gggcggccga gctgttgccg    180

cggacggggg agggggcccc gagggacgga agcggttgcc gggttcccat gtccccggcg    240
```

-continued

```
aatggggaac agtcgaggag ccgctgcctg ggtctgaagg ggagctgcct ccgccaccgc    300
catggccgct ggatccagcc gccgcctgca gctgctcctg gcgcaatgag gagaggagcc    360
gccgccaccg ccaccgcccg cctctgactg actcgcgact ccgccgccct ctagttcgcc    420
gggcccctgc cgtcagcccg ccggatcccg cggcttgccg gagctgcagc gtttcccgtc    480
gcatctccga gccacccct ccctccctct ccctccctcc tacccatccc cctttctctt    540
caagcgtgag actcgtgatc cttccgccgc ttcccttctt cattgactcg gaaaaaaaat    600
ccccgaggaa aatataatat tcgaagtact cattttcaat caagtatttg cccccgtttc    660
acgtgataca tattttttta ggatttgccc tctcttttct ctcctcccag gaaagggagg    720
ggaaagaatt gtatttttc ccaagtccta aatcatctat atgttaaata tccgtgccga    780
tctgtcttga aggagaaata tatcgcttgt tttgtttttt atagtataca aaaggagtga    840
aaagccaaga ggacgaagtc tttttctttt tcttctgtgg gagaacttaa tgctgcattt    900
atcgttaacc taacacccca acataaagac aaaaggaaga aaaggaggaa ggaaggaaaa    960
ggtgattcgc gaagagagtg atcatgtcag ggcggcccag aaccacctcc tttgcggaga   1020
gctgcaagcc ggtgcagcag ccttcagctt ttggcagcat gaaagttagc agagacaagg   1080
acggcagcaa ggtgacaaca gtggtggcaa ctcctgggca gggtccagac aggccacaag   1140
aagtcagcta tacagacact aaagtgattg gaaatggatc atttggtgtg gtatatcaag   1200
ccaaactttg tgattcagga gaactggtcg ccatcaagaa agtattgcag gacaagagat   1260
ttaagaatcg agagctccag atcatgagaa agctagatca ctgtaacata gtccgattgc   1320
gttatttctt ctactccagt ggtgagaaga aagatgaggt ctatcttaat ctggtgctgg   1380
actatgttcc ggaaacagta tacagagttg ccagacacta tagtcgagcc aaacagacgc   1440
tccctgtgat ttatgtcaag ttgtatatgt atcagctgtt ccgaagttta gcctatatcc   1500
attcctttgg aatctgccat cgggatatta aaccgcagaa cctcttgttg gatcctgata   1560
ctgctgtatt aaaactctgt gactttggaa gtgcaaagca gctggtccga ggagaaccca   1620
atgtttcgta tatctgttct cggtactata gggcaccaga gttgatcttt ggagccactg   1680
attatacctc tagtatagat gtatggtctg ctggctgtgt gttggctgag ctgttactag   1740
gacaaccaat atttccaggg gatagtggtg tggatcagtt ggtagaaata atcaaggtcc   1800
tgggaactcc aacaagggag caaatcagag aaatgaaccc aaactacaca gaatttaaat   1860
tccctcaaat taaggcacat ccttggacta aggattcgtc aggaacagga catttcacct   1920
caggagtgcg ggtcttccga ccccgaactc caccggaggc aattgcactg tgtagccgtc   1980
tgctggagta tacaccaact gcccgactaa caccactgga agcttgtgca cattcatttt   2040
ttgatgaatt acgggaccca aatgtcaaac taccaaatgg gcgagacaca cctgcactct   2100
tcaacttcac cactcaagaa ctgtcaagta atccacctct ggctaccatc cttattcctc   2160
ctcatgctcg gattcaagca gctgcttcaa cccccacaaa tgccacagca gcgtcagatg   2220
ctaatactgg agaccgtgga cagaccaata atgctgcttc tgcatcagct tccaactcca   2280
cctgaacagt cccgagcagc cagctgcaca ggaaaaacca ccagttactt gagtgtcact   2340
cagcaacact ggtcacgttt ggaaagaata ttaaaaagag aaaaaaatcc tgttcatttt   2400
agtgttcaat tttttatta ttattgttgt tcttatttaa ccttgtaaaa tatctataaa   2460
tacaaaccaa tttcattgta ttctcacttt gagggagatc caggggggtgg gaggggttgt   2520
ggggaggggg aaagcggagc actagaacat acaatctctc tcccacgaca atcttttttt   2580
attaaaagtc tgctgttgta tactttaaaa acaggactcc tgcctcatgc cccttccaca   2640
```

-continued

```
aaagaagaaa accttttct gtgctgatgg gtttttttga actttgtttt cttttaaagt   2700
ctagtgtgag actttggtat agtgcacagc ttgaaattgg ttgggagctt agcaggtata   2760
actcaacggg gacttaaatg tcacttgtaa aattaatcca tatcttcggg tatttataga   2820
cttgcctttg gcatgttggt ggcaggtgtg gcagacaaag aaatgtgtat cattcgtaac   2880
ccagggaggt caataaagtt tggaactcta cagggaagat tcttagtaga tttgttaagg   2940
ttttgttttg ctctcagtta gtgctagtga tgtagaggct tgtacaggag gctgccagag   3000
gggaagcagc aagcaagact caggcacaca tgctctacag gtggctcttt gtttgcctga   3060
ccaaagttct ttgcaaatct tagcacagtt tcaaactagt gacctgggag gagatggaag   3120
gggtgttgag caggctgagc tagctgctga ggtcaaaggc tgatgagccc agaggaaggg   3180
gacaggtcag ggatacatct caccactgtg aataagtttg tccagatttt tttctaaagt   3240
tacttccctt ggaaagatac acttgagagg acattgtagt taaataatgt gaactgtaac   3300
agtcatctac tggtttattt ttcatatttt ttaattgaaa attgagcttg cagaaatagc   3360
cacattctac acatagttct aattttaaat ccaaatctag aatctgtatt taatttgttt   3420
tttaacctca tgctttttac atttatttat tgatgcatgt cagatggtag aaatattaaa   3480
aactacacat cagaatgata cagtcactta tacctgctga ctttatagga aagctgatga   3540
tataaatgtg tgtatatatg ttatatatac atatattcaa tactgccttt tttttgtct   3600
acagtatcaa aattgactgg ttgaagcatg agaagaatgt ttcccccaca cccagttaag   3660
agtttttgtg tctgttttct ttgtgtatca gtgaacgatg ttaagaatca gtctctcttt   3720
ttgaagaaaa agcaatattc cttggaaagc aaggagaatt gaaggactat gtttgccgtg   3780
aggaaataga ttttcatgac tagtttgttt tatactttta aggttggcat ctatgtgggc   3840
cttatatact ctaaaatgaa ctttagtcac cttggtgctt atgggccatt acttgaccta   3900
tgaatcttta aggcacaatc agttgtactt tacatttaaa gatcacttga gtgatggccg   3960
cctttccctc ctacccgctc cttccccaca tgccttccaa ggttagctgg taactgtagg   4020
gctgcagagc tgagcccatg gttgtgtgta acttgccctc accctcctca ttgccacctt   4080
aggtcacttt atgggtctcg tcctccagag ggttcggaag tggagtctgt tggcagccct   4140
cctgcaggcc ctagcaccct gtcctgctcc ttaactgtgt gtgtgactct ccaagagagt   4200
tgtcctgcct gctgaagtga accagtaccc agaaagacaa ctgtgagcca tcttggtttt   4260
cactcgctgt ttagctgagg tcttgggcca caaaaggggt ttcacaaacc tctggatata   4320
tcagagttta tgagaaagga aacatgctca gtcaaaccaa atcaaacaaa ttgaatttta   4380
tgttttataa agtgcttctg aaagctaaga tttgaaagaa gtctgaaatc aaagtatttg   4440
gcagcataac tccttaaagg tagtggcgtt gatagaccat tttcagacag aatttataaa   4500
gaatctgaaa aggcaggtct gtgatagaga aatggacctg cattcagatc caactgccca   4560
gcaagcgttt ggatgcagac actgctctgg acgtggtata ctccccagag tccataaaaa   4620
tcagtgctta ttttaggaaa caggttgccc cccacaactg gggtaaaaga agagagaaaa   4680
gtcacgcttt tctctcattt cattgtgtgt gcatgtgtgc gtgtgtgtgt gtgtgtgtgt   4740
gtgctgagat gtgtgatttt tctttctcaa ggatcatggt gggatcacag aactctttta   4800
tacaagtgag atccaggtct ctgaatatct ttttgtatat aataataata aaaagctcct   4860
caccaaattc aagcttgtac attatatttt ctttctgtgt ttttaaattt aagttttatt   4920
gttttgtatg taaatatgtg gacccaggaa ctgttattaa tgagcaaaaa gttactgttc   4980
```

-continued

```
agggcagtga ttctgtttaa taatcagaca aaatgtagac gagcttttta aagccatata   5040
gttttaactc tgtacagtag gtaccggcct gtattattgt aacaataact ctagcaatgt   5100
atagtgtatc tatatagttt ggagtgcctt cgcttccatg tgtttttttt tttaatttgt   5160
tctttttaa attttaattg gtttccttta tccatgtctc cctgtccacc ccctttccct   5220
ttgaaataat aactcactca taacagtatc tttgcccctt ccacagttaa gtttcagtga   5280
taccatactc aggagtggga agaggaaatc atattcgtaa tttcatttcg ttgaagccct   5340
gcctttgttt tggttctgaa tgtctttcct cctcggtagc agtgagaccg gtttcatttc   5400
atacttagtc cattcaggga cttagtgtag caccagggag ccctagagct ggaggatatc   5460
gaatagatta aattttgctc gtctcttcca caagccctaa ccatgggtct taaaaacagc   5520
agattctggg agccttccat gctctctctc tctcctcttt tatctacttc cctcccaaat   5580
gagagagtga cagagaattg tttttttata aatcgaagtt tcttaatagt atcaggtttt   5640
gatacgtcag tggtctaaaa tgctatagtg caattactag cagttactgc acggagtgcc   5700
accgtgccaa tagaggactg ttgttttaac aagggaactc ttagcccatt tcctccctcc   5760
cgccatctct acccttgctc aatgaaatat cattttaatt tcttttaaaa aaaatcagtt   5820
taattcttac tgtgtgccca acacgaaggc ctttttttgaa agaaaaatag aatgttttgc   5880
ctcaaagtag tccatataaa atgtcttgaa tagaagaaaa aactaccaaa ccaaaggtta   5940
ctatttttga aacatcgtgt gttcattcca gcaaggcaga agactgcacc ttctttccag   6000
tgacatgctg tgtcattttt tttaagtcct cttaattttt agacacattt ttggtttatg   6060
ttttaacaat gtatgcctaa ccagtcatct tgtctgcacc aatgcaaagg tttctgagag   6120
gagtattctc tatccctgtg gatatgaaga cactggcatt tcatctattt ttccctttcc   6180
tttttaaagg atttaacttt ggaatcttcc aaaggaagtt tggccaatgc cagatcccca   6240
ggaatttggg gggttttctt tcttttcaac tgaaattgta tctgattcct actgttcatg   6300
ttagtgatca tctaatcaca gagccaaaca cttttctccc ctgtgtggaa aagtaggtat   6360
gctttacaat aaaatctgtc ttttctggta gaaacctgag ccactgaaaa taaaagagac   6420
aactagaagc acagtagagt cccagactga gatctacctt tgagaggctt tgaaagtaat   6480
ccctggggtt tggattattt tcacaagggt tatgccgttt tattcaagtt tgttgctccg   6540
ttttgcacct ctgcaataaa agcaaaatga caaccagtac ataaggggtt agcttgacaa   6600
agtagacttc cttgtgttaa tttttaagtt tttttttcct taactatatc tgtctacagg   6660
cagatacaga tagttgtatg aaaatctgct tgcctgtaaa atttgcattt ataaatgtgt   6720
tgccgatgga tcacttgggc ctgtacacat accaattagc gtgaccactt ccatcttaaa   6780
aacaaaccta aaaaacaaaa tttattatat atatatatat atatatataa aggactgtgg   6840
gttgtataca aactattgca aacacttgtg caaatctgtc ttgatataaa ggaaaagcaa   6900
aatctgtata acattattac tacttgaatg cctctgtgac tgattttttt ttcattttaa   6960
atataaactt ttttgtgaaa agtatgctca atgttttttt tccctttccc cattcccttg   7020
taaatacatt ttgttctatg tgacttggtt tggaaatagt taactggtac tgtaatttgc   7080
attaaataaa aagtaggtta gcctggaaat gaaattaaaa aaaaaaaaaa aaaa         7134
```

<210> SEQ ID NO 3
<211> LENGTH: 420
<212> TYPE: PRT
<213> ORGANISM: Mus musculus

<400> SEQUENCE: 3

-continued

```
Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Val
    290                 295                 300

Phe Arg Pro Arg Thr Pro Pro Glu Ala Ile Ala Leu Cys Ser Arg Leu
305                 310                 315                 320

Leu Glu Tyr Thr Pro Thr Ala Arg Leu Thr Pro Leu Glu Ala Cys Ala
                325                 330                 335

His Ser Phe Phe Asp Glu Leu Arg Asp Pro Asn Val Lys Leu Pro Asn
            340                 345                 350

Gly Arg Asp Thr Pro Ala Leu Phe Asn Phe Thr Thr Gln Glu Leu Ser
        355                 360                 365

Ser Asn Pro Pro Leu Ala Thr Ile Leu Ile Pro Pro His Ala Arg Ile
    370                 375                 380

Gln Ala Ala Ala Ser Pro Pro Ala Asn Ala Thr Ala Ala Ser Asp Thr
385                 390                 395                 400

Asn Ala Gly Asp Arg Gly Gln Thr Asn Asn Ala Ala Ser Ala Ser Ala
                405                 410                 415
```

```
Ser Asn Ser Thr
            420


<210> SEQ ID NO 4
<211> LENGTH: 8298
<212> TYPE: DNA
<213> ORGANISM: Mus musculus

<400> SEQUENCE: 4

acacgcccag cggagttgtc cagccaatga ggaaacgggc gcggcgccca gccgtgcagt      60

tcctcccgcg actcgggagt ttcgccgtcc ttaactcttg aggcttttcc ctgagggcca     120

acagctctga ttggccactg tcgctattgt cgactcttct ctctagccag ccacaggaca     180

aggagaaccc tcttcccttc tgttcggcta ccttcggcat tcctcgttgc tggggcgtgg     240

tctcccagcg gcgtctcctc attggttatc caggtcgctc ggctttttcc ggcaggagct     300

gcaagcaagc gacgtctctg attggttccg gcttgggttt cggctctaca gccgaagctg     360

gcgggcgcgg gctcggcgag cgattcccag acgcctgtaa cgcgggcggc ggggcgctgg     420

gcggtgtaag ggctgggtgg gggaggaagg aggcggagga cgagtaggaa gggggagggg     480

gagtggggaa gggctaggcg gctgcgcaga cggcgcgcct cgcacagagc agcccccgac     540

ccggccgaat gcgggcttgt gtcgccgccg tcgccgccgc ctgggccgag tgacaaagga     600

aggaaggcag caaggaggag ccggccttgc agccgctgac agggcttcgg gctccgggca     660

cagcgcggac acttcccgag cagccgctga gcaaaggcga ggggcggagg ccggccgtgc     720

cggggccacg gacgggggag gggaccccga gggacggaag cggttgcctg gttcccatgt     780

ccccggcgta tggggagcag tcagggagcc gctgcctggg gtctgaaggg agctgcctcc     840

gccgccgctg ccgccatggc cgctggatcc agccaccgcc tgcagctgct cctggcgcaa     900

tgaggagagg agccgccgcc accgcccgcc gctgactcgc gactgcgctg ccctccggtt     960

cacccggccg ccgccgccgt cagaccgccg gatcccgctg ctgccggagc cgcagcgttt    1020

gccgtcgcat ctccgagcca tctcctccct ccttcccatc cccttctct tcaagcgtga     1080

ggctcgtgat ccttccgccg cttcccttct tcattgactc ggaaaaaaat ccccgaggaa    1140

aaatataata ctcagagtac ttattttcaa tcaagtattt gccctcgttc acgtgatata    1200

tatatatttt taaggattcc actccaccct ttttctcctc ttccaggaaa gggaggtgaa    1260

agaattgtat ttttctccca gctctaaatc atctatgtgt taaatatccg taccgatctg    1320

tcttgaagaa atacatagct cctttttttt ttccttcttc ttaaatagct atacaaaagg    1380

agtgaaaagc caagagaacg aagtctttct ttctctttct tgcgggagaa cttaatgctg    1440

catttatcat taacctagca ccctaacata aaacaaaagg aagaaaagga ttaaggaagg    1500

aaaaggtgat tcaagaagag ccatcatgtc ggggcgaccg agaaccacct cctttgcgga    1560

gagctgcaag ccagtgcagc agccttcagc ttttggtagc atgaaagtta gcagagataa    1620

agatggcagc aaggtaacca cagtagtggc aactcctggc cagggtcctg acaggccaca    1680

ggaagtcagt tatacagaca cgaaagtgat tggaaatgga tcatttggtg tggtatatca    1740

agccaaactt tgtgattctg gagaactggt tgccatcaag aaagttctac aggacaagcg    1800

atttaagaac cgagagctcc agatcatgag aaagctagac cactgtaaca tagtccgact    1860

gcggtatttc ttctactcga gtggtgagaa gaaagatgag gtctacctta acctggtgct    1920

ggactatgtt ccggagacag tgtacagagt cgccagacac tatagtcgag ccaagcagac    1980

actccctgtg atctatgtca agttgtatat gtatcagctg ttcagaagtc tagcctatat    2040
```

-continued

```
ccattccttt ggaatctgcc atcgagacat taaaccacag aacctcttgt tggatcctga   2100
tacagctgta ttaaaactct gtgactttgg aagtgcaaag cagctggtcc gaggagagcc   2160
caatgtttca tatatctgtt ctcggtacta cagggcacca gagttgatct ttggagccac   2220
tgattacacg tccagtatag atgtatggtc tgcaggctgt gtgttggctg aattgttgct   2280
aggacaacca atatttcctg ggacagtggg tgtggatcag ttggtggaaa taataaaggt   2340
cctaggaaca ccaacaaggg agcaaattag agaaatgaac ccaaattata cagaattcaa   2400
attccctcaa atcaaggcac atccttggac aaaggtcttc cggccccgaa ctccaccaga   2460
ggcaattgca ctgtgcagcc gtctgctgga gtacacacct accgcccggc taacaccact   2520
ggaagcttgt gcacattcat tttcgatga attgcgggac ccaaatgtca aactaccaaa   2580
tgggcgagac acacctgcac tcttcaactt taccactcaa gaactgtcaa gtaaccccc   2640
tctggccacc atccttatcc ctccacatgc tcggattcag gccgctgctt caccgcctgc   2700
caacgccaca gcagcctcag atactaatgc tggagaccgt ggacagacca ataacgccgc   2760
ttctgcatca gcttccaact ccacctgaac agcccccagg agccagctgc gcgggaaaga   2820
ccagcactta cttgagtgcc actcagcaac actggtcacg tttggaaaga aaattaaaaa   2880
gaggaaaaca aaaacaaaaa caaaaaaacc ctgttcattt tagtgttcaa tttttttat   2940
tgttgttctt atttaacctt gtaaaatatc tatataaata caaaccagtt tcattgtatt   3000
ctcacttttc aggagatcca agaggtgggg agggttgggc ggggaggagc agagcattaa   3060
acacaatctc tcccacgaca atcttttctt ttcttttaa agtcagaagt ccgctattgt   3120
ataccttaaa aaccagactc ctgcctcacg cccccaccgc aacagaagaa aacctgttct   3180
gtgctggttt attttctgga tttgttttct tttaaagcct ggcgtaagac tttgatacag   3240
tgcacagctt gaaattggtt gggagcttag caggtgtaac tcaccaggga cttactgtca   3300
cttgtacaat gtgtacttat ccttaggatt tgaagacttg cctttggcgt gtgatgtcag   3360
gtatgacaga caaaaaaaaa aaagacaaag aaaaaccaag gtgtattatt ggtagcccag   3420
ggaggtcact aaaatctgaa gctctaaggg aagatcagag atggattact taaggtttgt   3480
tttgctcttg accagtgcag gtgttgcaga tgccagctta ggaaggctgc tgccaaagga   3540
gagagcgcga cagagtctgt tgggccctga ggtagatctt ggttcacctg accaaaggcc   3600
gcctgcttct cccggtattg ttttgagctg gtaccctagg atgaggctgg agatggtgtt   3660
aagggggcag ctctgggtgc atcggaaagc gaagaacagg aaggtggcag gccaggggca   3720
gatctcacca ctgtgagtga gcttgtccag attttaataa agtcgtttcc cttagaaaaa   3780
cacttgagag aagacatcat agctaagtaa tgtgaactgt tagccagcct actgctttgt   3840
tttccttact ttaattgaaa accaagcttg caagaattgc cacattctta tgcatagctc   3900
taattttaaa tccaaatcta gactctgtat ttaatttctg ctttttaac atcatgcttt   3960
ttaaatttat ttattgatgc atgtcagatc ggccactatg attttaagtg gtagtaatat   4020
taaaaaccac acatcaaaat aataaagtca cttgtatctg ctgactttat aggaaaactg   4080
attatattaa tgtgtatata tgttttatat atacatatat tcaatactgc cttttctttt   4140
tgtctacagt atcaaaattg actgactgaa tcatgaaaag aatgttcccc caccatcacc   4200
attaagagtt ttattttgt tttctttgtt tatcaatgaa tggtgtaaga atcagtctct   4260
tgttttttga agaaaaagca atattccttg gaaagcaagg tggattgaag gattacgttt   4320
gtgtgaggaa cagaactcat aactagtttg ttgatacttt taaggttggt gtctttgtgg   4380
gccttatata ctctaaaatg aaccttggtg cttatgggcc attacttgac ctatgaatct   4440
```

```
ttaaggcaca atcagttatc ttttacattt aaagatcact tgagtaatgg ccaccgctcc   4500
ttccttcctt cccactccct ccccacacat ctgctaaggt gagctgatga ctagggctgt   4560
agggcccttg gttatgtatg agacacagac tcctttaccc tcattacctg accttaagtc   4620
acgttgaggt cttgccctcc aggtggttag gaagaggagt ctcttggcgg cccttataca   4680
ggccctagca ccctgccttg cttctccgac cgtgtgtgta actctccaag agagttgtat   4740
tgtctgccga aatgagttga tgctagaaag acatcagtga ggctgtgcgg ctggctgatc   4800
tcttcaggcc accgaagggg tttctcagac ctccgtttag atcagacttg acaagaaagg   4860
aagcaagccc aaagcaaaca aaggcgcttt tggtaaagcg cttctcagat aattgccgtg   4920
cgaaagactt ctgaaattaa gttatttgac cgcatagttc cttgaagggg gtgacttgga   4980
agaccatttt cagaaagaat ttgtaaagaa tctgagcaag caggtctgtg gcctgagaag   5040
ggaacctgct ttcagattaa actgcccagc ccgacacaga cagtactcca gacttggtgt   5100
gcgtgctaga gtccataaaa gtcagtgctt gttagtgaat actccccacc cccagatacg   5160
gggtaagaga agagtggagg aaagtcaggt gcttttctct gtgtgtgtgt gtgtgcgcgc   5220
gcgcgcgcgt gtgtgtgtgt gtgtgtgtgt gtgtgtgtgt gtgcgcgtgt gcgtgtgtgc   5280
gcacatgtgt gcgtccgtgt gtgtgtgagt gtgtgcctgt gtgtgtgcgc gcgcgcgtgt   5340
gtgtgtgtgt gtatgtgtgt gtgtatgtat gtgggcatgc atgcatatat gagggcttag   5400
gtgcacgatt tttctttctc aaggatcatg gcaggatccc agaactctta tccaagtgag   5460
atccaggtct ctgaatatct ttttgtaaat aataattaaa agctcctcac caaattcaag   5520
cttgtatatt atattttctt tcaatgtttt taaatttaag ttttattgtt ttgtatgtaa   5580
atatgtggac ccaggaactg ttattaatga gcaaaaagtt actgttcagg gcagtgattc   5640
tgttcaataa ccagacaaaa atgtagacga gctttttaaa gccatatagt tttaactctg   5700
tacagtaggt accggcctgt attattgtaa caataactct agcaatgtat agtgtatcta   5760
tatagtttgg agtgccttcg cttccatgtt tttgggtttt tttgttttgt ttttgttttc   5820
tgacttcctt tatccatgtg tccctgtggc cccctttccc tctgagtaac agcagaacag   5880
cacctttgcc cactccacag tttgaatggg gagaggaaac catgttggca gtctcacttc   5940
attctagcct tgcctttgtt tttggttctg ggtgtgtctg tgtcctcagt aacagtgacc   6000
ggtttcattg cggatgcact cagtccgtcc gggacttggt ggagcgctgg gggccccaga   6060
gctgaagggt gtcagatggc atgggtttgt tcatcgcctc tccaagccct ggagtggatc   6120
ctaagcagat tctgggagct cccgagcttg ctctctcctt acctacttcc ctcccaaatg   6180
agagaaagat tgggtttgtt ttattttttaa aaaaaaaaaa aatcactgtc ttggtggcat   6240
ttgggtgccc ccgtgacatt gttagcagtt actgcagggg tgctgtgcag atgagggctg   6300
cgagtggact ctgagcccgt tcctccctcc taccatcttg ctagatgaaa tatcatttta   6360
atttcttttt ttaaaaatca gtttaactgt gcctaatatg gcccatttga aagaaaaaaa   6420
aaagtattcg ttttgccacc aactacttca tgtgtcttga atagaagaag aaaacaaaaa   6480
aaattcacta ccaaaccaaa ggttgctatt tttgagacat cacgagttca ttgctcacgg   6540
cagaagaatg caccttctct cccatgacag actgtcagtt tttaagtctt tttttttttt   6600
tttttttttt ttttttttgg cccatttctt aggcttgtgt tttagcaaag tatacctgcg   6660
tggccatctt gtccacgcca atgcagaggt cctaaaagga ctccctctat tctctatccc   6720
tgtggacgta aagacactgg catctctgtt accttctctt ccctttgcaa gggttttaac   6780
```

-continued

```
tttggaatct tccagagaaa gtttggccaa tgccagatct cccagagttg ggatttttgt   6840

tattttttt ctttgtttta aatcaaattt gtgtctggtt cctatttaca ctactgattg   6900

ttctaatccc agagatgaat atgtttctcc tctgtatgag aagtaagcac cctttatggt   6960

gaaacctgtc tcttgtggta gaaacggaag ccgctgaaaa caaacatcag cacaggagag   7020

ccccaggcag aggtctccct tgagattctt ccgaagcaat cgttggggtc tgggtcagtt   7080

tcacagggtt atgccatttt attcaagtcc gttgctccgt tgtgcagtct ccaccatata   7140

agcaaaaatg acagccagta cataaggggt tagcttgaca aagtagactt ccttgtgttc   7200

atttttaagg ttttttttt cttaactata tctgtctaca ggcagataca gataggtata   7260

tggaaatgtg cttgcctgta aaatttgcat ttataaatgt gttgcgatgg atcacttcgg   7320

cctgtacaca tccaattagc gtgaccactt ccatcttaaa aacaaatcta aacaaaattt   7380

attattatta tatatatata aaggactgtg ggttgtatac aaactattgc aaacacttgt   7440

gcaaatctgt cttgatataa aggaaaagca aacgctgtgt aacattacta cttgaatgcc   7500

tttgtgactg aattttttt ttcattttaa atataaactt ttttgtggaa agtatgctca   7560

atgtttttt cccccctcccc cccattccct tgtaaataca ttttgttcta tgtgacttgg   7620

tttggaaata gttaactggt actgtaattt gcattaaata aaaagtaggt tagcctggaa   7680

atgaaattaa acttcaccag tgtgtggtct ttatttcagt gcccatcccc ctctcttcac   7740

ccttcccact ctgccatcgc cacatgcagt cacactgccg tctccactcc tctgacagag   7800

gaaacatgaa tccttgagag aaaaatcagg actctccttc tctgagatga ccttgctctg   7860

atgtgtagac aggaggtgca gcttccagct tggaaacccc ctggacttaa tgtagagaaa   7920

gctttgcaga cactgctttg gggaaaaaca aacaaaaaac cctgaaaggg acagttgtaa   7980

aacatgtata agctgctgtc tttggttact gtgtccatgg tttggtgtgg ctgtatttat   8040

tttaacttcc atcttattag taatggtcgt tgggagtctt tgtaaaccat gaacaccatg   8100

gacattgggt cagtcccacc catgtaacca acacgtgtgt gagtctgctc atttccaata   8160

ctggataatg tatgttaaca tgttatgtct catagtgcaa acagaaacac catttttag   8220

ggctggctca ttgtcaggcc taaaggttag atataaggtc atgtgactgc tgcttcaata   8280

aagacaaatt tatattgg                                                  8298

<210> SEQ ID NO 5
<211> LENGTH: 420
<212> TYPE: PRT
<213> ORGANISM: Homo sapiens
<220> FEATURE:
<221> NAME/KEY: MOD_RES
<222> LOCATION: (390)..(390)
<223> OTHER INFORMATION: PHOSPHORYLATION

<400> SEQUENCE: 5

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80
```

-continued

```
Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Val
    290                 295                 300

Phe Arg Pro Arg Thr Pro Pro Glu Ala Ile Ala Leu Cys Ser Arg Leu
305                 310                 315                 320

Leu Glu Tyr Thr Pro Thr Ala Arg Leu Thr Pro Leu Glu Ala Cys Ala
                325                 330                 335

His Ser Phe Phe Asp Glu Leu Arg Asp Pro Asn Val Lys Leu Pro Asn
            340                 345                 350

Gly Arg Asp Thr Pro Ala Leu Phe Asn Phe Thr Thr Gln Glu Leu Ser
        355                 360                 365

Ser Asn Pro Pro Leu Ala Thr Ile Leu Ile Pro Pro His Ala Arg Ile
    370                 375                 380

Gln Ala Ala Ala Ser Thr Pro Thr Asn Ala Thr Ala Ala Ser Asp Ala
385                 390                 395                 400

Asn Thr Gly Asp Arg Gly Gln Thr Asn Asn Ala Ala Ser Ala Ser Ala
                405                 410                 415

Ser Asn Ser Thr
            420
```

<210> SEQ ID NO 6
<211> LENGTH: 420
<212> TYPE: PRT
<213> ORGANISM: Mus musculus
<220> FEATURE:
<221> NAME/KEY: MOD_RES
<222> LOCATION: (389)..(389)
<223> OTHER INFORMATION: PHOSPHORYLATION

<400> SEQUENCE: 6

```
Met Ser Gly Arg Pro Arg Thr Thr Ser Phe Ala Glu Ser Cys Lys Pro
```

-continued

```
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Val
    290                 295                 300

Phe Arg Pro Arg Thr Pro Pro Glu Ala Ile Ala Leu Cys Ser Arg Leu
305                 310                 315                 320

Leu Glu Tyr Thr Pro Thr Ala Arg Leu Thr Pro Leu Glu Ala Cys Ala
                325                 330                 335

His Ser Phe Phe Asp Glu Leu Arg Asp Pro Asn Val Lys Leu Pro Asn
            340                 345                 350

Gly Arg Asp Thr Pro Ala Leu Phe Asn Phe Thr Thr Gln Glu Leu Ser
        355                 360                 365

Ser Asn Pro Pro Leu Ala Thr Ile Leu Ile Pro Pro His Ala Arg Ile
    370                 375                 380

Gln Ala Ala Ala Ser Pro Pro Ala Asn Ala Thr Ala Ala Ser Asp Thr
385                 390                 395                 400

Asn Ala Gly Asp Arg Gly Gln Thr Asn Asn Ala Ala Ser Ala Ser Ala
                405                 410                 415

Ser Asn Ser Thr
            420
```

<210> SEQ ID NO 7
<211> LENGTH: 11
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (8)..(8)
<223> OTHER INFORMATION: PHOSPHORYLATION

<400> SEQUENCE: 7

Arg Ile Gln Ala Ala Ala Ser Thr Pro Thr Asn
1 5 10

<210> SEQ ID NO 8
<211> LENGTH: 11
<212> TYPE: PRT
<213> ORGANISM: Artificial Sequence
<220> FEATURE:
<223> OTHER INFORMATION: recombinant peptide

<400> SEQUENCE: 8

Arg Ile Gln Ala Ala Ala Ser Thr Pro Thr Asn
1 5 10

<210> SEQ ID NO 9
<211> LENGTH: 5
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (3)..(3)
<223> OTHER INFORMATION: PHOSPHORYLATION

<400> SEQUENCE: 9

Ala Ser Thr Pro Thr
1 5

<210> SEQ ID NO 10
<211> LENGTH: 6
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (3)..(3)
<223> OTHER INFORMATION: PHOSPHORYLATION

<400> SEQUENCE: 10

Ala Ser Thr Pro Thr Asn
1 5

<210> SEQ ID NO 11
<211> LENGTH: 7
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (3)..(3)
<223> OTHER INFORMATION: PHOSPHORYLATION

<400> SEQUENCE: 11

-continued

Ala Ser Thr Pro Thr Asn Ala
1 5

<210> SEQ ID NO 12
<211> LENGTH: 8
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (3)..(3)
<223> OTHER INFORMATION: PHOSPHORYLATION

<400> SEQUENCE: 12

Ala Ser Thr Pro Thr Asn Ala Thr
1 5

<210> SEQ ID NO 13
<211> LENGTH: 9
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (3)..(3)
<223> OTHER INFORMATION: PHOSPHORYLATION

<400> SEQUENCE: 13

Ala Ser Thr Pro Thr Asn Ala Thr Ala
1 5

<210> SEQ ID NO 14
<211> LENGTH: 10
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (3)..(3)
<223> OTHER INFORMATION: PHOSPHORYLATION

<400> SEQUENCE: 14

Ala Ser Thr Pro Thr Asn Ala Thr Ala Ala
1 5 10

<210> SEQ ID NO 15
<211> LENGTH: 11
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (3)..(3)
<223> OTHER INFORMATION: PHOSPHORYLATION

<400> SEQUENCE: 15

Ala Ser Thr Pro Thr Asn Ala Thr Ala Ala Ser
1 5 10

<210> SEQ ID NO 16
<211> LENGTH: 5
<212> TYPE: PRT
<213> ORGANISM: Artificial Sequence
<220> FEATURE:
<223> OTHER INFORMATION: recombinant peptide
<220> FEATURE:

<221> NAME/KEY: MOD_RES
<222> LOCATION: (4)..(4)
<223> OTHER INFORMATION: PHOSPHORYLATION

<400> SEQUENCE: 16

Ala Ala Ser Thr Pro
1 5

<210> SEQ ID NO 17
<211> LENGTH: 6
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (5)..(5)
<223> OTHER INFORMATION: PHOSPHORYLATION

<400> SEQUENCE: 17

Ala Ala Ala Ser Thr Pro
1 5

<210> SEQ ID NO 18
<211> LENGTH: 7
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (6)..(6)
<223> OTHER INFORMATION: PHOSPHORYLATION

<400> SEQUENCE: 18

Gln Ala Ala Ala Ser Thr Pro
1 5

<210> SEQ ID NO 19
<211> LENGTH: 8
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (7)..(7)
<223> OTHER INFORMATION: PHOSPHORYLATION

<400> SEQUENCE: 19

Ile Gln Ala Ala Ala Ser Thr Pro
1 5

<210> SEQ ID NO 20
<211> LENGTH: 9
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (8)..(8)
<223> OTHER INFORMATION: PHOSPHORYLATION

<400> SEQUENCE: 20

Arg Ile Gln Ala Ala Ala Ser Thr Pro
1 5

<210> SEQ ID NO 21

<211> LENGTH: 10
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (9)..(9)
<223> OTHER INFORMATION: PHOSPHORYLATION

<400> SEQUENCE: 21

Ala Arg Ile Gln Ala Ala Ala Ser Thr Pro
1 5 10

<210> SEQ ID NO 22
<211> LENGTH: 11
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (10)..(10)
<223> OTHER INFORMATION: PHOSPHORYLATION

<400> SEQUENCE: 22

His Ala Arg Ile Gln Ala Ala Ala Ser Thr Pro
1 5 10

<210> SEQ ID NO 23
<211> LENGTH: 7
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (4)..(4)
<223> OTHER INFORMATION: PHOSPHORYLATION

<400> SEQUENCE: 23

Ala Ala Ser Thr Pro Thr Asn
1 5

<210> SEQ ID NO 24
<211> LENGTH: 8
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (5)..(5)
<223> OTHER INFORMATION: PHOSPHORYLATION

<400> SEQUENCE: 24

Ala Ala Ala Ser Thr Pro Thr Asn
1 5

<210> SEQ ID NO 25
<211> LENGTH: 8
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (4)..(4)
<223> OTHER INFORMATION: PHOSPHORYLATION

<400> SEQUENCE: 25

Ala Ala Ser Thr Pro Thr Asn Ala
1 5

<210> SEQ ID NO 26
<211> LENGTH: 9
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (6)..(6)
<223> OTHER INFORMATION: PHOSPHORYLATION

<400> SEQUENCE: 26

Gln Ala Ala Ala Ser Thr Pro Thr Asn
1 5

<210> SEQ ID NO 27
<211> LENGTH: 9
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (4)..(4)
<223> OTHER INFORMATION: PHOSPHORYLATION

<400> SEQUENCE: 27

Ala Ala Ser Thr Pro Thr Asn Ala Thr
1 5

<210> SEQ ID NO 28
<211> LENGTH: 10
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (7)..(7)
<223> OTHER INFORMATION: PHOSPHORYLATION

<400> SEQUENCE: 28

Ile Gln Ala Ala Ala Ser Thr Pro Thr Asn
1 5 10

<210> SEQ ID NO 29
<211> LENGTH: 10
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (4)..(4)
<223> OTHER INFORMATION: PHOSPHORYLATION

<400> SEQUENCE: 29

Ala Ala Ser Thr Pro Thr Asn Ala Thr Ala
1 5 10

<210> SEQ ID NO 30
<211> LENGTH: 11
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (4)..(4)
<223> OTHER INFORMATION: PHOSPHORYLATION

<400> SEQUENCE: 30

Ala Ala Ser Thr Pro Thr Asn Ala Thr Ala Ala
1 5 10

<210> SEQ ID NO 31
<211> LENGTH: 12
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (9)..(9)
<223> OTHER INFORMATION: PHOSPHORYLATION

<400> SEQUENCE: 31

Ala Arg Ile Gln Ala Ala Ala Ser Thr Pro Thr Asn
1 5 10

<210> SEQ ID NO 32
<211> LENGTH: 12
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (4)..(4)
<223> OTHER INFORMATION: PHOSPHORYLATION

<400> SEQUENCE: 32

Ala Ala Ser Thr Pro Thr Asn Ala Thr Ala Ala Ser
1 5 10

<210> SEQ ID NO 33
<211> LENGTH: 13
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (9)..(9)
<223> OTHER INFORMATION: PHOSPHORYLATION

<400> SEQUENCE: 33

His Ala Arg Ile Gln Ala Ala Ala Ser Thr Pro Thr Asn
1 5 10

<210> SEQ ID NO 34
<211> LENGTH: 13
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (4)..(4)
<223> OTHER INFORMATION: PHOSPHORYLATION

<400> SEQUENCE: 34

Ala Ala Ser Thr Pro Thr Asn Ala Thr Ala Ala Ser Asp
1 5 10

<210> SEQ ID NO 35
<211> LENGTH: 10
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (6)..(6)
<223> OTHER INFORMATION: PHOSPHORYLATION

<400> SEQUENCE: 35

Gln Ala Ala Ala Ser Thr Pro Thr Asn Ala
1 5 10

<210> SEQ ID NO 36
<211> LENGTH: 10
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (6)..(6)
<223> OTHER INFORMATION: PHOSPHORYLATION

<400> SEQUENCE: 36

Ala Ala Ala Ser Thr Pro Thr Asn Ala Thr
1 5 10

<210> SEQ ID NO 37
<211> LENGTH: 11
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (7)..(7)
<223> OTHER INFORMATION: PHOSPHORYLATION

<400> SEQUENCE: 37

Ile Gln Ala Ala Ala Ser Thr Pro Thr Asn Ala
1 5 10

<210> SEQ ID NO 38
<211> LENGTH: 11
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (5)..(5)
<223> OTHER INFORMATION: PHOSPHORYLATION

<400> SEQUENCE: 38

Ala Ala Ala Ser Thr Pro Thr Asn Ala Thr Ala
1 5 10

<210> SEQ ID NO 39
<211> LENGTH: 12
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (8)..(8)
<223> OTHER INFORMATION: PHOSPHORYLATION

<400> SEQUENCE: 39

Arg Ile Gln Ala Ala Ala Ser Thr Pro Thr Asn Ala
1 5 10

<210> SEQ ID NO 40
<211> LENGTH: 12
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (5)..(5)
<223> OTHER INFORMATION: PHOSPHORYLATION

<400> SEQUENCE: 40

Ala Ala Ala Ser Thr Pro Thr Asn Ala Thr Ala Ala
1 5 10

<210> SEQ ID NO 41
<211> LENGTH: 5
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (2)..(2)
<223> OTHER INFORMATION: PHOSPHORYLATION

<400> SEQUENCE: 41

Ala Ser Pro Pro Ala
1 5

<210> SEQ ID NO 42
<211> LENGTH: 6
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (2)..(2)
<223> OTHER INFORMATION: PHOSPHORYLATION

<400> SEQUENCE: 42

Ala Ser Pro Pro Ala Asn
1 5

<210> SEQ ID NO 43
<211> LENGTH: 7
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (2)..(2)
<223> OTHER INFORMATION: PHOSPHORYLATION

<400> SEQUENCE: 43

Ala Ser Pro Pro Ala Asn Ala
1 5

<210> SEQ ID NO 44
<211> LENGTH: 8
<212> TYPE: PRT
<213> ORGANISM: Artificial Sequence
<220> FEATURE:

<223> OTHER INFORMATION: recombinant peptide
<220> FEATURE:
<221> NAME/KEY: MOD_RES
<222> LOCATION: (2)..(2)
<223> OTHER INFORMATION: PHOSPHORYLATION

<400> SEQUENCE: 44

Ala Ser Pro Pro Ala Asn Ala Thr
1               5

<210> SEQ ID NO 45
<211> LENGTH: 9
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (2)..(2)
<223> OTHER INFORMATION: PHOSPHORYLATION

<400> SEQUENCE: 45

Ala Ser Pro Pro Ala Asn Ala Thr Ala
1               5

<210> SEQ ID NO 46
<211> LENGTH: 10
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (2)..(2)
<223> OTHER INFORMATION: PHOSPHORYLATION

<400> SEQUENCE: 46

Ala Ser Pro Pro Ala Asn Ala Thr Ala Ala
1               5                   10

<210> SEQ ID NO 47
<211> LENGTH: 11
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (2)..(2)
<223> OTHER INFORMATION: PHOSPHORYLATION

<400> SEQUENCE: 47

Ala Ser Pro Pro Ala Asn Ala Thr Ala Ala Ser
1               5                   10

<210> SEQ ID NO 48
<211> LENGTH: 5
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (4)..(4)
<223> OTHER INFORMATION: PHOSPHORYLATION

<400> SEQUENCE: 48

Ala Ala Ala Ser Pro
1               5

<210> SEQ ID NO 49
<211> LENGTH: 6
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (5)..(5)
<223> OTHER INFORMATION: PHOSPHORYLATION

<400> SEQUENCE: 49

Gln Ala Ala Ala Ser Pro
1               5

<210> SEQ ID NO 50
<211> LENGTH: 7
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (6)..(6)
<223> OTHER INFORMATION: PHOSPHORYLATION

<400> SEQUENCE: 50

Ile Gln Ala Ala Ala Ser Pro
1               5

<210> SEQ ID NO 51
<211> LENGTH: 8
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (7)..(7)
<223> OTHER INFORMATION: PHOSPHORYLATION

<400> SEQUENCE: 51

Arg Ile Gln Ala Ala Ala Ser Pro
1               5

<210> SEQ ID NO 52
<211> LENGTH: 9
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (8)..(8)
<223> OTHER INFORMATION: PHOSPHORYLATION

<400> SEQUENCE: 52

Ala Arg Ile Gln Ala Ala Ala Ser Pro
1               5

<210> SEQ ID NO 53
<211> LENGTH: 10
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (9)..(9)
<223> OTHER INFORMATION: PHOSPHORYLATION

<400> SEQUENCE: 53

His Ala Arg Ile Gln Ala Ala Ala Ser Pro
1 5 10

<210> SEQ ID NO 54
<211> LENGTH: 11
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (10)..(10)
<223> OTHER INFORMATION: PHOSPHORYLATION

<400> SEQUENCE: 54

Pro His Ala Arg Ile Gln Ala Ala Ala Ser Pro
1 5 10

<210> SEQ ID NO 55
<211> LENGTH: 5
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (3)..(3)
<223> OTHER INFORMATION: PHOSPHORYLATION

<400> SEQUENCE: 55

Ala Ala Ser Pro Pro
1 5

<210> SEQ ID NO 56
<211> LENGTH: 6
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (4)..(4)
<223> OTHER INFORMATION: PHOSPHORYLATION

<400> SEQUENCE: 56

Ala Ala Ala Ser Pro Pro
1 5

<210> SEQ ID NO 57
<211> LENGTH: 6
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (3)..(3)
<223> OTHER INFORMATION: PHOSPHORYLATION

<400> SEQUENCE: 57

Ala Ala Ser Pro Pro Ala
1 5

<210> SEQ ID NO 58
<211> LENGTH: 7
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (5)..(5)
<223> OTHER INFORMATION: PHOSPHORYLATION

<400> SEQUENCE: 58

Gln Ala Ala Ala Ser Pro Pro
1 5

<210> SEQ ID NO 59
<211> LENGTH: 7
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (3)..(3)
<223> OTHER INFORMATION: PHOSPHORYLATION

<400> SEQUENCE: 59

Ala Ala Ser Pro Pro Ala Asn
1 5

<210> SEQ ID NO 60
<211> LENGTH: 8
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (6)..(6)
<223> OTHER INFORMATION: PHOSPHORYLATION

<400> SEQUENCE: 60

Ile Gln Ala Ala Ala Ser Pro Pro
1 5

<210> SEQ ID NO 61
<211> LENGTH: 8
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (3)..(3)
<223> OTHER INFORMATION: PHOSPHORYLATION

<400> SEQUENCE: 61

Ala Ala Ser Pro Pro Ala Asn Ala
1 5

<210> SEQ ID NO 62
<211> LENGTH: 9
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (7)..(7)
<223> OTHER INFORMATION: PHOSPHORYLATION

<400> SEQUENCE: 62

Arg Ile Gln Ala Ala Ala Ser Pro Pro
1 5

<210> SEQ ID NO 63
<211> LENGTH: 9
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (3)..(3)
<223> OTHER INFORMATION: PHOSPHORYLATION

<400> SEQUENCE: 63

Ala Ala Ser Pro Pro Ala Asn Ala Thr
1               5

<210> SEQ ID NO 64
<211> LENGTH: 10
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (8)..(8)
<223> OTHER INFORMATION: PHOSPHORYLATION

<400> SEQUENCE: 64

Ala Arg Ile Gln Ala Ala Ala Ser Pro Pro
1               5                   10

<210> SEQ ID NO 65
<211> LENGTH: 10
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (3)..(3)
<223> OTHER INFORMATION: PHOSPHORYLATION

<400> SEQUENCE: 65

Ala Ala Ser Pro Pro Ala Asn Ala Thr Ala
1               5                   10

<210> SEQ ID NO 66
<211> LENGTH: 11
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (9)..(9)
<223> OTHER INFORMATION: PHOSPHORYLATION

<400> SEQUENCE: 66

His Ala Arg Ile Gln Ala Ala Ala Ser Pro Pro
1               5                   10

<210> SEQ ID NO 67
<211> LENGTH: 11
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (3)..(3)

<223> OTHER INFORMATION: PHOSPHORYLATION

<400> SEQUENCE: 67

Ala Ala Ser Pro Pro Ala Asn Ala Thr Ala Ala
1 5 10

<210> SEQ ID NO 68
<211> LENGTH: 12
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (10)..(10)
<223> OTHER INFORMATION: PHOSPHORYLATION

<400> SEQUENCE: 68

Pro His Ala Arg Ile Gln Ala Ala Ala Ser Pro Pro
1 5 10

<210> SEQ ID NO 69
<211> LENGTH: 12
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (3)..(3)
<223> OTHER INFORMATION: PHOSPHORYLATION

<400> SEQUENCE: 69

Ala Ala Ser Pro Pro Ala Asn Ala Thr Ala Ala Ser
1 5 10

<210> SEQ ID NO 70
<211> LENGTH: 7
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (4)..(4)
<223> OTHER INFORMATION: PHOSPHORYLATION

<400> SEQUENCE: 70

Ala Ala Ala Ser Pro Pro Ala
1 5

<210> SEQ ID NO 71
<211> LENGTH: 8
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (5)..(5)
<223> OTHER INFORMATION: PHOSPHORYLATION

<400> SEQUENCE: 71

Gln Ala Ala Ala Ser Pro Pro Ala
1 5

<210> SEQ ID NO 72
<211> LENGTH: 8
<212> TYPE: PRT

<213> ORGANISM: Artificial Sequence
<220> FEATURE:
<223> OTHER INFORMATION: recombinant peptide
<220> FEATURE:
<221> NAME/KEY: MOD_RES
<222> LOCATION: (4)..(4)
<223> OTHER INFORMATION: PHOSPHORYLATION

<400> SEQUENCE: 72

Ala Ala Ala Ser Pro Pro Ala Asn
1               5

<210> SEQ ID NO 73
<211> LENGTH: 9
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (6)..(6)
<223> OTHER INFORMATION: PHOSPHORYLATION

<400> SEQUENCE: 73

Ile Gln Ala Ala Ala Ser Pro Pro Ala
1               5

<210> SEQ ID NO 74
<211> LENGTH: 9
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (4)..(4)
<223> OTHER INFORMATION: PHOSPHORYLATION

<400> SEQUENCE: 74

Ala Ala Ala Ser Pro Pro Ala Asn Ala
1               5

<210> SEQ ID NO 75
<211> LENGTH: 10
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (7)..(7)
<223> OTHER INFORMATION: PHOSPHORYLATION

<400> SEQUENCE: 75

Arg Ile Gln Ala Ala Ala Ser Pro Pro Ala
1               5                   10

<210> SEQ ID NO 76
<211> LENGTH: 10
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (4)..(4)
<223> OTHER INFORMATION: PHOSPHORYLATION

<400> SEQUENCE: 76

Ala Ala Ala Ser Pro Pro Ala Asn Ala Thr 1 5 10

<210> SEQ ID NO 77
<211> LENGTH: 11
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (8)..(8)
<223> OTHER INFORMATION: PHOSPHORYLATION

<400> SEQUENCE: 77

Ala Arg Ile Gln Ala Ala Ala Ser Pro Pro Ala
1 5 10

<210> SEQ ID NO 78
<211> LENGTH: 11
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (4)..(4)
<223> OTHER INFORMATION: PHOSPHORYLATION

<400> SEQUENCE: 78

Ala Ala Ala Ser Pro Pro Ala Asn Ala Thr Ala
1 5 10

<210> SEQ ID NO 79
<211> LENGTH: 12
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (9)..(9)
<223> OTHER INFORMATION: PHOSPHORYLATION

<400> SEQUENCE: 79

His Ala Arg Ile Gln Ala Ala Ala Ser Pro Pro Ala
1 5 10

<210> SEQ ID NO 80
<211> LENGTH: 12
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (4)..(4)
<223> OTHER INFORMATION: PHOSPHORYLATION

<400> SEQUENCE: 80

Ala Ala Ala Ser Pro Pro Ala Asn Ala Thr Ala Ala
1 5 10

<210> SEQ ID NO 81
<211> LENGTH: 12
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES

<222> LOCATION: (8)..(8)
<223> OTHER INFORMATION: PHOSPHORYLATION

<400> SEQUENCE: 81

Ala Arg Ile Gln Ala Ala Ala Ser Pro Pro Ala Asn
1 5 10

<210> SEQ ID NO 82
<211> LENGTH: 12
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (5)..(5)
<223> OTHER INFORMATION: PHOSPHORYLATION

<400> SEQUENCE: 82

Gln Ala Ala Ala Ser Pro Pro Ala Asn Ala Thr Ala
1 5 10

<210> SEQ ID NO 83
<211> LENGTH: 13
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (8)..(8)
<223> OTHER INFORMATION: PHOSPHORYLATION

<400> SEQUENCE: 83

Ala Arg Ile Gln Ala Ala Ala Ser Pro Pro Ala Asn Ala
1 5 10

<210> SEQ ID NO 84
<211> LENGTH: 13
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (6)..(6)
<223> OTHER INFORMATION: PHOSPHORYLATION

<400> SEQUENCE: 84

Ile Gln Ala Ala Ala Ser Pro Pro Ala Asn Ala Thr Ala
1 5 10

<210> SEQ ID NO 85
<211> LENGTH: 14
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (8)..(8)
<223> OTHER INFORMATION: PHOSPHORYLATION

<400> SEQUENCE: 85

Ala Arg Ile Gln Ala Ala Ala Ser Pro Pro Ala Asn Ala Thr
1 5 10

<210> SEQ ID NO 86
<211> LENGTH: 14

<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (7)..(7)
<223> OTHER INFORMATION: PHOSPHORYLATION

<400> SEQUENCE: 86

Arg Ile Gln Ala Ala Ala Ser Pro Pro Ala Asn Ala Thr Ala
1 5 10

<210> SEQ ID NO 87
<211> LENGTH: 15
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (8)..(8)
<223> OTHER INFORMATION: PHOSPHORYLATION

<400> SEQUENCE: 87

Ala Arg Ile Gln Ala Ala Ala Ser Pro Pro Ala Asn Ala Thr Ala
1 5 10 15

<210> SEQ ID NO 88
<211> LENGTH: 17
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (9)..(9)
<223> OTHER INFORMATION: PHOSPHORYLATION

<400> SEQUENCE: 88

His Ala Arg Ile Gln Ala Ala Ala Ser Pro Pro Ala Asn Ala Thr Ala
1 5 10 15

Ala

<210> SEQ ID NO 89
<211> LENGTH: 16
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (8)..(8)
<223> OTHER INFORMATION: PHOSPHORYLATION

<400> SEQUENCE: 89

Ala Arg Ile Gln Ala Ala Ala Ser Pro Pro Ala Asn Ala Thr Ala Ala
1 5 10 15

<210> SEQ ID NO 90
<211> LENGTH: 16
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (9)..(9)
<223> OTHER INFORMATION: PHOSPHORYLATION

<400> SEQUENCE: 90

His Ala Arg Ile Gln Ala Ala Ala Ser Pro Pro Ala Asn Ala Thr Ala
1               5                   10                  15

<210> SEQ ID NO 91
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 91
acagcacctt cagcactct 19

<210> SEQ ID NO 92
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 92
aagttcttgg ctattacgac a 21

<210> SEQ ID NO 93
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 93
gtgggggcgc cccaggcacc a 21

<210> SEQ ID NO 94
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 94
cttccttaat gtcacgcacg atttc 25

<210> SEQ ID NO 95
<211> LENGTH: 10
<212> TYPE: PRT
<213> ORGANISM: Artificial Sequence
<220> FEATURE:
<223> OTHER INFORMATION: recombinant peptide
<220> FEATURE:
<221> NAME/KEY: MOD_RES
<222> LOCATION: (7)..(7)
<223> OTHER INFORMATION: PHOSPHORYLATION

<400> SEQUENCE: 95

Gly Arg Pro Arg Thr Thr Ser Phe Ala Glu
1               5                   10

<210> SEQ ID NO 96
<211> LENGTH: 11
<212> TYPE: PRT
<213> ORGANISM: Artificial Sequence
<220> FEATURE:
<223> OTHER INFORMATION: recombinant peptide

```
<400> SEQUENCE: 96

Arg Ile Gln Ala Ala Ala Ser Thr Pro Thr Asn
1               5                   10


<210> SEQ ID NO 97
<211> LENGTH: 22
<212> TYPE: PRT
<213> ORGANISM: Artificial Sequence
<220> FEATURE:
<223> OTHER INFORMATION: recombinant peptide

<400> SEQUENCE: 97

Ile Gln Ala Ala Ala Ser Thr Pro Thr Asn Ala Thr Ala Ala Ser Asp
1               5                   10                  15

Ala Asn Thr Gly Asp Arg
            20


<210> SEQ ID NO 98
<211> LENGTH: 24
<212> TYPE: PRT
<213> ORGANISM: Artificial Sequence
<220> FEATURE:
<223> OTHER INFORMATION: recombinant peptide

<400> SEQUENCE: 98

Val Thr Thr Val Val Ala Thr Pro Gly Gln Gly Pro Asp Arg Pro Gln
1               5                   10                  15

Glu Val Ser Thr Thr Asp Thr Lys
            20
```

METHODS AND PRODUCTS RELATING TO GSK3β REGULATION

RELATED APPLICATIONS

This application is a continuation of U.S. application Ser. No. 13/887,679, filed May 6, 2013, which is a continuation of U.S. application Ser. No. 12/989,901, filed Jan. 31, 2011, now U.S. Pat. No. 8,445,648, issued on May 21, 2013, which is a national stage filing under U.S.C. § 371 of PCT International application PCT/US2009/002609, filed Apr. 29, 2009 which was published under PCT Article 21(2) in English, which claims the benefit under 35 U.S.C. 119(e) of U.S. provisional application Ser. No. 61/126,133, filed Apr. 30, 2008, the entire content of each referenced application is incorporated by reference herein in its entirety.

GOVERNMENT INTEREST

This invention was made with government support under NIH R01 AI051454 awarded by the National Institutes of Health. The Government has certain rights in the invention.

FIELD OF THE INVENTION

The invention relates to methods and compositions for regulating GSK3β activity. The invention in some aspects includes phosphorylated GSK3β polypeptides, and methods for using these polypeptides in treatment of diseases or conditions characterized by GSK3β activity.

BACKGROUND OF INVENTION

Glycogen Synthase Kinase 3β (GSK3β) is a serine/threonine kinase that regulates many aspects of cell function such as gene expression, apoptosis and metabolism, through phosphorylation of a wide variety of cellular substrates. One of the GSK3β substrates is the Wnt signaling molecule β-catenin. Phosphorylation of β-catenin by GSK3β targets β-catenin for ubiquitination and subsequent degradation. Inhibition of GSK3β activity through phosphorylation is the primary mechanism that regulates this widely expressed active kinase. The protein kinase Akt inhibits GSK3β by phosphorylation at N-terminal serine residues. However, preventing Akt-mediated phosphorylation does not affect the cell survival pathway activated through the GSK3β substrate β-catenin. GSK3β activity is also enhanced by phosphorylation on several tyrosine residues. In some instances GSK3β activity is regulated through its sub-cellular localization. The activity of GSK3β is linked to multiple disorders including neurological disorders, diabetes, and cancer.

SUMMARY OF INVENTION

Aspects of the invention described herein resale to the discovery that p38 mitogen-activated protein kinase (MAPK) inactivates GSK3β by direct phosphorylation at its C-terminus, and this inactivation can lead to an accumulation of β-catenin. p38 MAPK-mediated phosphorylation of GSK3β occurs at least in brain and thymocytes. Activation of β-catenin-mediated signaling through GSK3β inhibition may provide a mechanism for p38 MAPK-mediated survival in specific tissues.

According to an aspect of the invention, isolated GSK3β polypeptide are provided. The isolated polypeptides are fragments of a full-length GSK3β protein and include a phosphorylated residue that corresponds to residue $Thr^{390}$ in a full-length, wild-type, human GSK3β amino acid sequence, or corresponds to residue $Ser^{389}$ in a full-length, wild-type, mouse GSK3β amino acid sequence. In some embodiments, the GSK3β polypeptide is a human GSK3β polypeptide. In certain embodiments, the phosphorylated residue corresponds to the $Thr^{390}$ residue. In some embodiments, the fragment includes the amino acid sequence set forth as: RIQAAAST($PO_3H_2$)PTN (SEQ ID NO:7). In some embodiments, the GSK3β polypeptide is a mouse GSK3β polypeptide. In certain embodiments, the phosphorylated residue corresponds to the $Ser^{389}$ residue. In some embodiments, the fragment includes the amino acid sequence set forth as ARIQAAAS($PO_3H_2$)PPANATA (SEQ ID NO:87).

According to another aspect of the invention, compositions are provided. The compositions include any isolated GSK3β polypeptide of any embodiment of the aforementioned aspect of the invention and a pharmaceutically acceptable carrier.

According to another aspect of the invention, fusion proteins are provided. The fusion proteins include the GSK3β polypeptide of any one of embodiment of the foregoing aspect of the invention.

According to yet another aspect of the invention, isolated antibodies or antigen-binding fragments thereof are provided. The isolated antibody or antigen-binding fragments thereof bind specifically to an epitope of phosphorylated GSK3β polypeptide, wherein the epitope includes a phosphorylated residue that corresponds to residue $Thr^{390}$ in a foil-length, wild-type, human GSK3β amino acid sequence, or corresponds to residue $Ser^{389}$ in a full-lengths wild-type, mouse GSK3β amino acid sequence. In some embodiments, the full-length GSK3β protein is a human GSK3β protein. In some embodiments, the phosphorylated residue corresponds to the $Thr^{390}$ residue. In certain embodiments, the full-length GSK3β protein is a mouse GSK3β protein. In some, embodiments, the phosphorylated residue corresponds to the $Ser^{389}$ residue. In some embodiments, the antibody competitively inhibits the binding of phospho-$S^{389}$ GSK3β antibody to an epitope that includes a phosphorylated residue that corresponds to residue $Ser^{389}$ in a full length mouse GSK3β protein, in some embodiments, the antibody specifically binds to the epitope with a binding affinity of about $1\times10^{-6}$ M, $1\times10^{-7}$ M, $1\times10^{-8}$ M, $1\times10^{-9}$ M, $1\times10^{-10}$ M, $5\times10^{-10}$ M, or $1\times10^{-11}$ M or less. In certain embodiments, the antibody is phospho-$S^{389}$ GSK3β antibody. In some embodiments, the antibody or antigen-binding fragment thereof is attached to a detectable label.

According to an aspect of the invention, a nucleic acid is provided. The nucleic acid encodes any antibody of an embodiment of the aforementioned aspect of the invention. According to another aspect of the invention, a hybridoma that includes the any of the aforementioned nucleic acid molecules is provided. According to another aspect of the invention, a hybridoma cell line that produces the any of the aforementioned antibodies is provided. According to yet another aspect of the invention, an expression vector that includes any of the aforementioned isolated nucleic acid molecules encoding the antibody or antigen-binding fragment thereof are provided. According to another aspect of the invention, a host cell is provided. The host cell is transformed by or transacted with any of the aforementioned expression vectors. According to another aspect of the invention, a plasmid that produces any of the aforementioned antibodies or antigen-binding fragments thereof is provided.

According to yet another aspect of the invention, compositions that include any of the aforementioned antibodies or antigen-binding fragments thereof are provided. In some embodiments, the compositions also include a carrier. In certain embodiments, the carrier is a pharmaceutically acceptable carrier.

According to yet another aspect of the invention, methods of making an antibody that specifically binds to phosphorylated GSK3β protein are provided. The methods include immunizing an animal with the any of the aforementioned polypeptides of any of aspect of the invention. In some embodiments, the method also includes removing a lymph node from the immunized animal, harvesting cells from the removed lymph node, fusing the harvested cells with myeloma cells to make hybridomas, expanding the hybridomas, identifying a hybridoma that produces an antibody that specifically binds to the phosphorylated polypeptide, and collecting the antibody produced by the hybridoma. In certain embodiments, the method also includes harvesting immune cells from the immunized animal, isolating the antibody that specifically binds phosphorylated GSK3β protein, sequencing the antibody, preparing a cell that expresses the antibody sequence, and collecting the expressed antibody. In some embodiments, the polypeptide that includes the amino acid sequence set forth as RIQAAAST($PO_3H_2$) PTN (SEQ ID NO:7). In some embodiments, the polypeptide includes the amino acid sequence set forth as ARIQAAAS($PO_3H_2$)PPANATA (SEQ ID NO:87).

According to yet another aspect of the invention, methods of producing an antibody that specifically binds to a phosphorylated GSK3β polypeptide are provided. The methods include inoculating an animal with any polypeptide of any of the aforementioned aspects of the invention, in which the polypeptide includes a phosphorylated residue that corresponds to residue $Thr^{390}$ in a full-length, wild-type, human GSK3β amino acid sequence, or corresponds to residue $Ser^{389}$ in a full-length, wild-type, mouse GSK3β amino acid sequence, wherein the polypeptide elicits an immune response in the animal to produce the antibody; and isolating the antibody from the animal; wherein the antibody specifically binds to a phosphorylated GSK3β polypeptide. In certain embodiments, the polypeptide includes the amino acid sequence set forth as RIQAAAST($PO_3H_2$)PTN (SEQ ID NO:7). In some embodiments, the polypeptide includes a threonine residue that corresponds to residue $Thr^{390}$ of full-length, wild-type, human GSK3β polypeptide. In some embodiments, the polypeptide includes the amino acid sequence set forth as ARIQAAAS($PO_3H_2$)PPANATA (SEQ ID NO:87). In certain embodiments, the polypeptide includes a serine residue that corresponds to residue $Ser^{389}$ of full-length, wild-type, mouse GSK3β polypeptide.

According to yet another aspect of the invention, methods of reducing activity of GSK3β in a cell are provided. The methods include contacting the cell with a composition comprising an isolated GSK3β polypeptide, wherein the polypeptide is a full-length GSK3β protein or a fragment of a full-length GSK3β protein and includes a phosphorylated residue that corresponds to residue $Thr^{390}$ in a full-length, wild-type, human GSK3β amino acid sequence, or corresponds to residue $Ser^{389}$ in a full-length, wild-type, mouse GSK3β amino acid sequence. In some embodiments, the GSK3β polypeptide is a human GSK3β polypeptide. In some embodiments, the phosphorylated residue corresponds to the $Thr^{390}$ residue. In certain embodiments, the fragment includes the amino acid sequence set forth as: RIQAAAST ($PO_3H_2$)PTN (SEQ ID NO:7). In some embodiments, the GSK3β polypeptide is a mouse GSK3β polypeptide. In some embodiments, the phosphorylated residue corresponds to the $Ser^{389}$ residue. In certain embodiments, the fragment includes the amino acid sequence set forth as ARIQAAAS ($PO_3H_2$)PPANATA (SEQ ID NO:87). In some embodiments, the methods also include contacting the cell with a compound and/or applying a procedure to the cells that results in the phosphorylation of a GSK3β residue that corresponds to residue $Thr^{390}$ in a full-length, wild-type, human GSK3β amino acid sequence, or corresponds to residue $Ser^{389}$ in a full-length, wild-type, mouse GSK3β amino acid sequence. In some embodiments, the compound or procedure modulates expression or activity of a component of the p38 MAPK signaling pathway in the cell. In certain embodiments, the compound or procedure increases expression or activity of p38 MAPK. In some embodiments, the compound includes p38 MAPK. In some embodiments, the method is a method for treating a neurological disease or condition.

According to yet another aspect of the invention, methods of reducing activity of GSK3β in a cell are provided. The methods include contacting the cell with a compound and/or applying a procedure to the cells that results in the phosphorylation of a GSK3β residue that corresponds to residue $Thr^{390}$ in a full-length, wild-type, human GSK3β amino acid sequence, or corresponds to residue $Ser^{389}$ in a full-length, wild-type, mouse GSK3β amino acid sequence. In certain embodiments, the compound or procedure modulates expression or activity of a component of the p38 MAPK signaling pathway in the cell. In some embodiments, the compound or procedure increases expression or activity of p38 MAPK. In some embodiments, the compound includes p38 MAPK. In certain embodiments, the method is a method for treating a neurological disease or condition.

According to yet another aspect of the invention, methods for treating a disease or condition associated with GSK3β activity are provided. The methods include administering to a subject having a disease or condition associated with GSK3β activity a therapeutically effective amount of a composition that includes an isolated GSK3β polypeptide, wherein the polypeptide is a full-length GSK3β protein or a fragment of a full-length GSK3β protein and includes a phosphorylated residue that corresponds to residue $Thr^{390}$ in a full-length, wild-type, human GSK3β amino acid sequence, or corresponds to residue $Ser^{389}$ in a full-length, wild-type, mouse GSK3β amino acid sequence, in some embodiments, the GSK3β polypeptide is a human GSK3β polypeptide. In some embodiments, the phosphorylated residue corresponds to the $Thr^{390}$ residue. In certain embodiments, the polypeptide includes the amino acid sequence set forth as: RIQAAAST($PO_3H_2$)PTN (SEQ ID NO:7). In some embodiments, the GSK3β polypeptide is a mouse GSK3β polypeptide. In some embodiments, the phosphorylated residue corresponds to the $Ser^{389}$ residue. In certain embodiments, the fragment includes the amino acid sequence set forth as ARIQAAAS($PO_3H_2$)PPANATA (SEQ ID NO:87). In some embodiments, the method also includes contacting the cell with a compound and/or applying a procedure to the cells that results in the phosphorylation of a GSK3β residue that corresponds to residue $Thr^{390}$ in a full-length, wild-type, human GSK3β amino add sequence, or corresponds so residue $Ser^{389}$ in a full-length, wild-type, mouse GSK3β amino acid sequence. In some embodiments, the compound or procedure modulates expression or activity of a component of the p38 MAPK signaling pathway in the cell. In certain embodiments, the compound or procedure increases expression or activity of p38 MAPK. In some embodiments, the compound includes p38 MAPK. In some embodiments, the disease or condition is a neurological disease or condition. In some embodiment, the neurological disease or condition is Alzheimer's disease. In certain embodiments, the neurological disease or condition is bipolar disorder. In some embodiments the neurological disease or condition is stroke, cerebral ischemia, spinal cord trauma, head trauma, perinatal hypoxia, hypoglycemic neuronal damage, dementia (including AIDS-induced dementia), Alzheimer's disease, Huntington's Chorea, amyotrophic laterel sclerosis, multiple sclerosis, ocular damage, cognitive disorders, idiopathic and drug-induced Parkinson's disease, amyotrophic lateral sclerosis, tremors, epilepsy, convulsions, migraine (including migraine headache), psychosis, schizophrenia, mood disorders (including depression, mania, bipolar disorders), trigeminal neuralgia, brain edema, pain (including acute and chronic pain states, severe pain, intractable pain, neuropathic pain, and post-traumatic pain), tardive dyskinesia, motor neuron disease, spinal muscular atrophy, progressive supranuclear palsy, or multiple sclerosis.

According to yet another aspect of the invention, methods for treating a disease or condition associated with GSK3β activity are provided. The methods include administering to a subject having a disease or condition associated with GSK3β activity a therapeutically effective amount of a compound and/or application of a procedure that results in the phosphorylation of a GSK3β residue that corresponds to residue $Thr^{390}$ in a full-length, wild-type, human GSK3β amino acid sequence, or corresponds to residue $Ser^{389}$ in a full-length, wild-type, mouse GSK3β amino acid sequence. In some embodiments, the compound or procedure modulates expression or activity of a component of the p38 MAPK signaling pathway in the cell. In certain embodiments, the compound or procedure increases expression or activity of p38 MAPK. In some embodiments, the compound includes p38 MAPK. In some embodiments, the disease or condition is a neurological disease or condition. In certain embodiments, the neurological disease or condition is Alzheimer's disease. In some embodiments, the neurological disease or condition is bipolar disorder. In some embodiments, the neurological disease or condition is Alzheimer's disease. In some embodiments, the neurological disease or condition is bipolar disorder. In certain embodiments the neurological disease or condition is stroke, cerebral ischemia, spinal cord trauma, head trauma, perinatal hypoxia, hypoglycemic neuronal damage, dementia (including AIDS-induced dementia), Alzheimer's disease, Huntington's Chorea, amyotrophic lateral sclerosis, multiple sclerosis, ocular damage, cognitive disorders, idiopathic and drug-induced Parkinson's disease, amyotrophic lateral sclerosis, tremors, epilepsy, convulsions, migraine (including migraine headache), psychosis, schizophrenia, mood disorders (including depression, mania, bipolar disorders), trigeminal neuralgia, brain edema, pain (including acute and chronic pain states, severe pain, intractable pain, neuropathic pain, and post-traumatic pain), tardive dyskinesia, motor neuron disease, spinal muscular atrophy, progressive supranuclear palsy, or multiple sclerosis.

According to an aspect of the invention, methods of increasing activity of GSK3β in a cell are provided. The methods include contacting the cell with a compound and/or applying a procedure to the cells that reduces phosphorylation of a residue that corresponds to residue $Thr^{390}$ in a full-length, wild-type, human GSK3β amino acid sequence, or corresponds to residue $Ser^{389}$ in a full-length, wild-type, mouse GSK3β amino acid sequence. In some embodiments, the compound or procedure modulates expression or activity of a component of the p38 MAPK signaling pathway in the cell. In some embodiments, the compound or procedure reduces expression or activity of p38 MAPK in the cell. In some embodiments, the method is a method for treating cancer.

According to yet another aspect of the invention, methods of treating a disease or condition associated with reduced GSK3β activity are provided. The methods include administering to a subject having a disease or condition associated with reduced GSK3β activity a therapeutically effective amount of a compound and/or application of a procedure of the cells that reduces phosphorylation of a residue that corresponds to residue $Thr^{390}$ in a full-length, wild-type, human GSK3β amino acid sequence, or corresponds to residue $Ser^{389}$ in a full-length, wild-type mouse GSK3β amino acid sequence. In certain embodiments, the compound or procedure modulates expression or activity of a component of the p38 MAPK signaling pathway in the cell. In some embodiments, the compound or procedure reduces expression or activity of p38 MAPK in the cell. In some embodiments, the disease or condition is cancer.

According to yet anther aspect of the invention, methods of identifying a compound that modulates GSK3β activity are provided. The methods include (a) contacting a GSK3β polypeptide of any of the aforementioned aspects of the invention that includes a phosphorylated residue that corresponds to residue $Thr^{390}$ in a full-length, wild-type, human GSK3β amino acid sequence, with p38 MAPK and a putative modulating compound under suitable conditions for phosphorylation of the residue that corresponds to residue $Thr^{390}$ in a lull-length, wild-type, human GSK3β amino acid sequence; (b) detecting the level of phosphorylation of the GSK3β residue that corresponds to residue $Thr^{390}$ in a full-length, wild-type, human GSK3β amino acid sequence. In the contacted polypeptide; (c) comparing the level of phosphorylation of the GSK3β residue that corresponds to residue $Thr^{390}$ in a full-length, wild-type, human GSK3β amino acid sequence. In the contacted polypeptide to a level of phosphorylation of the corresponding residue in a control GSK3β polypeptide not contacted with the compound, wherein if the level of phosphorylation is higher in the contacted polypeptide than in the control polypeptide the compound is identified as an inhibitor of GSK3β activity and if the level of phosphorylation is lower in the contacted polypeptide than in the control polypeptide the compound is identified as an enhancer of GSK3β activity.

According to an aspect of the invention, methods of identifying a compound that modulates GSK3β activity are provided. The methods include (a) contacting a GSK3β polypeptide of any of the aforementioned aspects of the invention that includes a phosphorylated residue that corresponds to residue $Ser^{389}$ in a full-length, wild-type, mouse GSK3β amino acid sequence, with p38 MAPK and a putative modulating compound under suitable conditions for phosphorylation of the residue that corresponds to residue $Ser^{389}$ in a full-length, wild-type, mouse GSK3β amino acid sequence; (b) detecting the level of phosphorylation of the GSK3β residue that corresponds to residue $Ser^{389}$ in a full-length, wild-type, mouse GSK3β amino acid sequence. In the contacted polypeptide; and (c) comparing the level of phosphorylation of the GSK3β residue that corresponds to residue $Ser^{389}$ in a full-length, wild-type, mouse GSK3β amino acid sequence, in the contacted polypeptide to a level of phosphorylation of the corresponding residue in a control GSK3β polypeptide not contacted with the compounds wherein if the level of phosphorylation is higher in the contacted polypeptide than its the control polypeptide the compound is identified as an inhibitor of GSK3β activity and if the level of phosphorylation is lower in the contacted polypeptide than in the control polypeptide the compound is identified as an enhancer of GSK3β activity.

According to one aspect of the invention, kits are provided. A kit of the invention may include any of the polypeptides of the aforementioned aspects of the invention.

BRIEF DESCRIPTION OF DRAWINGS

Fig. presents Western blots showing regulation of the β-catenin pathway by p38 MAPK.

Fig. presents Western blots showing direct phosphorylation of GSK3β by p38 MAPK.

Fig. presents Western blots and graphs showing that inhibition of GSK3β by p38 MAPK is mediated by phosphorylation at $Thr^{390}$.

Fig. presents Western blots and graphs showing phosphorylation of endogenous GSK3β by p38 MAPK.

Fig. presents MS/MS spectra identifying a TP motif-containing phosphopeptide IQAAASTPTNATAASDANTGDR (SEQ ID NO:97) at the C-terminus of GSK3β as a target for p38 MAPK.

Fig. shows activated p38 MAPK in different tissues.

DETAILED DESCRIPTION

Figure 1A:
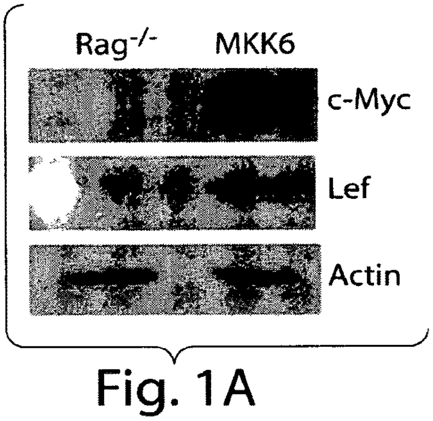
FIG. 1A is a Western blot showing c-Myc and Lef in whole cell extracts from $Rag^{-/-}$ thymocytes ($Rag^{-/-}$) and MKK6 thymocytes (MKK6). Actin was examined as a control.

Aspects of the invention relate to compositions and methods for regulation of GSK3β activity. The invention is based at least in part on the surprising discovery that p38 MAPK phosphorylates GSK3β at a C-terminal residue, distinct from the N-terminal GSK3β residues phosphorylated by Akt. The C-terminal GSK3β residue phosphorylated by p38 corresponds to residue $Thr^{390}$ in a full-length, wild-type, human GSK3β amino acid sequence, or corresponds to residue $Ser^{389}$ in a full-length, wild-type, mouse GSK3β amino acid sequence. Described herein are GSK3β polypeptides containing phosphorylated residues and antibodies that recognize GSK3β polypeptides containing phosphorylated residues. Also described herein are methods for regulating GSK3β activity through phosphorylation of the residue corresponding to residue $Thr^{390}$ in a full-length, wild-type, human GSK3β amino acid sequence, or corresponding to residue $Ser^{389}$ in a full-length, wild-type, mouse GSK3β amino acid sequence. Aspects of the invention further relate to treatment of disorders that are characterized by elevated or reduced GSK3β activity, through the use of phosphorylated GSK3β polypeptides described herein and through modulation of the p38 signaling pathway. Further described herein are screening methods to identify compounds that can modulate GSK3β activity.

Polypeptides

The present invention relates to phosphorylated GSK3β polypeptides. A wild-type, full-length human GSK3β polypeptide has the amino acid sequence set forth as Swissprot Accession No. P49841 (SEQ ID NO:1). According to aspects of the invention, a phosphorylated wild-type, full-length human GSK3β polypeptide also has the amino acid sequence set forth as Swissprot Accession No. P49841 but is phosphorylated at least on a threonine residue corresponding to residue 390 of the full-length human GSK3β polypeptide, and designated herein as $Thr^{390}$. A nucleic acid sequence encoding human wild-type, full-length GSK3β is set forth as Genbank Accession No. NM_002093 (SEQ ID NO:2). In some embodiments the phosphorylated GSK3β polypeptides are mouse polypeptides. A wild-type, full-length mouse GSK3β polypeptide has the amino acid sequence set forth as Genbank Accession No. NP_062801 (SEQ ID NO:3). According to aspects of the invention, a phosphorylated wild-type, full-length mouse GSK3β polypeptide also has the amino acid sequence set forth as Genbank, Accession No. NP_062801 but is phosphorylated at least on a serine residue corresponding to residue 389 of the full-length mouse GSK3β polypeptide, and designated herein as $Ser^{389}$. The nucleic acid encoding mouse wild-type GSK3β polypeptide has GenBank Accession No. NM_019827 and is set forth herein as SEQ ID NO:4. It will be understood that a GSK3β polypeptide of the invention may be phosphorylated at one or more residues in addition to being phosphorylated at the residue corresponding to $Thr^{390}$ or $Ser^{389}$ of the human or mouse full-length, wild-type sequences, respectively.

The amino acid sequence of a non-phosphorylated, full-length, human wild-type GSK3β polypeptide is set forth as SEQ ID NO: 1 and the amino acid sequence of a $Thr^{390}$-phosphorylated full-length, human wild-type GSK3β polypeptide is provided as SEQ ID NO:5. The amino acid sequence of a non-phosphorylated, full-length, mouse wild-type GSK3β polypeptide is set forth as SEQ ID NO:3 and the amino acid sequence of a $Ser^{389}$-phosphorylated full-length, mouse wild-type GSK3β polypeptide is provided as SEQ ID NO:6.

The designation of a specific amino acid residue in a mutant or fragment of GSK3β polypeptide is based on the corresponding residue identity in a full-length, wild-type GSK3β polypeptide. In some embodiments, more than one residue in the GSK3β polypeptide is phosphorylated. In some embodiments, only one residue in the GSK3β polypeptide is phosphorylated. In certain embodiments, the GSK3β polypeptide is a human polypeptide and only a $Thr^{390}$ residue is phosphorylated. In certain embodiments, the GSK3β polypeptide is a mouse polypeptide and only a $Ser^{389}$ residue is phosphorylated.

There may be allelic variation in GSK3β polypeptide sequences of the invention including wild-type GSK3β polypeptide sequences and/or mutant GSK3β polypeptide sequences. As used herein, the term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides with altered amino acid sequences. An allelic variant of a polypeptide is a polypeptide encoded by an allelic variant of a gene. It will be understood by those of ordinary skill in the art that such allelic variations may occur in full-length wild-type and mutant GSK3β polypeptides and in fragments of wild-type and mutant polypeptides, GSK3β polypeptides of the invention may be allelic variants of wild-type GSK3β or mutant GSK3β polypeptide sequences. One of ordinary skill in the art will be able to identify how residues of variants of wild-type and mutant GSK3β polypeptide correspond to residues of wild-type GSK3β polypeptide using routine methods.

The invention, in some aspects, includes phosphorylated GSK3β polypeptides. The term, "phosphorylated GSK3β polypeptide" means a GSK3β polypeptide that has been phosphorylated at one or more residues. In some embodiments of the invention, a GSK3β polypeptide may be phosphorylated at a threonine residue. In certain embodiments, a GSK3β polypeptide may be phosphorylated only at the residue that corresponds to the $Thr^{390}$ residue of wild-type, full-length human GSK3β polypeptide. In some embodiments, a phosphorylated GSK3β polypeptide is a phosphorylated GSK3β polypeptide that is phosphorylated at least at the amino acid residue that corresponds to the amino acid residue number 390 of full-length wild-type human GSK3β polypeptide, which is set forth herein as SEQ ID NO:5. The residue in position 390 of wild-type, full-length GSK3β polypeptide is a threonine, and this threonine in the wild-type, full-length polypeptide and the residue that corresponds to this position in fragments and in mutated forms of GSK3β may be referred to herein as "$Thr^{390}$". GSK3β in which at least the $Thr^{390}$ residue is phosphorylated may be referred to herein as $Thr^{390}$-phosphorylated GSK3β. As used herein the term "$Thr^{390}$-phosphorylated GSK3β polypeptide" is a GSK3β polypeptide that is phosphorylated at least at the threonine that corresponds to the $Thr^{390}$ residue of full-length, wild-type GSK3β polypeptide.

In some embodiments of the invention, a GSK3β polypeptide may be phosphorylated at a serine residue. In certain embodiments, a GSK3β polypeptide may be phosphorylated only at the residue that corresponds to the $Ser^{389}$ residue of wild-type, full-length mouse GSK3β polypeptide. In some embodiments, a phosphorylated GSK3β polypeptide is a phosphorylated GSK3β polypeptide that is phosphorylated at least at the amino acid residue that corresponds to the amino acid residue number 389 of full-length wild-type mouse GSK3β polypeptide, which is set forth herein as SEQ ID NO:6. The residue in position 389 of wild-type, full-length mouse GSK3β polypeptide is a serine, and this serine in the wild-type, full-length polypeptide and the residue that corresponds to this position in fragments and in mutated forms of GSK3β may be referred to herein as "$Ser^{389}$". GSK3β in which the $Ser^{389}$ residue is phosphorylated may be referred to herein as $Ser^{389}$-phosphorylated GSK3β. As used herein the term "$Ser^{389}$-phosphorylated GSK3β polypeptide" is a GSK3β polypeptide that is phosphorylated at least at the serine that corresponds to the $Ser^{389}$ residue of full-length, wild-type GSK3β polypeptide.

The use of nomenclature to describe the position of phosphorylated residues herein can be further exemplified with a fragment of a full-length human GSK3β polypeptide that includes a phosphorylated threonine residue. One such phosphorylated GSK3β polypeptide is set forth as RIQAAAST($PO_3H_2$)PTN (SEQ ID NO:7). A non-phosphorylated GSK3β polypeptide having the same amino acid sequence as SEQ ID NO:7 is set forth as RIQAAASTPTN (SEQ ID NO:8). The threonine that is residue 8 ($Thr^8$) of SEQ ID NO:8 corresponds to the threonine that is residue 390 ($Thr^{390}$) of the wild-type, full-length human GSK3β polypeptide amino acid sequence, thus the phosphorylated amino acid residue in SEQ ID NO:8 may be referred to as the $Thr^8$ residue of SEQ ID NO: 8, or as the residue that corresponds to the $Thr^{390}$ residue of full-length wild-type human GSK3β polypeptide. Those of ordinary skill in the art can readily determine the correspondence of a phosphorylated residue in a GSK3β polypeptide sequence (wild-type or mutant) with a residue in a full-length, wild-type GSK3β polypeptide using routine sequence comparison methods. One of ordinary skill in the art would be familiar with the existence of different isoforms of proteins and how to determine which amino acid residues are corresponding residues between different isoforms of the same protein, by sequence alignment.

As used herein with respect to polypeptides, proteins, or fragments thereof, "isolated" means separated from its native environment sod present in sufficient quantity to permit its identification or use. Isolated, when referring to a protein or polypeptide, means, for example: (i) selectively produced by expression cloning, (ii) purified as by chromatography or electrophoresis, (iii) synthesized using one or more synthetic methods, etc. isolated proteins or polypeptides may be, but need not be, substantially pure. The term "substantially pure" means that the proteins or polypeptides are essentially free of other substances with which they may be found in production, nature, or in vivo systems to an extent practical and appropriate for their intended use. Substantially pure polypeptides may be obtained naturally or produced using methods described herein and may be purified with techniques well known in the art. Because an isolated protein may be admixed with a pharmaceutically acceptable carrier in a pharmaceutical preparation, the protein may comprise only a small percentage by weighs of the preparation. The protein is nonetheless isolated in that it has been separated from the substances with which it may be associated in living systems, i.e. isolated from other proteins.

According to some aspects of the invention, fragments of full-length, wild-type or mutant GSK3β polypeptides are provided, fragments of the invention are preferably fragments that retain a distinct functional capability of the polypeptide. Functional capabilities which can be retained in a fragment include interaction with antibodies, interaction with other polypeptides or fragments thereof, kinase activity, etc. Polypeptide fragments can be synthesized using art-known methods, and tested for function using methods exemplified herein.

A fragment of a phosphorylated GSK3β polypeptide may comprise at least 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 200, 300, 400 or 419 (including each integer in between) contiguous amino acids of GSK3β polypeptide having a consecutive sequence found in wild-type GSK3β polypeptide or a modified GSK3β polypeptide sequence as described herein. In some embodiments, a fragment includes a threonine residue that corresponds to $Thr^{390}$ of full-length, wild-type human GSK3β polypeptide. A residue that corresponds to $Thr^{390}$ may or may not be phosphorylated. In some embodiments, a fragment includes a serine residue that corresponds to $Ser^{389}$ of full-length, wild-type mouse GSK3β polypeptide. A residue that corresponds to $Ser^{389}$ may or may not be phosphorylated. Fragments of phosphorylated GSK3β polypeptide can be prepared using synthetic methods known in the art or may be natural fragments of phosphorylated GSK3β polypeptides. Such fragments are useful for a variety of purposes, including in the preparation of molecules that bind specifically to synthetic and naturally phosphorylated GSK3β polypeptides and in immunoassays well known to those of ordinary skill in the art, including competitive binding immunoassays.

Non-limiting examples of fragments of a human GSK3β polypeptide that include a threonine that corresponds to the $Thr^{390}$ of full-length, wild-type GSK3β wherein the residue that corresponds to the $Thr^{390}$ of full-length, wild-type GSK3β is phosphorylated and is indicated by underlining, are ASTPT (SEQ ID NO:9), ASTPTN (SEQ ID NO:10), AS TPTNA (SEQ ID NO:11), ASTPTNAT (SEQ ID NO:12), ASTPTNATA (SEQ ID NO:13), ASTPTNATAA (SEQ ID NO:14), ASTPTNATAAS (SEQ ID NO:15), AASTP (SEQ ID NO:16), AAASTP (SEQ ID NO:17) QAAASTP (SEQ ID NO:18), IQAAASTP (SEQ ID NO:19), RIQAAASTP (SEQ ID NO:20), ARIQAAASTP (SEQ ID NO:21), HARIQAAASTP (SEQ ID NO:22), AASTPTN (SEQ ID NO:23), AAASTPTN (SEQ ID NO:24), AASTPTNA (SEQ ID NO:25), QAAASTPTN (SEQ ID NO:26), AASTPTNAT (SEQ ID NO:27), IQAAASTPTN (SEQ ID NO:28), AAS TPTNATA (SEQ ID NO:29), RIQAAASTPTN (SEQ ID NO:8), AASTPTNATAA (SEQ ID NO:30), ARIQAAAS TPTN (SEQ ID NO:31), AASTPTNATAAS (SEQ ID NO:32), HARIQAAASTPTO (SEQ ID NO:33), AAS TPTNATAASD (SEQ ID NO:34), QAAASTPTNA (SEQ ID NO:35), AAASTPTNAT (SEQ ID NO:36), IQAAAS TPTNA (SEQ ID NO:37), AAASTPTNATA (SEQ ID NO:38), RIQAAASTPTNA (SEQ ID NO:39), and AAAS TPTNATAA (SEQ ID NO:40).

Non-limiting examples of fragments of a mouse GSK3β polypeptide that include a serine that corresponds so the $Ser^{389}$ of full-length, wild-type GSK3β, wherein the residue that corresponds to the $Ser^{389}$ of full-length, wild-type GSK3β is phosphorylated and is indicated by underlining, are ASPPA (SEQ ID NO:41), ASPPAN (SEQ ID NO:42), A SPPANA (SEQ ID NO:43), ASPPANAT (SEQ ID NO:44), ASPPANATA (SEQ ID NO:45), ASPPANATAA (SEQ ID NO:46), ASPPANATAAS (SEQ ID NO:47), AAASP (SEQ ID NO:48), QAAASP (SEQ ID NO:49), IQAAASP (SEQ ID NO:50), RIQAAASP (SEQ ID NO:51), ARIQAAASP (SEQ ID NO:52), HARIQAAASP (SEQ ID NO:53), PHARIQAAASP (SEQ ID NO:54), AASPP (SEQ ID NO:55), AAASPP (SEQ ID NO:56), AASPPA (SEQ ID NO:57), QAAASPP (SEQ ID NO:58), AASPPAN (SEQ ID NO:59), IQAAASPP (SEQ ID NO:60), AASPPANA (SEQ ID NO:61), RIQAAASPP (SEQ ID NO:62), AASPPANAT (SEQ ID NO:63), ARIQAAASTP (SEQ ID NO:64), AA SPPANATA (SEQ ID NO:65), HARIQAAASPP (SEQ ID NO:66), AASPPANATAA (SEQ ID NO:67), PHARIQAAA SPP (SEQ ID NO:68), AASPPANATAAS (SEQ ID NO:69), AAASPPA (SEQ ID NO:70), QAAASPPA (SEQ ID NO:71), AAASPPAN (SEQ ID NO:72), IQAAASPPA (SEQ ID NO:73), AAASPPANA (SEQ ID NO:74), RIQAAA SPPA (SEQ ID NO:75), AAASPPANAT (SEQ ID NO:76), ARIQAAASPPA (SEQ ID NO:77), AAASPPANATA (SEQ ID NO:78), HARIQAAASPPA (SEQ ID NO:79), AAA SPPANATAA (SEQ ID NO:80), ARIQAAASPPAN (SEQ ID NO: 81), QAAASPPANATA (SEQ ID NO:82), ARIQAAASPPANA (SEQ ID NO:83), IQAAASPPANATA (SEQ ID NO:84), ARIQAAASPPANAT (SEQ ID NO:85), RIQAAASPPANATA (SEQ ID NO:86), ARIQAAA SPPANATA (SEQ ID NO:87), ARIQAAASPPANATA (SEQ ID NO:88), ARIQAAASPPANATAA (SEQ ID NO:89), and HARIQAAASPPANATA (SEQ ID NO:90).

One of ordinary skill in the art will understand how to prepare additional fragments of full-length wild-type or mutant GSK3β polypeptide. A phosphorylated fragment of a full-length wild-type or mutant human GSK3β polypeptide may includes phosphorylated threonine that corresponds to the $Thr^{390}$ threonine of full-length wild-type human GSK3β polypeptide. It should be appreciated that a GSK3β polypeptide that contains a phosphorylated $Thr^{390}$ residue may or may not contain other residues that are also phosphorylated. A phosphorylated fragment of a full-length wild-type or mutant mouse GSK3β polypeptide may include a phosphorylated serine that corresponds to the $Ser^{389}$ serine of full-length wild-type mouse GSK3β polypeptide. It should be appreciated that a GSK3β polypeptide that contains a phosphorylated $Ser^{389}$ residue may or may not contain other residues that are also phosphorylated.

One of ordinary skill in the art will recognize that a GSK3β polypeptide fragment that includes a threonine residue that corresponds to $Thr^{389}$ of full-length, wild-type human GSK3β polypeptide may be a polypeptide that includes a threonine residue that corresponds to the $Thr^{390}$ residue of full-length, wild-type GSK3β polypeptide with an additional 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 360, 369, 370, 371, 372, 373, 374, 375, 376, 377 378, 379, 380, 381, 382, 383, 384, 385, 386, 387, 388, 389, 390, 391, 392, 392, 394, 395, 396, 397, 398, 399, 400, 401, 402, 403, 404, 405, 406, 407, 408, 409, 410, 411, 412, 413, 414, 415, 416, 417 or 418 amino acids, including all integers up to the sequence of a full-length wild-type or mutant, human GSK3β polypeptide minus one amino acid. In some embodiments the GSK3β polypeptide is a full-length polypeptide. The additional amino acids may be added to either and/or both the N-terminus or the C-terminus of the threonine that corresponds to a $Thr^{390}$ amino acid, such that the amino acid sequence corresponds to an amino acid sequence of a wild-type or mutant human GSK3β polypeptide, or a modified wild-type or mutant human GSK3β polypeptide.

In some embodiments a GSK3β polypeptide fragment includes a serine residue that corresponds to $Ser^{390}$ of full-length, wild-type mouse GSK3β polypeptide may be a polypeptide that includes a serine residue that corresponds to the $Ser^{389}$ residue of full-length, wild-type GSK3β polypeptide with an additional 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 90, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 392, 394, 395, 396, 397, 398, 399, 400, 401, 402, 403, 404, 405, 406, 407, 408, 409, 410, 411, 412, 413, 414, 415, 416, 417 or 418 amino acids, including all integers up to the sequence of a full-length wild-type or mutant mouse GSK3β polypeptide minus one amino acid. In some embodiments the GSK3β polypeptide is a full-length polypeptide. The additional amino acids may be added to either and/or both the N-terminus or the C-terminus of the serine that corresponds to a $Ser^{389}$ amino acid, such that the amino acid sequence corresponds to an amino acid sequence of a wild-type or mutant mouse GSK3β polypeptide, or a modified wild-type or mutant mouse GSK3β polypeptide.

One of ordinary skill in the art would be aware that functional homologs of human and/or mouse GSK3β exist in multiple species. Polypeptides including full-length proteins and fragments of full-length proteins from other species, that are functionally homologous to human and/or mouse GSK3β are compatible with the instant invention. One of ordinary skill in the art would further be aware of techniques to identify a residue in a homologous protein that is functionally homologous to residue $Thr^{398}$ in human GSK3β and/or residue $Ser^{389}$ in mouse GSK3β.

A "modified" wild-type or mutant GSK3β polypeptide or fragment thereof may include deletions, point mutations, truncations, amino acid substitutions and/or additions of amino acids or non-amino acid moieties. Modifications of a polypeptide of the invention may be made by modification of the nucleic acid that encodes the polypeptide or alternatively, modifications may be made directly to the polypeptide, such as by cleavage, addition of a linker molecule, addition of a detectable moiety, such as biotin, addition of a carrier molecule, and the like. Modifications also embrace fusion proteins comprising all or part of the polypeptide's amino acid sequence.

In general, modified GSK3β polypeptides include polypeptides that are modified specifically to alter a mature of the polypeptide unrelated to its physiological activity. For example, cysteine residues can be substituted or deleted to prevent unwanted disulfide linkages. Polypeptide modifications can be made by selecting an amino acid substitution, deletion, and/or addition, and a modified polypeptide may be synthesized using art-known methods. Modified polypeptides then can be tested for one or more activities (e.g., kinase activity, antibody binding, antigenicity, ability to interact with a substrate, etc.) to determine which modification provides a modified polypeptide with the desired properties.

The skilled artisan will also realize that conservative amino acid substitutions may be made in a polypeptide to provide functionally equivalent polypeptides, i.e., modified GSK3β polypeptides that retain a functional capability of a wild-type or mutant GSK3β polypeptide. As used herein, a "conservative amino acid substitution" refers to an amino acid substitution that does not alter the relative charge or size characteristics of the protein in which the amino acid substitution is made. Modified GSK3β polypeptides can be prepared according to methods for altering polypeptide sequence and known to one of ordinary skill in the art such. Exemplary functionally equivalent GSK3β polypeptides include conservative amino acid substitutions of an GSK3β polypeptide, or fragments thereof, such as a modified GSK3β polypeptide. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Without wishing to be bound by any theory or mechanism, in some embodiments, phosphorylated GSK3β polypeptides of the invention may inhibit the activity of GSK3β by binding to the catalytic site on the enzyme and competing with internal substrates.

Conservative amino-acid substitutions in a GSK3β polypeptide typically are made by alteration of a nucleic acid encoding the polypeptide. Such substitutions can be made by a variety of methods known to one of ordinary skill in the art. For example, amino acid substitutions may be made by PCR-directed mutation, site-directed mutagenesis, or by chemical synthesis of a gene encoding the GSK3β polypeptide. Where amino acid substitutions are made to a small fragment of a polypeptide, the substitutions can be made by directly synthesizing the polypeptide. The activity of functionally equivalent fragments of GSK3β polypeptides can be tested by cloning the gene encoding the altered polypeptide into a bacterial or mammalian expression vector, introducing the vector into an appropriate host cell, expressing the altered polypeptide, and testing for a functional capability of the polypeptide as disclosed herein.

As described above, a fragment of a full-length wild-type or mutant GSK3β polypeptide may be a synthetic polypeptide. As used herein, the term "synthetic" means artificially prepared. A synthetic polypeptide is a polypeptide that is synthesized and is not a naturally produced polypeptide molecule (e.g., not produced in an animal or organism), it will be understood that the sequence of a natural polypeptide (e.g., an endogenous polypeptide) may be identical to the sequence of a synthetic polypeptide, but the latter will have been prepared using at least one synthetic step.

As used herein, a synthetic phosphorylated polypeptide is a polypeptide phosphorylated with a synthetic method, which may be, but is not limited to a method of the invention. A phosphorylated polypeptide of the invention may be a naturally phosphorylated polypeptide (e.g., a naturally phosphorylated polypeptide) or may be a synthetic phosphorylated polypeptide. Although a synthetic, phosphorylated polypeptide may differ from a natural phosphorylated polypeptide, an antibody raised against a synthetic polypeptide of the invention will specifically bind the synthetic polypeptide epitope against which it was raised, and will also specifically bind the natural epitope in a polypeptide. Thus, even though a phosphorylated epitope of a synthetic polypeptide may differ slightly in amino acid sequence from the same epitope in a natural phosphorylated polypeptide, an antibody raised against a synthetic phosphorylated epitope of the invention specifically binds, in some cases, with high affinity to the natural phosphorylated epitope and to a synthetic phosphorylated epitope. Antibodies of the invention generated using a synthetic phosphorylated polypeptide specifically bind, in some cases, with high affinity so natural and synthetic phosphorylated polypeptides and are able to distinguish between natural (heterogeneous) phosphorylated and natural non-phosphorylated polypeptides and also to distinguish between synthetic phosphorylated and synthetic non-phosphorylated polypeptides.

Antibodies

The invention includes in one aspect, methods and compositions for preparing antibodies that specifically bind synthetic and natural phosphorylated GSK3β. The invention includes, in part, methods for preparing phosphorylated GSK3β polypeptides, including, but not limited to $Thr^{390}$-phosphorylated human GSK3β polypeptides or $Ser^{389}$-phosphorylated mouse GSK3β polypeptides. Phosphorylated GSK3β polypeptides may be used as antigens to make antibodies that specifically bind phosphorylated GSK3β polypeptide. Compositions useful for making an antibody of the invention may include a phosphorylated GSK3β polypeptide. In embodiments of the invention, a phosphorylated GSK3β polypeptide or fragment thereof may be a phosphorylated full-length, wild-type or mutant GSK3β polypeptides or a fragment of a wild-type or mutant full-length GSK3β that is a phosphorylated fragment.

Methods of the invention may also include the use of fragments of GSK3β polypeptides for the production of antibodies that specifically bind phosphorylated GSK3β polypeptides. In some embodiments, a phosphorylated threonine residue of a GSK3β polypeptide that is part of the epitope specifically recognized by the antibody is a threonine residue that corresponds to a phosphorylated residue of wild-type, full-length human GSK3β polypeptide. In certain embodiments, a phosphorylated residue corresponds to residue $Thr^{390}$ of wild-type, full-length human GSK3β polypeptide. In some embodiments, a phosphorylated serine residue of a GSK3β polypeptide that is part of the epitope specifically recognized by the antibody is a serine residue that corresponds to a phosphorylated residue of wild-type, full-length mouse GSK3β polypeptide. In some embodiments, a phosphorylated residue corresponds to residue $Ser^{389}$ of wild-type, full-length mouse GSK3β polypeptide. In some embodiments, an antigenic polypeptide can be as small as 5 amino acids in length. For example, ASTPT(SEQ ID NO:9), ASTPTN (SEQ ID NO: 10), ASTPTNA (SEQ ID NO: 11), ASTPTNAT (SEQ ID NO:12), ASTPTNATA (SEQ ID NO:13), ASTPTNATAA (SEQ ID NO:14), ASTPTNATAAS (SEQ ID NO:15), AASTP (SEQ ID NO:16), AAASTP (SEQ ID NO:17), QAAASTP (SEQ ID NO:18), IQAAASTP (SEQ ID NO:19), RIQAAASTP (SEQ ID NO:20), ARIQAAASTP (SEQ ID NO:21), HARIQAAASTP (SEQ ID NO:22), AASTPTN (SEQ ID NO:23), AAASTPTN (SEQ ID NO:24), AASTPTNA (SEQ ID NO:25), QAAASTPTN (SEQ ID NO:26), AASTPTNAT (SEQ ID NO:27), IQAAASTPTN (SEQ ID NO:28), AASTPTNATA (SEQ ID NO:29), RIQAAASTPTN (SEQ ID NO:8), AASTPTNATAA (SEQ ID NO:30), ARIQAAASTPTN (SEQ ID NO:31), AASTPTNATAAS (SEQ ID NO:32), HARIQAAASTPTN (SEQ ID NO:33), AASTPTNATAASD (SEQ ID NO:34), QAAASTPTNA (SEQ ID NO:35), AAASTPTNAT (SEQ ID NO:36), IQAAASTPTNA (SEQ ID NO:37), AAASTPTNATA (SEQ ID NO:38), RIQAAASTPTNA (SEQ ID NO:39), and AAASTPTNATAA (SEQ ID NO:40) are non-limiting examples of phosphorylated antigenic fragments that may be used to generate antibodies that specifically recognize a $Thr^{390}$-phosphorylated human GSK3β polypeptide, wherein the underlined residue represents the residue that corresponds to $Thr^{390}$ and is phosphorylated.

ASPPA (SEQ ID NO:41), ASPPAN (SEQ ID NO:42), ASPPANA (SEQ ID NO:43), ASPPANAT (SEQ ID NO:44), ASPPANATA (SEQ ID NO:45), ASPPANATAA (SEQ ID NO:46), ASPPANATAAS (SEQ ID NO:47), AAAST (SEQ ID NO:48), QAAASP (SEQ ID NO:49), IQAAASP (SEQ ID NO:50), RIQAAASP (SEQ ID NO:51), ARIQAAASP (SEQ ID NO:52), HARIQAAASP (SEQ ID NO:53), PHARIQAAASP (SEQ ID NO:54), AASPP (SEQ ID NO:55), AAASPP (SEQ ID NO:56), AASPPA (SEQ ID NO:57), QAAASPP (SEQ ID NO:58), AASPPAN (SEQ ID NO:59), IQAAASPP (SEQ ID NO:60), AASPPANA (SEQ ID NO:61), RIQAAASPP (SEQ ID NO:62), AASPPANAT (SEQ ID NO:63), ARIQAAASPP (SEQ ID NO:64), AASPPANATA (SEQ ID NO:65), HARIQAAASPP (SEQ ID NO:66), AASPPANATAA (SEQ ID NO:67), PHARIQAAASPP (SEQ ID NO:68), AASPANATAAS (SEQ ID NO:69), AAASPPA (SEQ ID NO:70), QAAASPPA (SEQ ID NO:71), AAASPPAN (SEQ ID NO:72), IQAAASPPA (SEQ ID NO:73), AAASPPANA (SEQ ID NO:74), RIQAAASPPA (SEQ ID NO:75), AAASPPANAT (SEQ ID NO:76), ARIQAAASPPA (SEQ ID NO:77), AAASPPANATA (SEQ ID NO:78), HARIQAAASPPA (SEQ ID NO:79), AAASPPANATAA (SEQ ID NO:80), ARIQAAASPPAN (SEQ ID NO:81), QAAASPPANATA (SEQ ID NO:82), ARIQAAASPPANA (SEQ ID NO:83), IQAAASPPANATA (SEQ ID NO:84), ARIQAAASPPANAT (SEQ ID NO:85), RIQAAASPPANATA (SEQ ID NO:86), ARIQAAASPPANATA (SEQ ID NO:87), ARIQAAASPPANATA (SEQ ID NO:88), ARIQAAASPPANATAA (SEQ ID NO:89), and HARIQAAASPPANATA (SEQ ID NO:90), are non-limiting examples of phosphorylated antigenic fragments that may be used to generate antibodies that specifically recognize a Ser[389]-phosphorylated mouse GSK3β polypeptide, wherein the underlined residue represents the residue that corresponds to Ser[389] and is phosphorylated. In some embodiments, when the size of the polypeptide antigen is less than about 8 amino acids in length, a second carrier molecule, e.g., bovine serum albumin (BSA), may be attached to the polypeptide to increase antigenicity of the polypeptide. Thus, small fragments of GSK3β that include the desired epitope for antibody production can be used in the production of an antibody that specifically binds to the epitope, which includes a phosphorylated threonine residue (e.g., a Thr[390]-phosphorylated residue or a Ser[389]-phosphorylated residue).

In some embodiments, antibodies that specifically bind ARIQAAAS($PO_3H_2$)PPANATA (SEQ ID NO:87), are provided. In certain embodiments the antibody that specifically binds to ARIQAAAS($PO_3H_2$)PPANATA (SEQ ID NO:87) is phospho-S[389] GSK3β. In the preparation of antibodies that specifically bind to Ser[389]-phosphorylated GSK3β, ARIQAAAS($PO_3H_2$)PPANATA (SEQ ID NO:87) or other GSK3β polypeptide fragments that include a phosphorylated Ser[389] residue may be used. In some embodiments, antibodies that specifically bind RIQAAAST($PO_3H_2$)PTN (SEQ ID NO:7) are provided. In the preparation of antibodies that specifically bind to Thr[390]-phosphorylated GSK3β, RIQAAAST($PO_3H_2$)PTN (SEQ ID NO:7) or other GSK3β polypeptide fragments that include a phosphorylated Thr[390] residue may be used. Any GSK3β polypeptide fragment that includes a phosphorylated serine or threonine residue may be used in conjunction with a second molecule, e.g., keyhole limpet hematocyanin (KLH) or bovine serum albumin (BSA) as described above, as an antigenic polypeptide with which to prepare antibodies that specifically bind to a phosphorylated GSK3β polypeptide. In some embodiments, an antigenic polypeptide may be a polypeptide fragment that includes phosphorylated Thr[390], and an antibody generated from such m antigen will specifically bind to a Thr[390]-phosphorylated epitope of GSK3β polypeptide. In some embodiments, an antigenic polypeptide may be a GSK3β polypeptide fragment that includes phosphorylated Ser[389], and an antibody generated from such an antigen will specifically bind to a Ser[389]-phosphorylated epitope of GSK3β polypeptide. Anti-GSK3β polypeptide antibodies or antigen-binding fragments thereof may be purified using art-known affinity purification and/or affinity selection methods. Affinity selection is selection of antibodies or antigen-binding fragments thereof for binding to the target material (e.g., a phosphorylated GSK3β polypeptide).

It will be understood by those of ordinary skill in the art that it is preferable that a fragment of GSK3β polypeptide for use as an immunogenic fragment in the methods of the invention be at least 5, 6, 7, 8, 9, 10, 11, 12, 13, 14, 15, 16, 18, 18, 19, 20 or more amino acids in length. In some embodiments if a fragment of GSK3β polypeptide includes more than one threonine residue, it is desirable that only one of the threonine residues is a phosphorylated threonine residue. In some embodiments if a fragment of GSK3β polypeptide includes more than one serine residue. It is desirable that only one of the serine residues is a phosphorylated serine residue. One of ordinary skill in the art will be able to use the guidance provided herein to make additional fragments of GSK3β polypeptide that can be used in methods of the invention.

As used herein, the term "antibody" refers to a glycoprotein that may include at least two heavy (H) chains and two light (L) chains inter-connected by disulfide bonds. Each heavy chain is comprised of a heavy chain variable region (abbreviated herein as HCVR or $V_H$) and a heavy chain constant region. The heavy chain constant region is comprised of three domains, $C_H1$, $C_H2$ and $C_H3$. Each light chain is comprised of a light chain variable region (abbreviated herein as LCVR or $V_L$) and a light chain constant region. The light chain constant region is comprised of one domain, CL. The $V_H$ and $V_L$ regions can be farther subdivided into regions of hyper variability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding fragment" of an antibody as used herein, refers to one or more portions of an antibody that retain the ability to specifically bind to an antigen (e.g., phosphorylated GSK3β polypeptide). It has been shown that the antigen-binding function of an antibody can be performed by fragments of a full-length antibody. Examples of binding fragments encompassed within the term "antigen-binding fragment" of an antibody include (i) a fab fragment, a monovalent fragment consisting of the $V_L$, $V_H$, $C_L$ and $C_HI$ domains; (ii) a F(ab')$_2$ fragment, a bivalent fragment comprising two fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al, (1989) *Nature* 341:544-546) which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional procedures, such as proteolytic fragmentation procedures, as described in J. Goding, Monoclonal Antibodies: Principles and Practice, pp 98-118 (N.Y. Academic Press 1983), which is hereby incorporated by reference as well as by other techniques known to those with skill in the art. The fragments are screened for utility in the same manner as are intact antibodies.

Isolated antibodies of the invention encompass various antibody isotypes, such as IgG1, IgG2, IgG3, IgG4, IgM, IgA1, IgA2, IgAsec, IgD, IgE. As used herein, "isotype" refers to the antibody class (e.g., IgM or IgG1) that is encoded by heavy chain constant region genes. Antibodies of the invention can be full length or can include only an antigen-binding fragment such as the antibody constant and/or variable domain of IgG1, IgG2, IgG3, IgG4, IgM, IgA1, IgA2, IgAsec, IgD or IgE or could consist of a Fab fragment, a F(ab')$_2$ fragment, and a Fv fragment.

Antibodies of the present invention can be polyclonal, monoclonal, or a mixture of polyclonal and monoclonal antibodies. Antibodies of the invention can be produced by methods disclosed herein or by a variety of techniques known in the art. In some embodiments, the epitope recognized by an antibody of the invention comprises a phosphorylated threonine that corresponds to the $Thr^{390}$ in full-length, wild-type human GSK3β polypeptide. In some embodiments, the epitope recognized by an antibody of the invention comprises a phosphorylated residue that corresponds to $Ser^{389}$ of wild-type, full-length mouse GSK3β polypeptide.

Polyclonal and monoclonal antibodies may be prepared using techniques that are known in the art. The term "monoclonal antibody," as used herein, refers to a preparation of antibody molecules of single molecular composition. A monoclonal antibody displays a single binding specificity and affinity for a particular epitope. The term "polyclonal antibody" refers to a preparation of antibody molecules that comprises a mixture of antibodies active that specifically bind a specific antigen.

A process of monoclonal antibody production may include obtaining immune somatic sells with the potential for producing antibody, in particular B lymphocytes, which have been previously immunized with the antigen of interest either in vivo or in vitro and that are suitable for fusion with a B-cell myeloma line. Mammalian lymphocytes typically are immunized by in vivo immunization of the animal (e.g., a mouse or other mammal) with the desired protein or polypeptide, e.g., with phosphorylated GSK3β polypeptide or a fragment thereof. $Thr^{390}$-phosphorylated GSK3β or a fragment thereof, or $Ser^{389}$-phosphorylated GSK3β or a fragment thereof, in the present invention. In some embodiments, the polypeptide is a modified polypeptide as described herein. In some embodiments the polypeptide comprises the sequence set forth as SEQ ID NO:7. Such immunizations are repeated as necessary at intervals of up to several weeks to obtain a sufficient titer of antibodies. Once immunized, animals can be used as a source of antibody-producing lymphocytes. Following the last antigen boost, the animals are sacrificed and spleen cells removed. Mouse lymphocytes give a higher percentage of stable fusions with the mouse myeloma lines described herein. Of these, the BALB/c mouse is preferred. However, other mouse strains, rat, rabbit, hamster, sheep, goats, camels, llamas, frogs, etc. may also be used as hosts for preparing antibody-producing cells. (See; Goding in Monoclonal Antibodies: Principles and Practice, 2d ed., pp. 60-61, Orlando, Fla., Academic Press, 1986). Mouse strains that have human immunoglobulin genes inserted in the genome (and that cannot produce mouse immunoglobulins) can also be used. Examples include the HuMAb mouse strains produced by Medarex/GenPharm International, and the XenoMouse strains produced by Abgenix. Such mice produce fully human immunoglobulin molecules in response to immunization.

Those antibody-producing cells that are in the dividing plasmablast stage fuse preferentially. Somatic cells may be obtained from the lymph nodes, spleens and peripheral blood of antigen-primed animals, and the lymphatic cells of choice depend to a large extent on their empirical usefulness in the particular fusion system. The antibody-secreting lymphocytes are then fused with B cell myeloma cells or transformed cells, which are capable of replicating indefinitely in cell culture, thereby producing an immortal, immunoglobulin-secreting cell line. The B cell myeloma cells or transformed cells may be mouse or other suitable mammalian cells. The resulting fused cells, or hybridomas are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature* 256:495 (1975), which is hereby incorporated by reference.

Myeloma cell lines suited for use in hybridoma-producing fusion procedures preferably are non-antibody-producing, have high fusion efficiency, and enzymes deficiencies that render them incapable of growing in certain selective media which support the growth of the desired hybridomas. Examples of such myeloma cell lines that may be used for the production of fused cell lines include, but are not limited to Ag8, P3-X63/Ag8, X63-Ag8.653, NSI/1.Ag 4.1, Sp2/0-Ag14, FO, NSO/U, MPC-11, MPC11-X45-GTG 1.7, S194/5XX0 Bul, all derived from mice; R210.RCY3, Y3-Ag 1.2.3, IR983F and 4B210 derived from rats and U-266, GM1500-GRG2, LICR-LON-HMy2, UC729-6, all derived from humans (Goding, in Monoclonal Antibodies: Principles and Practice, 2d ed., pp. 65-66, Orlando, Fla., Academic Press, 1986; Campbell, in Monoclonal Antibody Technology, Laboratory Techniques in Biochemistry and Molecular Biology Vol. 13, Burden and Von Knippenberg, eds. pp. 75-83, Amsterdam, Elsevier, 1984). Those of ordinary skill in the art will be aware of numerous routine methods to produce monoclonal antibodies.

Fusion with mammalian myeloma cells or other fission partners capable of replicating indefinitely in cell culture is effected by standard and well-known techniques, for example, by using polyethylene glycol ("PEG") or other (using agents (See Milstein and Kohler, *Eur. J. Immunol.* 6:511 (1976), which is hereby incorporated by reference).

Methods for raising polyclonal antibodies are well known to those of ordinary skill in the art. As a non-limiting example, anti-phosphorylated GSK3β polyclonal antibodies may be raised by administering a phosphorylated GSK3β polypeptide subcutaneously to New-Zealand white rabbits which have first been bled to obtain pre-immune serum. The phosphorylated GSK3β can be inoculated with (e.g., injected at) a total volume of 100 μl per site at six different sites, typically with one or more adjuvants. The rabbits are then bled two weeks after the first injection and periodically boosted with the same antigen three times every six weeks. A sample of serum is collected 10 days after each boost. Polyclonal antibodies are recovered from the serum, preferably by affinity chromatography using phosphorylated GSK3β to capture the antibody. This and other procedures for raising polyclonal antibodies are disclosed in E. Harlow, et al., editors, Antibodies: A Laboratory Manual (1988), which is hereby incorporated by reference. Those of ordinary skill in the art will be aware of numerous routine methods to produce polyclonal antibodies. In some embodiments, the epitope recognized by the polyclonal antibody of the invention comprises a phosphorylated residue that corresponds to $Thr^{390}$ of wild-type, full-length human GSK3β polypeptide. In some embodiments, the epitope recognized by the polyclonal antibody of the invention comprises a phosphorylated residue that corresponds to $Ser^{389}$ of wild-type, full-length mouse GSK3β polypeptide.

In other embodiments, antibodies may be recombinant antibodies. The term "recombinant antibody", as used herein, is intended to include antibodies that are prepared, expressed, created or isolated by recombinant means, such as antibodies isolated from an animal (e.g., a mouse, rat, rabbit, etc.) that is transgenic for another species' immunoglobulin genes, genetically engineered antibodies, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

The present invention further provides nucleic acid molecules encoding anti-phosphorylated GSK3β antibodies (e.g., anti-$Thr^{390}$-phosphorylated GSK3β antibodies or anti-$Ser^{389}$-phosphorylated GSK3β antibodies) and vectors comprising the nucleic acid molecules as described herein. The vectors provided can be used to transform or transfect host cells for producing anti-phosphorylated GSK3β antibodies with the specificity of antibodies described herein. In some embodiments the antibodies produced will have the specificity of the phospho-$S^{389}$ GSK3β antibody. In some embodiments, the vectors can include an isolated nucleic acid molecule encoding a heavy chain and/or a light chain of an antibody of the invention encoded by a nucleic acid molecule. In a further embodiment, plasmids are given which produce the antibodies or antigen-binding fragments described herein.

Antibodies or antigen-binding fragments of the invention are, preferably, isolated. "Isolated", as used herein with respect to antibodies and antigen-binding fragments thereof, is intended to refer to an antibody (or antigen-binding fragment thereof) that is substantially free of other antibodies (or antigen-binding fragments) having different antigenic specificities (e.g., an isolated antibody that specifically binds to phosphorylated GSK3β polypeptide is substantially free of antibodies that specifically bind antigens other than phosphorylated GSK3β polypeptide). An isolated antibody that specifically binds to an epitope, isoform or variant of a phosphorylated polypeptide (e.g., phosphorylated GSK3β polypeptide) may, however, have cross-reactivity to other related antigens, e.g., a mutant form of GSK3β, or a polypeptide from other species (e.g., GSK3β species homologs). Moreover, an isolated antibody (or antigen-binding fragment thereof) may be substantially free of other cellular material and/or chemicals.

Antibodies of the invention include, but are not limited to antibodies that specifically bind to a phosphorylated GSK3β polypeptide. In certain embodiments, an antibody of the invention specifically binds GSK3β that is phosphorylated at a residue that corresponds to the $Thr^{398}$ residue of full-length, wild-type human GSK3β polypeptide, in certain embodiments, an antibody of the invention specifically binds GSK3β that is phosphorylated at a residue that corresponds to the $Ser^{389}$ residue of full-length, wild-type mouse GSK3β polypeptide. As used herein, "specific binding" refers to antibody binding to a predetermined antigen with a preference that enables the antibody to be used to distinguish the antigen from others to an extent that permits the diagnostic and other assays described herein. For example specific binding to $Thr^{390}$-phosphorylated GSK3β polypeptide means that the antibody not only preferentially binds GSK3β polypeptide versus other polypeptides, but also that it preferentially binds a phosphorylated GSK3β polypeptide versus a GSK3β polypeptide that is not phosphorylated. The antibody may bind with an affinity that is at least two-fold greater than its affinity for binding to antigens other than the predetermined antigen. In some embodiments, an antibody or antigen-binding fragment thereof of the invention specifically binds to $Thr^{390}$-phosphorylated GSK3β polypeptide. In some embodiments, an antibody or antigen-binding fragment thereof of the invention specifically binds to $Ser^{389}$-phosphorylated GSK3β polypeptide. It will be understood that the GSK3β polypeptide or fragment thereof that includes a phosphorylated residue that corresponds to phosphorylated $Thr^{390}$ of full-length, wild-type human GSK3β polypeptide, or phosphorylated $Ser^{389}$ of full-length, wild-type mouse GSK3β polypeptide may be a wild-type or a mutant form of GSK3β polypeptide—as long as the epitope recognized by an antibody that specifically binds a phosphorylated GSK3β polypeptide residue that includes a residue corresponding to phosphorylated $Thr^{390}$ residue of full-length, wild-type human GSK3β polypeptide, or phosphorylated $Ser^{389}$ residue of full-length, wild-type, mouse GSK3β polypeptide, is present.

Anti-$Thr^{390}$-phosphorylated GSK3β antibodies or antigen-binding fragments thereof, or anti-$Ser^{389}$-phosphorylated GSK3β antibodies or antigen-binding fragments thereof of the invention, can specifically bind $Thr^{390}$-phosphorylated GSK3β polypeptide or $Ser^{389}$-phosphorylated GSK3β polypeptide with sub-nanomolar affinity. The binding affinities can be about $1\times10^{-6}$, $1\times10^{-7}$, $1\times10^{-8}$, $1\times10^{-9}$ or less, preferably about $1\times10^{-10}$ M or less, more preferably $1\times10^{-11}$ M or less. In certain embodiments the binding affinity is less than about $5\times10^{-10}$M.

In some aspects of the invention, an antibody or antigen-binding fragment thereof binds to a conformational epitope within the phosphorylated GSK3β polypeptide. To determine if the selected anti-phosphorylated GSK3β antibodies bind to conformational epitopes, each antibody can be tested in assays using native protein (e.g., non-denaturing immunoprecipitation, flow cytometric analysis of cell surface binding) and denatured protein (e.g., Western blot, immunoprecipitation of denatured proteins). A comparison of the results will indicate whether the antibodies bind conformational epitopes. In some embodiments antibodies that bind to native protein but not denatured protein are those antibodies that bind conformational epitopes, and are preferred antibodies.

In some embodiments of the invention, antibodies competitively inhibit the specific binding of a second antibody to its target epitope on phosphorylated GSK3β polypeptide. In some embodiments, the target epitope comprises a phosphorylated residue that corresponds to $Thr^{390}$ of wild-type, full-length human GSK3β polypeptide or corresponds to $Ser^{389}$ of wild-type, full-length mouse GSK3β polypeptide. In some embodiments, the second antibody is phospo-$S^{389}$ GSK3β. To determine competitive inhibition, a variety of assays known to one of ordinary skill in the art can be employed. For example, competition assays can be used so determine if an antibody competitively inhibits binding to phosphorylated GSK3β (or $Thr^{390}$-phosphorylated GSK3β or $Ser^{389}$-phosphorylated GSK3β) by another antibody (e.g., phospo-$S^{389}$ GSK3β). These methods may include cell-based methods employing flow cytometry or solid phase binding analysis. Other assays that evaluate the ability of antibodies to cross-compete for phosphorylated GSK3β polypeptide (or $Thr^{390}$-phosphorylated GSK3β polypeptide or $Ser^{389}$-phosphorylated GSK3β) molecules in solid phase or in solution phase, also can be used.

Certain antibodies competitively inhibit the specific binding of a second antibody so its target epitope on phosphorylated GSK3β polypeptide (or $Thr^{390}$-phosphorylated GSK3β polypeptide or $Ser^{389}$-phosphorylated GSK3β by at least about 10%, 20%, 30%, 40%, 50%, 60%, 70%, 80%, 90%, 95%, 90% or 100%. Inhibition cars be assessed at various molar ratios or mass ratios; for example competitive binding experiments can be conducted with a 2-fold, 3-fold, 4-fold, 5-fold, 7-fold, 10-fold or more molar excess of the first antibody over the second antibody.

Other antibodies of the invention may include antibodies that specifically bind to an epitope on phosphorylated GSK3β polypeptide defined by a second antibody. To determine the epitope, one can use standard epitope mapping methods known in the art. For example, fragments (polypeptides) of $Thr^{390}$-phosphorylated GSK3β polypeptide antigen or $Ser^{389}$-phosphorylated GSK3β polypeptide antigen that bind the second antibody can be used to determine whether a candidate antibody binds the same epitope. In some embodiments, an epitope comprises a phosphorylated residue that corresponds to $Thr^{390}$ of wild-type, full-length human GSK3β polypeptide. In some embodiments, an epitope comprises a phosphorylated residue that corresponds to $Ser^{389}$ of wild-type, full-length mouse GSK3β polypeptide. In certain embodiments, the second antibody is phospho-$S^{389}$ GSK3β antibody. For linear epitopes, overlapping polypeptides of a defined length (e.g., 5, 6, 7, 8 or more amino acids) may be synthesized. The polypeptides preferably are offset by 1 amino acid, such that a series of polypeptides covering every 4, 5, 6, 7, or 8 amino acid fragment (respectively) of the phosphorylated GSK3β polypeptide sequence are prepared. Fewer polypeptides can be prepared by using larger offsets, e.g., 2 or 3 amino acids. In addition, longer polypeptides (e.g., 9-, 10- or 11-mers) can be synthesized. Binding of polypeptides to antibodies can be determined using standard methodologies including surface plasmon resonance (BIACORE) and ELISA assays. For examination of conformational epitopes, larger phosphorylated GSK3β polypeptide fragments, including in some embodiments $Thr^{390}$-phosphorylated GSK3β polypeptide or $Ser^{389}$-phosphorylated GSK3β polypeptide, can be used. Other methods that use mass spectrometry to define conformational epitopes have been described and can be used (see, e.g., Baerga-Ortiz et al., *Protein Science* 11:1300-1308, 2002 and references cited therein). Still other methods for epitope determination are provided in standard laboratory reference works, such as Unit 6.8 ("Phage Display Selection and Analysis of B-cell Epitopes") and Unit 9.8 ("identification of Antigenic Determinants Using Synthetic Polypeptide Combinatorial Libraries") of *Current Protocols in Immunology*, Coligan et al., eds., John Wiley & Sons. Epitopes can be confirmed by introducing point mutations or deletions into a known epitope, and then testing binding with one or more antibodies to determine which mutations reduce binding of the antibodies.

An antibody or antigen-binding fragment thereof of the invention can be linked to a detectable label. A detectable label of the invention may be attached to antibodies or antigen-binding fragments thereof of the invention by standard protocols known in the art. In some embodiments, the detectable labels may be covalently attached to an anti-phosphorylated GSK3β antibody or antigen-binding fragment thereof of the invention. The covalent binding can be achieved either by direct condensation of existing side chains or by the incorporation of external bridging moieties. Many bivalent or polyvalent agents are useful in coupling protein molecules to other proteins, polypeptides or amine functions, etc. For example, the literature is replete with coupling agents such as carbodiimides, diisocyanates, glutaraldehyde, and diazobenzenes. This list is not intended to the exhaustive of the various coupling agents known in the art but, rather, is exemplary of the more common coupling agents. Additional descriptions of detectable labels useful in the invention are provided elsewhere herein.

The invention, in part, also includes nucleic acid sequences that encode polypeptide sequences for use in generating antibodies. For example, the invention includes nucleic acid sequences that encode a phosphorylated GSK3β polypeptide or fragment thereof described herein, and includes the use of the nucleic acid sequences that may be used to produce polypeptides that can be used as antigens with which to raise antibodies that recognize phosphorylated GSK3β polypeptides described herein.

Additional nucleic acids of the invention include nucleic acids that encode a GSK3β polypeptide, or an antibody or antigen-binding fragment thereof of the invention. In certain embodiments, a nucleic acid of the invention is a nucleic acid molecule that is highly homologous to a nucleic acid that encodes a GSK3β polypeptide or an antibody or antigen-binding fragment thereof of the invention. Preferably the homologous nucleic acid molecule comprises a nucleotide sequence that is at least about 90% identical to the nucleotide sequence that encodes the GSK3β polypeptide or antibody or antigen-binding fragment thereof. More preferably, the nucleotide sequence is at least about 95% identical, at least about 97% identical, at least about 98% identical, or at least about 99% identical to a nucleotide sequence that encodes a GSK3β polypeptide or an antibody or antigen-binding fragment thereof of the invention. The homology can be calculated using various, publicly available software tools well known to one of ordinary skill in the art. Exemplary tools include the BLAST system available from the website of the National Center for Biotechnology Information (NCBI) at the National Institutes of Health. Similarly, the amino acid sequence of a polypeptide useful in methods and compositions of the invention may be at least about 90% identical to the amino acid sequence of a GSK3β polypeptide. The amino acid sequence may be at least about 95% identical, at least about 97% identical, at least about 98% identical, or at least about 99% identical to an amino acid sequence of a GSK3β polypeptide of the invention.

One method of identifying highly homologous nucleotide sequences is via nucleic acid hybridization. Thus the invention also includes antibodies having phosphorylated GSK3β-binding properties (including but not limited to $Thr^{390}$-phosphorylated GSK3β polypeptide-binding properties or $Ser^{389}$-phosphorylated GSK3β polypeptide-binding properties) and other functional properties described herein, and includes additional GSK3β polypeptides that are encoded by nucleic acid molecules that hybridize under high stringency conditions to a nucleic acid that encodes an antibody or antigen-binding fragment thereof of the invention, or a GSK3β polypeptide of the invention, respectively. Identification of related sequences can also be achieved using polymerase chain reaction (PCR) and other amplification techniques suitable for cloning related nucleic acid sequences. Preferably, PCR primers are selected to amplify portions of a nucleic acid sequence of interest, such as a CDR.

The term "high stringency conditions" as used herein refers to parameters with which the art is familiar. Nucleic acid hybridization parameters may be found in references that compile such methods, e.g., *Molecular Cloning: A Laboratory Manual*, J. Sambrook, et al., eds., Second Edition, Gold Spring Harbor Laboratory Press, Cold Spring Harbor, N.Y., 1989, or *Current Protocols in Molecular Biology*, P. M. Ausubel, et al., eds., John Wiley & Sons, Inc., New York. One example of high-stringency conditions is hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA), SSC is 0.15M sodium chloride/0.015M sodium citrate, pH7; SDS is sodium dodecyl sulphate; and EDTA is ethylenediaminetetracetic acid. After hybridization, a membrane upon which the nucleic acid is transferred is washed, for example, in 2×SSC at room temperature and then at 0.1-0.5×SSC/0.1×SDS at temperatures up to 68° C.

Detectable Labels

Polypeptides and/or nucleic acids of the invention may be detectably labeled for use in methods and/or compositions of the invention. A wide variety of detectable labels are available for use in methods of the invention and may include labels that provide direct detection (e.g., fluorescence, colorimetric, or optical, etc.) or indirect detection (e.g., enzyme-generated luminescence, epitope tag such as the FLAG epitope, enzyme tag such as horseradish peroxidase, labeled antibody, etc.). A variety of methods may be used to detect a detectable label depending on the nature of the label and other assay components. Labels may be directly detected through optical or electron density, radioactive emissions, nonradiative energy transfers, etc. or indirectly detected with antibody conjugates, strepavidin-biotin conjugates, etc. Methods for using and detecting labels are well known to those of ordinary skill in the art. Methods of the invention may be used for in vivo, in vitro, and/or ex vivo imaging, including but not limited to real-time imaging. The presence of a labeled antibody in a subject can be detected by in vivo, ex vivo, or in vitro imaging using standard methods. Examples of detection methods include, but are not limited to, MRI, functional MRI, X-Ray detection, PET, CT imaging, immunohistochemistry. Western blot of tissues or cells, or by any other suitable detection method.

The term "detestable label" as used here means a molecule preferably selected from, but not limited to, fluorescent, enzyme, radioactive, metallic, biotin, chemiluminescent, and bioluminescent molecules. As used herein, a detectable label may be a colorimetric label, e.g., a chromophore molecule. In some aspects of the invention, a polypeptide or an antibody may be detectably labeled with a single or with two or more of the detectable labels set forth herein, or other art-known detectable labels.

Radioactive or isotopic labels may be, for example, $^{14}C$, $^{3}H$, $^{35}S$, $^{125}I$, and $^{32}P$. Fluorescent labels may be any compound that emits an electromagnetic radiation, preferably visible light, resulting from the absorption of incident radiation and persisting as long as the stimulating radiation is continued.

Examples of fluorescent labels that may be used on polypeptides and/or antibodies of the invention and in methods of the invention include but are not limited to 2,4-dinitrophenyl, acridine, cascade blue, rhodamine, 4-benzoylphenyl, 7-nitrobenz-2-oxa-1,3-diazole, 4,4-difluoro-4-bora-3a,4a-diaza-3-indacene and fluorescamine. Absorbance-based labels may be molecules that are detectable by the level of absorption of various electromagnetic radiation. Such molecules may be, for example, the fluorescent labels indicated above.

Chemiluminescent labels in this invention refer to compounds that emit light as a result of a non-enzymatic chemical reaction. Methods of the invention may also include the use of a luminescent detestable diagnostic molecule such as enhanced green fluorescent protein (EGFP), luciferase (Luc), or another detectable expression product.

Enzymatic methods for detection may be used including the use of alkaline phosphatase and peroxidase. Additional enzymes may also be used for detection in methods and kits of the invention.

As used herein, fluorophores include, but are not limited to amine-reactive fluorophores that cover the entire visible and near-infrared spectrum. Examples of such fluorophores include, but are not limited to, 4-methylumbelliferyl phosphate, fluorescein isothiocyanate (FITC), tetramethylrhodamine isothiocyanate (TRITC), BODIPY dyes; Oregon Green, rhodamine green dyes; the red-fluorescent Rhodamine Red-X, Texas Red dyes; and the UV light-excitable Cascade Blue, Cascade Yellow, Marina Blue, Pacific Blue and AMCA-X fluorophores. Fluorophores may also include non-fluorescent dyes used in fluorescence resonance energy transfer (FRET).

A labeled polypeptide or antibody of the invention can be prepared from standard moieties known in the art. As is recognized by one of ordinary skill in the art, the labeling process for preparing a detectable labeled polypeptide, antibody, or fragment thereof may vary according to the molecular structure of the polypeptide or antibody and the detectable label. Methods of labeling polypeptides and/or antibodies with one or more types of detectable labels are routinely used and are well understood by those of ordinary skill in the art.

In some embodiments, it is contemplated that one may wish to first derivative a polypeptide or antibody, and then attach the detectable label to the derivatized product. Suitable cross-linking agents for use in this manner include, for example, SPDP (N-succinimidyl-3-(2-pyridyldithio)propionate), and SMPT, 4-succinimidyl-oxycarbonyl-methyl-(2-pyridyldithio)toluene. In some embodiments, a radionuclide may be coupled to a polypeptide, antibody, or antigen-binding fragment thereof by chelation.

Modulation of GSK3β Activity

Compositions (e.g., phosphorylated polypeptides, antibodies to phosphorylated GSK3β and derivatives/conjugates thereof, etc.) of the present invention have therapeutic utilities. For example, these molecules can be administered to cells in culture, e.g., in vitro or ex vivo, or administered to a subject in vivo. In some embodiments the polypeptides of the invention can be used to reduce activity of GSK3β activity in a cell in some embodiments contacting a cell with a GSK3β polypeptide comprising a phosphorylated residue that corresponds to $Thr^{390}$ in a full-length, wild-type human protein or $Ser^{389}$ in a full-length wild-type mouse polypeptide, results in a decrease in the activity of GSK3β. Polypeptides and compounds of the invention may be contacted with cells and/or administered to subjects in compositions. Compositions of the invention may include a carrier. In some embodiments, the carrier may be a pharmaceutically acceptable carrier.

Aspects of the invention relate to the discovery that GSK3β is phosphorylated at a C-terminal residue by p38/MAPK. As described herein in the example section, p38/MAPK phosphorylates GSK3β at a C-terminal residue that corresponds to $Thr^{390}$ in a full-length, wild-type human protein or $Ser^{389}$ in a full-length wild-type mouse polypeptide, resulting in a decrease in the activity of GSK3β. In some embodiments, methods of the invention relate to contacting a cell with a compound that phosphorylates GSK3β at a residue that corresponds to $Thr^{390}$ in a full-length, wild-type human protein or $Ser^{389}$ in a full-length wild-type mouse polypeptide. In order to regulate the activity of GSK3β in vitro or in vivo. In some embodiments a cell that is contacted with a GSK3β polypeptide has an endogenous GSK3β polypeptide present. The endogenous GSK3β polypeptide may or may not be phosphorylated. In some embodiments, in order to reduce the activity of GSK3β, a cell is contacted with both a phosphorylated GSK3β polypeptide comprising a phosphorylated residue corresponding to $Thr^{390}$ in a full-length, wild-type human protein or $Ser^{389}$ in a full-length wild-type mouse polypeptide, as well as a compound that results in phosphorylation of GSK3β at a residue that corresponds to $Thr^{390}$ in a full-length, wild-type human protein or $Ser^{389}$ in a full-length wild-type mouse polypeptide.

In some embodiments the compound that results in phosphorylation of GSK3β modulates the expression or activity of the p38 MAPK signaling pathway in the cell. p38 is a component of a mitogen-activated protein kinase (MAPK) signaling cascade that responds to cellular conditions such as stress, cytokines, and/or growth factors. Upstream factors in the p38/MAPK signaling pathway that respond to stimuli include, but are not limited to, MAPKKK molecules including MLK3, TAK1, MEKK4 and ASK1. Downstream of these factors are the MAPKK molecules including MKK3/6. Downstream of these factors are the MAPK, molecules such as p38 proteins, which influence further downstream factors such as transcription factors. It should be appreciated that a step or molecule in the p38 signaling pathway can be targeted in order to influence p38 activity (e.g., MLK3, TAK1, MEKK4, ASK1, MKK3/6, p38α/β/γ/δ etc.). In some non-limiting embodiments, activity of the p38 signaling pathway is upregulated through the use of inflammatory cytokines such as TNFalpha, IL-1 and IL-12, growth factors such as CSF-1, histamine, T cell receptors, LPS and other TLR-ligands, or Dectin-ligands. In some embodiments, activity of the p38 signaling pathway is upregulated through stress such as DNA damage. In certain embodiments DNA damage can be caused by a procedure, examples of which include, but are not limited to: exposure to UV, gamma-irradiation, X-ray, or chemotherapeutic drugs. Other non-limiting examples of sources of cellular stress include oxidative stress, osmotic shock and heat, which may be non-limiting examples of procedures that modulate phosphorylation of GSK3β. It should be appreciated that methods of modulating the p38 signaling pathway are compatible with methods of the invention. In some embodiments of the invention, a compound that results in phosphorylation of GSK3β is p38.

In some embodiments, aspects of the invention relate to methods for increasing the activity of GSK3β in a cell through reduction of phosphorylation of a GSK3β residue that corresponds to $Thr^{390}$ in a full-length, wild-type human protein or $Ser^{389}$ in a full-length wild-type mouse polypeptide. In some embodiments a cell is contacted with a compound that results in a decrease in levels of phosphorylation of GSK3β. In some embodiments the compound that results in a decrease in levels of phosphorylation of GSK3β modulates expression or activity of one or more components of the p38 MAPK signaling pathway. In some embodiments the compound that results in a decrease in levels of phosphorylation of GSK3β inhibits p38 MAPK. It should be appreciated that a p38 MAPK inhibitor may inhibit expression (e.g., transcription, translation, and/or stability) of p38 MAPK and/or p38 MAPK activity. An inhibitor may be a specific p38 MAPK inhibitor or a non-specific inhibitor (e.g., a non-specific kinase inhibitor) or a multi-target inhibitor that inhibits p38 MAPK. An inhibitor may be a small molecule, an aptamer, an antibody, an RNAi, an antisense RNA, or any other suitable molecule, or any combination thereof. In some embodiments, a procedure such as one listed above herein may be used alone or in conjunction with a compound to modulate phosphorylation of GSK3β.

It should be appreciated that expression levels of any of the molecules discussed herein, including GSK3β, may be detected using any suitable director indirect assay for detecting expression in a sample. In certain embodiments, protein expression may be detected by a Western blot. In some embodiments a phospho-specific antibody is used, protein levels can also be determined by an ELISA assay. In some embodiments the detection of a modified or mutated form of a protein may be used to indicate the activity level of a protein. For example the detection of a phosphorylation event on a specific residue of a protein may be correlated with an increase or decrease in the activity of that protein and in some embodiments an increase or decrease in the signaling activity of a pathway involving that protein. In some embodiments, wherein the molecule is a kinase, kinase activity may be detected using a kinase assay. In some embodiments activation of a protein can be measured by detection of levels of expression, activity, phosphorylation, etc., of a substrate of the molecule. It should be appreciated that an increase in activity of a molecule could represent a change in activity level of 1%, 2%, 5%, 10%, 20%, 25%, 30%, 50%, 75%, 100%, 200%, up to 500%, and any value in between, relative to the wild-type activity level of the molecule. Similarly a decrease in activity of a molecule could be a change in activity level of 1%, 2%, 5%, 10%, 20%, 25%, 30%, 50%, 75%, up to 100%, and any value in between, relative to the wild-type activity level of the molecule.

Treatment

According so aspects of the invention, contacting a cell with a phosphorylated GSK3β polypeptide, and/or with a compound and/or procedure that modulates GSK3β phosphorylation can occur in vivo or in vitro. In some embodiments contacting a cell occurs in vivo and is a method of treating a disease, disorder or condition that is associated with elevated or reduced GSK3β activity. As used herein "disorder" refers to any pathological condition associated with elevated or reduced GSK3β activity. In some embodiments the disorder or condition associated with elevated GSK3β activity is a neurological disorder or condition. Some non-limiting examples of neurological disorders or conditions include stroke, cerebral ischemia, spinal cord trauma, head trauma, perinatal hypoxia, hypoglycemic neuronal damage, dementia (including AIDS-induced dementia), Alzheimer's disease, Huntington's Chorea, amyotrophic lateral sclerosis, multiple sclerosis, ocular damage, cognitive disorders, idiopathic and drug-induced Parkinson's disease, amyotrophic lateral sclerosis, tremors, epilepsy, convulsions, migraine (including migraine headache), psychosis, schizophrenia, mood disorders (including depression, mania, bipolar disorders), trigeminal neuralgia, brain edema, pain (including acute and chronic pain states, severe pain, intractable pain, neuropathic pain, and post-traumatic pain), tardive dyskinesia, motor neuron disease, spinal muscular atrophy, progressive supranuclear palsy, and multiple sclerosis. In some embodiments the disease or condition associated with reduced GSK3β activity is cancer or diabetes.

As used herein, the term treat, treated, or treating when used with respect to a disorder refers to a prophylactic treatment that increases the resistance of a subject to development of the disease or, in other words, decreases the likelihood that the subject will develop the disease as well as a treatment after the subject has developed the disease in order to fight the disease or prevent the disease from becoming worse. The term "treatment" embraces the prevention of a disorder or condition, and the inhibition and/or amelioration of pre-existing disorders and conditions. A subject may receive treatment because the subject has been determined to be as risk of developing a disorder or condition, or alternatively, the subject may have such a disorder or condition. Thus, a treatment may prevent, reduce or eliminate a disorder or condition altogether or prevent it from becoming worse.

As used herein, the term "subject" refers to a human or non-human mammal or animal non-human mammals include livestock animals, companion animals, laboratory animals, and non-human primates. Non-human subjects also specifically include, without limitation, chickens, horses, cows, pigs, goats, dogs, cats, guinea pigs, hamsters, mink, and rabbits. In some embodiments of the invention, a subject is a patient. As used herein, a "patient" refers to a subject who is under the care of a physician or other health care worker, including someone who has consulted with, received advice from or received a prescription or other recommendation from a physician or other health care worker.

As used herein, the term "cancer" refers to an uncontrolled growth of sells that may interfere with the normal functioning of the bodily organs and systems, and includes both primary and metastatic tumors. Primary tumors or cancers that migrate from their original location and seed vital organs can eventually lead to the death of the subject through the functional deterioration of the affected organs. A metastasis is a cancer cell or group of cancer cells, distinct from the primary tumor location, resulting from the dissemination of cancer cells from the primary tumor to other parts of the body. Metastases may eventually result in death of a subject.

As used herein, the term "cancer" includes, but is not limited to, the following types of cancer: breast cancer (including carcinoma in situ), biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chromic myelogenous leukemia, multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; mesothelioma, neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma; and medullar carcinoma; and renal cancer including adenocarcinoma and Wilms tumor. Non-limiting examples of precancerous conditions include dysplasia, premalignant lesions, adenomatous colon polyp, and carcinoma in-situ such as Ductal carcinoma in-situ (DCIS), etc. Other cancers that can be treated with methods of the invention will be known to those of ordinary skill in the art. In some embodiments of the invention, the cancer is melanoma. In certain embodiments the cancer is adenocarcinoma, in some embodiments the cancer is a solid tumor cancer. A cancer that may be treated or assayed using methods of the invention also may include breast cancer, lung cancer, prostate cancer, mesothelioma, etc.

Selecting Treatment

Described herein are methods for assessing effectiveness of a composition such as a phosphorylated GSK3β polypeptide or a compound that modulates the level of phosphorylation of GSK3β for treatment of a disease or condition, in some embodiments a cell will be contacted with a phosphorylated GSK3β polypeptide and/or a compound that modulates the level of phosphorylation of GSK3β, and the effect of this treatment on the cell will be monitored. In some embodiments the viability of the cell (e.g., a neuronal cell or a cancer cell) will be monitored and will be indicative of the effectiveness of the treatment. In some embodiments, the cell is taken from a subject who has a neurological disease or disorder or a subject who has cancer, in certain embodiments, sample sources for the cell may include tissues, including but not limited to, lymph tissues; body fluids (e.g., blood, lymph fluid, etc.), cultured cells, cell lines; histological slides; tissue embedded in paraffin; etc. The term "tissue" as used herein refers to both localized and disseminated cell populations including, but not limited tot brain, heart, serum, breast, colon, bladder, epidermis, skin, uterus, prostate, stomach, testis, ovary, pancreas, pituitary gland, adrenal gland, thyroid gland, salivary gland, mammary gland, kidney, liver, intestine, spleen, thymus, bone marrow, trachea, and lung. Invasive and non-invasive techniques can be used to obtain such samples and are well documented in the art. A control cell sample may include a cell, a tissue, or may be a lysate of either. In some embodiments, a control sample may be a sample that is a cell or from a subject that is free of a neurological disease or disorder or cancer and/or free of a precancerous condition. In some embodiments, a control sample may be a sample that is a cell or from a subject that has a neurological disease or disorder or cancer or a precancerous condition. It will be understood that controls according to the invention may be, in addition to predetermined values, samples of materials tested in parallel with the experimental materials. Examples include samples from control populations or control samples generated through manufacture to be tested in parallel with the experimental samples.

In some embodiments, factors such as the level of cell growth, proliferation, and/or viability of cells in a sample may be measured. In some embodiments, measurements of cell growth or proliferation can be correlated to levels of cell viability, whereas in other embodiments, cell viability may be measured directly. These factors can be determined in a number of ways when carrying out the various methods of the invention. In one measurement, the level of cell growth, proliferation, or viability of cells in a test sample is measured in relation to a control sample. In some embodiments, a control sample and a test sample may be taken from the sense subject. The test sample may be treated with a composition comprising a phosphorylated GSK3β polypeptide and/or a compound that modulates phosphorylation of GSK3β. In some embodiments the control sample may be treated with either a composition comprising a phosphorylated GSK3β polypeptide or a compound that modulates phosphorylation of GSK3β, or with neither of these. The control and test samples may then be compared for the levels of such characteristics as cell growth, cell proliferation, and/or cell viability of cells in the sample, using art-known methods.

In some embodiments the cell is from a subject who has a neurological disease or disorder and the treatment is intended to increase cell survival. In this embodiment if the test sample shows increased cell growth, and/or proliferation and/or viability, relative to the control sample, then this would be interpreted to mean that cells in the test sample respond to treatment with a phosphorylated GSK3β polypeptide and/or a compound that modulates phosphorylation of GSK3β.

In some embodiments the cell is from a subject who has cancer and the treatment with a compound that modulates phosphorylation of GSK3β is intended to reduce cell survival. In this embodiment if the test sample shows decreased cell growth, and/or proliferation and/or viability, relative to the control sample, then this would be interpreted to mean that cells in the test sample, respond to treatment with a compound that modulates phosphorylation of GSK3β.

In some embodiments, a test sample and a control sample may include cells from different disorders. In some embodiments, a control sample may be a cell from a type of disorder that is known to respond to treatment with a phosphorylated GSK3β polypeptide and/or a compound that modulates phosphorylation of GSK3β. In such embodiments, if the test sample responds similarly to the control sample, then the test sample would be interpreted as responding to treatment. In other embodiments, a control sample may be a cell from a type of disorder that is known not to respond so treatment with a phosphorylated GSK3β polypeptide and/or a compound that modulates phosphorylation of GSK3β. In such embodiments, if the test sample responds similarly so the control sample then the test sample would be interpreted as not responding to treatment. It will be understood that the interpretation of a comparison between a test sample and a control sample will depend on the nature of both samples.

One possible measurement of the level of cell growth, proliferation, and/or viability of cells in a sample is a measurement of absolute levels of cell growth, proliferation, and/or viability. Another measurement of the level of cell growth, proliferation, or viability of cells in a sample is a measurement of the change in the level of cell growth, proliferation, or viability of cells over time. This may be expressed in an absolute amount or may be expressed in terms of a percentage increase or decrease over time. Methods and assays of the invention may be combined with other methods and assays in determining the level of cell growth, proliferation, and/or viability of cells in a sample, and in determining an optimal treatment strategy for a patient.

In some embodiments, a control value may be a predetermined value, which can take a variety of forms. It can be a single cut-off value, such as a median or mean. It can be established based upon comparative groups, such as in groups having normal amounts of cell growth, proliferation, and/or viability, and groups having abnormal amounts of cell growth, viability, and/or proliferation. For example, in some embodiments a control sample that is taken from a subject with a disorder and is not treated with a phosphorylated GSK3β polypeptide and/or a compound that modulates phosphorylation of GSK3β may be considered to have normal levels of cell growth, viability, and proliferation for a cancer cell. In such embodiments, a test sample that is taken from the same subject and treated with a phosphorylated GSK3β polypeptide and/or a compound that modulates phosphorylation of GSK3β may be considered to have abnormal levels of cell growth, viability, and/or proliferation.

In another embodiment, a cell from a subject who does not have a disorder may be considered to have normal levels of cell growth, viability, and proliferation. In this embodiment, a cell taken from a subject who has a disorder, and not treated with a phosphorylated GSK3β polypeptide and/or a compound that modulates phosphorylation, may be considered to have abnormal levels of cell growth, viability, and/or proliferation, whereas a cell taken from the same subject and treated with a phosphorylated GSK3β polypeptide and/or a compound that modulates phosphorylation may be found to have levels of cell growth, viability, and/or proliferation that approach the normal level, which in such embodiments, would be the levels for a cell from a subject who does not have a disorder.

Based at least in part on results of hi vitro methods discussed herein, a predetermined value can be arranged. For example, test samples and the subjects from which the samples were extracted, are divided equally (or unequally) into groups, such as a low-response group, a medium-response group and a high-response group, where response refers to response of the sample from each group to treatment with a phosphorylated GSK3β polypeptide and/or a compound that modulates phosphorylation using methods described herein. Test samples and subjects may be divided into quadrants or quintiles, the lowest quadrant or quintile being individuals with the lowest response and the highest quadrant or quintile being individuals with the highest response. Individuals with the highest level of response to the treatment would be considered the most likely to respond to the treatment. However individuals in low and medium response groups may also be found to respond to the treatment.

The predetermined value, of course, will depend upon the particular population selected. For example, an apparently healthy population will have a different 'normal' range than will a population that is known to have a disorder. In addition, values may be different for different disorders, or for different populations or individuals. Accordingly, the predetermined value selected may take into account the category in which an individual or cell falls. Appropriate ranges and categories can be selected with no more than routine experimentation by those of ordinary skill in the art. As used herein, "abnormal" means not normal as compared to a control. By abnormally high or low it is meant high or low relative to a selected control.

It is also possible to use measurements of cell growth, proliferation, and/or viability to monitor changes in the levels of these factors over time in a cell sample. For example, in some embodiments it is expected that treatment of a cancer cell with a compound that modulates GSK3β phosphorylation will lead to a decrease in levels of cell growth, proliferation, and/or viability relative to a control sample of a cancer cell that is not treated with a phosphorylated GSK3β polypeptide and/or a compound that modulates GSK3β phosphorylation. In some embodiments it is expected that treatment of a neuronal cell with a phosphorylated GSK3β polypeptide and/or a compound that modulates GSK3β phosphorylation will lead to an increase in levels of cell growth, proliferation, and/or viability relative to a control sample of a neuronal cell that is not treated with a phosphorylated GSK3β polypeptide and/or a compound that modulates GSK3β phosphorylation. Accordingly, one can monitor levels of cell growth, proliferation, and/or viability over time to determine if there is a change in the levels of these factors in a subject or in a cell culture. In some embodiments, changes in levels of cell growth, proliferation, and/or viability greater than 0.1% may be considered to indicate effectiveness of the treatment on the levels of these factors. In some embodiments, the reduction in levels of cell growth, viability and/or proliferation, which indicate effectiveness of the treatment on these factors, is a redaction greater than 0.2%, greater than 0.5%, greater than 1.0%, 2.0%, 3.0%, 4.0%, 5.0%, 7.0%, 10%, 15%, 20%, 25%, 30%, 40%, 50%, 60%, 70%, 80%, 90%, 95%, 99%, or 100%, including each percentage in between these values. Increases or decreases in the levels of cell growth, proliferation, and/or viability of cells over time may indicate a change in responsiveness to treatment in a sample or subject. To make a determination of a change in responsiveness to treatment in a subject over time, multiple samples may be obtained from the subject at different times and the samples tested for levels of cell growth, proliferation, and/or viability of cells. Resulting values may be compared to each other as a measure of change over time.

Methods of selecting a treatment may be useful to assess and/or adjust treatment of subjects already receiving a drug or therapy (e.g., radiation treatment or surgery) for treating a disorder or condition. Based on the determination of the response of a cell to administration of s phosphorylated GSK3β polypeptide and/or a compound that modulates GSK3β phosphorylation, it may be appropriate to alter a therapeutic regimen for s subject. For example, determination that a cell responds to administration of a phosphorylated GSK3β polypeptide and/or a compound that modulates GSK3β phosphorylation in a subject who has received or is receiving a treatment for a neurological disorder, cancer or precancerous-condition treatment may indicate that the treatment regimen should be adjusted (e.g., the dose or frequency of dosing, increased, new treatment initiated, etc.). For example, a reduction in cancer cell viability after contact with a compound that modulates GSK3β phosphorylation indicates that the cancer is responsive to the treatment and that the treatment may be useful to treat that cancer. Similarly, an increase in neuronal cell viability in a subject who has a neurological disorder after contact with a GSK3β polypeptide and/or a compound that modulates GSK3β phosphorylation indicates that the neurological disorder is responsive to the treatment and that the treatment may be useful to treat that neurological disorder. Different parameters can be assessed to determine appropriate optimized treatment regimens for a given patient's disorder.

Administration

According to aspects of the invention, polypeptides, compounds, and compositions are administered in effective amounts. In a subject who has a disorder that is associated with elevated GSK3β activity, an effective amount of a composition is the amount effective to decrease the level of GSK3β activity in the subject. In a subject who has a disorder that is associated with reduced GSK3β activity, an effective amount of a composition is the amount effective to increase the level of GSK3β activity in the subject. Phosphorylated GSK3β polypeptides associated with the invention and/or compositions that increase phosphorylation of GSK3β may be administered in effective amounts to prevent and/or treat disorders or conditions that are associated with elevated GSK3β activity such as neurological disorders or conditions. Compositions that result in decreased phosphorylation of GSK3β may be administered in effective amounts to prevent and/or treat disorders or conditions that are associated with reduced GSK3β activity such as cancer. Typically an effective amount of a composition for treatment of a disorder or condition will be determined in clinical trials, establishing an effective dose for a test population versus a control population in a blind study. In some embodiments, an effective amount will be an amount that results in a desired response, e.g., an amount that diminishes or eliminates phosphorylation and/or activity of GSK3β. Thus, an effective amount may be the amount that when administered increases or decreases the phosphorylation and/or activity of GSK3β from the amount that would occur in the subject or tissue without the administration of the composition of the invention. In the case of treating s particular disease or condition the desired response is inhibiting the progression of the disease or condition. This may involve only slowing the progression of the disease temporarily, although more preferably, it involves halting the progression of the disease permanently. This can be monitored by routine diagnostic methods known to one of ordinary skill in the art for any particular disease. The desired response to treatment of the disease or condition also can be delaying the onset or even preventing the onset of the disease or condition.

Effective amounts of therapeutic compounds such as an effective amount of a phosphorylated GSK3β polypeptide and/or an effective amount of a composition that modulates GSK3β phosphorylation may also be determined by assessing physiological effects of administration on a cell or subject, such as a decrease of disease symptoms following administration. Other assays will be known to one of ordinary skill in the art and can be employed for measuring the level of the response to a treatment. The amount of a treatment may be varied for example, by increasing or decreasing the amount of a therapeutic composition, by changing the therapeutic composition administered, by changing the route of administration, by changing the dosage timing and so on. The effective amount will vary with the particular condition being treated, the age and physical condition of the subject being treated, the severity of the condition, the duration of the treatment, the nature of the concurrent therapy (if any), the specific route of administration, and the like factors within the knowledge and expertise of the health practitioner. For example, an effective amount may depend upon the degree to which an individual has abnormally low or high levels of phosphorylation of GSK3β polypeptide.

Effective amounts will also depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of a composition according to the invention (alone or in combination with other therapeutic agents) be used, that is, the highest sale dose according to sound medical judgment. It will be understood by those of ordinary skill in the art, however, that a patient may insist upon a lower dose or tolerable dose for medical reasons, psychological reasons or for virtually any other reasons.

A pharmaceutical compound or composition dosage may be adjusted by the individual physician or veterinarian, particularly in the event of any complication. A therapeutically effective amount typically varies from 0.01 mg/kg so about 1000 mg/kg, preferably from about 0.5 mg/kg to about 200 mg/kg, and most preferably from about 0.2 mg/kg to about 20 mg/kg, in one or more dose administrations daily, for one or more days.

The absolute amount will depend upon a variety of factors, including the material selected for administration, whether the administration is in single or multiple doses, and individual subject parameters including age, physical condition, size, weight, and the stage of the disease or condition. These factors are well known to those of ordinary skill in the art and can be addressed with no more than routine experimentation.

Pharmaceutical compounds or compositions of the invention may be administered alone, in combination with each other, and/or in combination with other drug therapies, or other treatment regimens that are administered to subjects with disorders associated with the invention.

A pharmaceutical compositions used in the foregoing methods preferably are sterile and contain an effective amount of a therapeutic compound that will modulate the level of GSK3β activity for a level that produces the desired response in a unit of weight or volume suitable for administration to a patient.

The doses of pharmaceutical compounds or compositions of the invention administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localised delivery route) may be employed to the extent that patient tolerance permits.

Various modes of administration will be known to one of ordinary skill in the art which effectively deliver a pharmaceutical composition of the invention (e.g., a phosphorylated GSK3β polypeptide and/or a composition that modulates phosphorylation of GSK3β) to a desired tissue, cell or bodily fluid. Methods for administering a pharmaceutical compound or composition of the invention may be topical, intravenous, oral, intracavity, intrathecal, intrasynovial, buccal, sublingual, intranasal, transdermal, intravitreal, subcutaneous, intramuscular and intradermal administration. The invention is not limited by the particular modes of administration disclosed herein. Standard references in the art (e.g., *Remington's Pharmaceutical Sciences,* 18th edition, 1990) provide modes of administration and formulations for delivery of various pharmaceutical preparations and formulations in pharmaceutical carriers. Other protocols which are useful for the administration of a compound or composition of the invention will be known to one of ordinary skill in the art, in which the dose amount, schedule of administration, sites of administration, mode of administration (e.g., intra-organ) and the like vary from those presented herein.

Administration of a phosphorylated GSK3β polypeptide, or other pharmaceutical compound or composition of the invention to mammals other than humans, e.g., for testing purposes or veterinary therapeutic purposes, is carried out under substantially the same conditions as described above. It will be understood by one of ordinary skill in the art that this invention is applicable to both human and animal diseases which can be treated by a phosphorylated GSK3β polypeptide, or other pharmaceutical compound of the invention.

When administered, the pharmaceutical preparations of the invention axe applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. Preferred components of the composition are described above in conjunction with the description of the GSK3β polypeptides and compositions of the invention that modulate phosphorylation of GSK3β.

A phosphorylated GSK3β polypeptide, or other therapeutic compound of the invention may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the phosphorylated GSK3β polypeptide, or other therapeutic compound of the invention, and with each other, in a manner such that there is no interaction which would substantially impair the desired pharmaceutical efficacy.

A pharmaceutical composition of the invention may contain suitable buffering agents, as described above, including: acetate, phosphate, citrate, glycine, borate, carbonate, bicarbonate, hydroxide (and other bases) and pharmaceutically acceptable salts of the foregoing compounds.

A pharmaceutical composition of the invention, also may contain, optionally, suitable preservatives, such as: benzalkonium chloride; chlorobutanol; parabens and thimerosal. The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration may comprise a phosphorylated GSK3β polypeptide, or other therapeutic compound of the invention. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water. Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in *Remington's Pharmaceutical Sciences*, Mack Publishing Co., Easton, Pa.

Screening

GSK3β polypeptides comprising a phosphorylated residue that corresponds to residue $Thr^{390}$ in a full-length, wild-type, human GSK3β amino acid sequence, or that corresponds to residue $Ser^{389}$ in a full-length, wild-type, mouse GSK3β amino acid sequence of the invention may also be useful in methods of screening for candidate agents that modulate levels of phosphorylated GSK3β polypeptides in cells, tissues, and/or subjects. Methods can include contacting a GSK3β polypeptide comprising a phosphorylated residue that corresponds to residue $Thr^{390}$ in a full-length, wild-type, human GSK3β amino acid sequence, or that corresponds to residue $Ser^{389}$ in a full-length, wild-type, mouse GSK3β amino acid sequence, with p38 MAPK and a putative modulating compound under suitable conditions for phosphorylation of the residue that corresponds to residue $Thr^{390}$ in a full-length, wild-type, human GSK3β amino acid sequence, or that corresponds to residue $Ser^{389}$ in a full-length, wild-type, mouse GSK3β amino acid sequence. Levels of phosphorylation of the $Thr^{390}$ or $Ser^{389}$ residue in the contacted polypeptide would then be determined and compared to a control polypeptide that is not contacted with the putative modulating compound. An increase in the level of phosphorylation of the GSK3β polypeptide in the contacted polypeptide relative to the control is indicative of a compound capable of increasing the level of phosphorylation of the GSK3β polypeptide. An increase in the phosphorylation of the GSK3β polypeptide in a subject known to have a neurological disorder is indicative that the candidate agent/compound is capable of decreasing the level of GSK3β activity and may be useful to reduce and/or eliminate a neurological condition in cells, tissues, and/or subjects. A decrease in the phosphorylation of the GSK3β polypeptide in a subject known to have a cancer or precancerous condition is indicative that the candidate agent/compound is capable of increasing the level of GSK3β activity and may be useful to reduce and/or eliminate a cancer or precancerous condition in cells, tissues, and/or subjects.

The assay mixture comprises a putative modulating compound. The putative modulating compound is preferably an antibody, a small organic compound, or a polypeptide, and accordingly can be selected from combinatorial antibody libraries, combinatorial protein libraries, or small organic molecule libraries. Typically, a plurality of reaction mixtures are run in parallel with different compound concentrations to obtain a different response to the various concentrations. Typically, one of these concentrations serves as a negative control, i.e., at zero concentration of compound or at a concentration of compound below the limits of assay detection.

Candidate compounds encompass numerous chemical classes, although typically they are organic compounds, proteins or antibodies (and fragments thereof that bind antigen). In some preferred embodiments, the candidate compounds are small organic compounds, i.e., those having a molecular weight of more than 50 yet less than about 2500, preferably less than about 1000 and, more preferably, less than about 500. Candidate compounds comprise functional chemical groups necessary for structural interactions with polypeptides and/or nucleic acids, and typically include at least an amine, carbonyl, hydroxyl, or carboxyl group, preferably at least two of the functional chemical groups and more preferably at least three of the functional chemical groups. The candidate compounds can comprise cyclic carbon or heterocyclic structure and/or aromatic or polyaromatic structures substituted with one or more of the above-identified functional groups. Candidate compounds also can be biomolecules such as polypeptides, saccharides, fatty acids, sterols, isoprenoids, purines, pyrimidines, derivatives or structural analogs of the above, or combinations thereof and the like.

Candidate compounds are obtained from a wide variety of sources including libraries of synthetic or natural compounds, for example, numerous means are available for random and directed synthesis of a wide variety of organic compounds and biomolecules, including expression of randomized oligonucleotides, synthetic organic combinatorial libraries, phage display libraries of random or non-random polypeptides, combinatorial libraries of proteins or antibodies, and the like. Alternatively, libraries of natural compounds in the form of bacterial, fungal, plant, and animal extracts are available or readily produced. Additionally, natural and synthetically produced libraries and compounds can be readily be modified through conventional chemical, physical, and biochemical means. Further, known agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc., which may be used to facilitate optimal protein-protein and/or protein-agent binding. Such a reagent may also reduce non-specific or background interactions of the reaction components. Other reagents that improve the efficiency of the assay such as protease inhibitors, nuclease inhibitors, antimicrobial agents, and the like may also be used.

The order of addition of components, incubation temperature, time of incubation, and other parameters of the assay may be readily determined. Such experimentation merely involves optimization of the assay parameters, not the fundamental composition of the assay, incubation temperatures typically are between 4° C. and 40° C. Incubation times preferably are minimized to facilitate rapid, high throughput screening, and typically are between 0.1 and 10 hours. After incubation, the presence or absence of and/or the level of phosphorylation of GSK3β polypeptides described herein is detected by any convenient method available to the user. For example, the level of phosphorylation of GSK3β polypeptides can be determined through the measure of a detectable label using standard methods and as described herein.

The invention will be more fully understood by reference to the following examples. These examples, however, are merely intended to illustrate the embodiments of the invention and are not to be construed to limit the scope of the invention.

Kits

Also within the scope of the invention are kits that may include polypeptides, compounds, antibodies, and/or compositions of the invention and instructions for use. The kits can further contain at least one additional reagent, such as one or more additional polypeptides of the invention. In some embodiments kits of the invention may be useful for determining a treatment regimen for a disorder or condition such as a neurological disorder or a cancer. An example of such a kit may include a composition including one or more phosphorylated GSK3β polypeptide and/or one or more compounds for modulating phosphorylation of GSK3β, and instructions for use of the polypeptides and/or compounds tot determining whether the compositions can be used as a treatment regimen for a disorder such as a neurological disorder or a cancer. Kits of the invention may also be useful for treating a disorder such as a neurological disorder or a cancer. An example of such a kit may include one or more phosphorylated GSK3β polypeptides and/or one or more compounds for modulating phosphorylation of GSK3β, and instructions for use of a combination of the polypeptides and compounds for treating the disorder.

Kits containing polypeptides and/or compounds for modulating phosphorylation of GSK3β of the invention can be prepared for contacting a cell in vitro or in vivo. The components of the kits can be packaged either in aqueous medium or in lyophilized form.

A kit may comprise a carrier being compartmentalized to receive in close confinement therein one or more container means or series of container means such as test tubes, vials, flasks, bottles, syringes, or the like. A first of said container means or series of container means may contain one or more phosphorylated GSK3β polypeptides and/or one or more compounds for phosphorylation of GSK3β.

A kit of the invention can include a description of use of the polypeptides, antibodies, compounds and/or compositions for participation in any biological or chemical mechanism disclosed herein. Kits can further include a description of activity of the condition in treating the pathology, as opposed to the symptoms of the condition. That is, a kit can include a description of use of the polypeptides, antibodies, compounds, and/or compositions as discussed herein. A kit also can include instructions for use of a combination of two or more compositions of the invention, or instruction for use of a combination of a composition of the invention and one or more other compounds indicated for determining a treatment regimen for a disorder. Instructions also may be provided for administering the composition by any suitable technique as previously described.

The kits described herein may also contain one or more containers, which may contain a composition and other ingredients as previously described. The kits also may contain instructions for mixing, diluting, and/or administering or applying the compositions of the invention in some cases. The kits also can include other containers with one or more solvents, surfactants, preservative and/or diluents (e.g., normal saline (0.9% NaCl), or 5% dextrose) as well as containers for mixing, diluting or administering the components in a sample or to a subject in need of such treatment.

The compositions of the kit may be provided as any suitable form, for example, as liquid solutions or as dried powders. When the polypeptide, compound and/or composition provided is a dry powder, is may be reconstituted by the addition of a suitable solvent, which may also be provided. In embodiments where liquid forms of the composition are used, the liquid form may be concentrated or ready to use. The solvent will depend on the composition and the mode of use or administration. Suitable solvents for drug compositions are well known, for example as previously described, and are available in the literature. The solvent will depend on the composition and the mode of use or administration.

Figure 16:
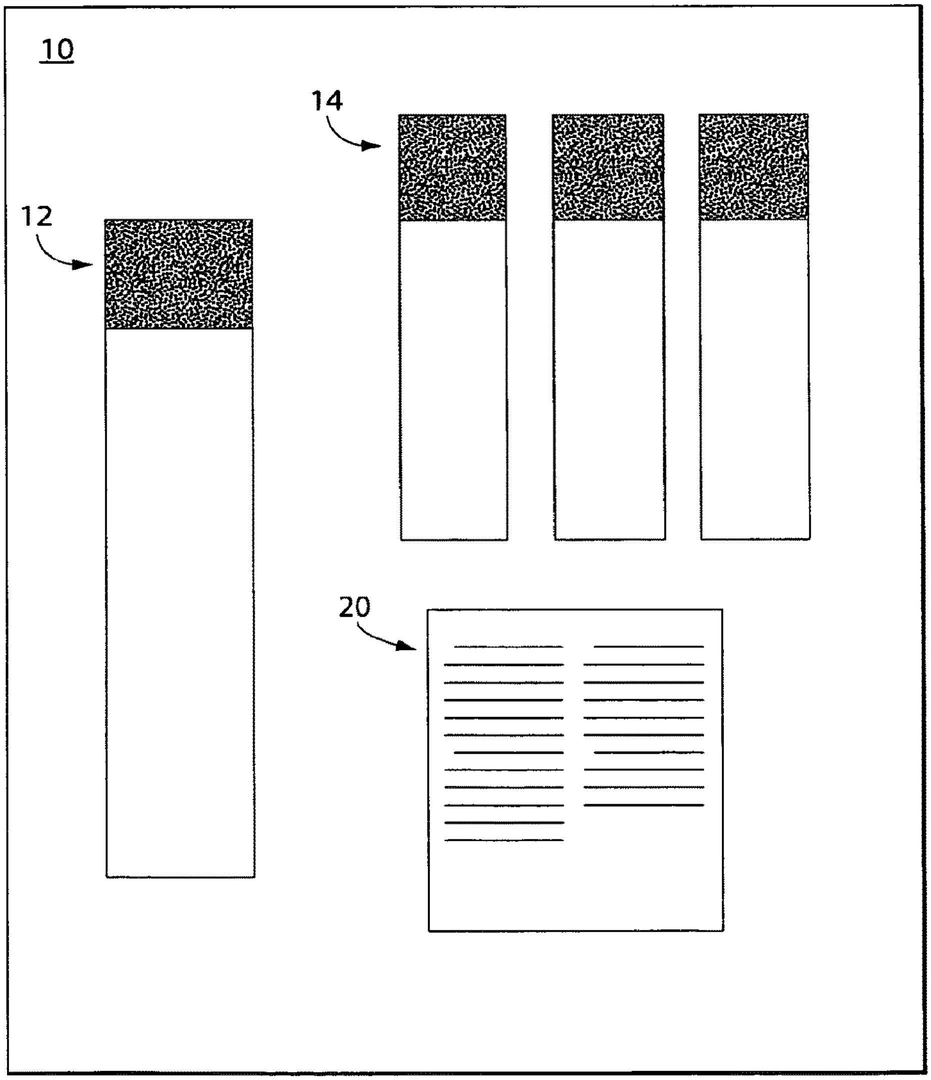
FIG. 16 represents a kit of the invention. The kit (10) shown in FIG. 16 includes a set of containers for housing a compounds (12) or (14) such as a phosphorylated GSK3β polypeptide or a composition that modulates phosphorylation of GSK3β. As well as instructions (20). Additional components may also be included in the kit.

An example of a kit useful according to the invention is shown in FIG. 16. The kit (10) shown in FIG. 16 includes a set of containers for housing compounds such as a phosphorylated GSK3β polypeptide (12) and other compounds (14) as well as instructions (20).

The present invention is further illustrated by the following Examples, which in no way should be construed as further limiting. The entire contents of all of the references (including: literature references, issued patents, published patent applications, and co-pending patent applications) cited throughout this application are hereby expressly incorporated herein by reference.

EXAMPLES

Example 1

Figure 5A:
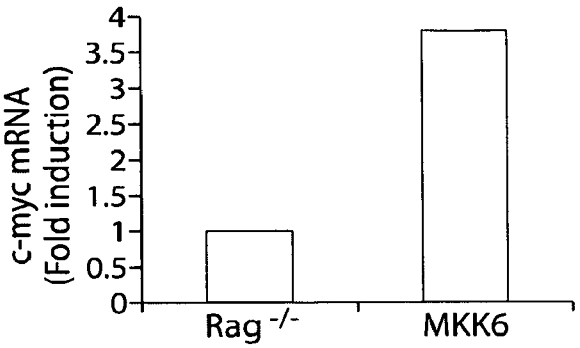
FIG. 5A-B present graphs showing that MKK6 transgenic thymocytes have increased expression of c-myc and lef mRNA. Gene expression was examined by Affymetrix gene chip analysis using mRNA isolated from MKK6 and $Rag^{-/-}$ thymocytes. Fold increase of MKK6 c-myc and lef mRNA relative to $Rag^{-/-}$ mRNA are shown.
Figure 5B:
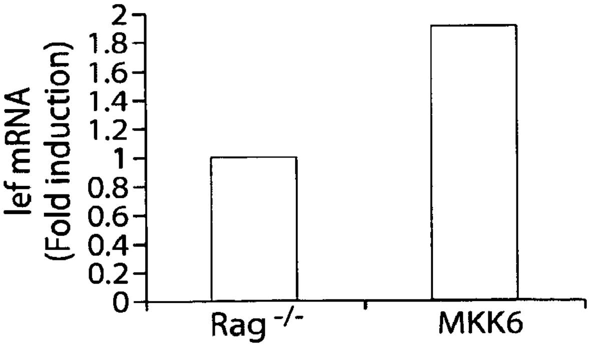

Phosphorylation by p38 MAP Kinase as an Alternative Pathway for GSK3β Inactivation Background The p38 MAPK is activated through phosphorylation primarily by MAPK Kinase (MKK)3 and MKK6 in response to cellular stress and cytokines. The p38 MAPK pathway functions in the control of differentiation, blockade of proliferation, and in induction of apoptosis (1). It is also activated in response to DNA double stranded breaks (DSBs) induced by ionizing irradiation or chemotherapeutic drugs, and participates in the induction of a G2/M cell cycle checkpoint (2, 3). p38 MAPK can also promote survival (4-6) by unknown mechanisms. During T cell receptor β (TCRβ) rearrangement, V(D)J-mediated DSBs also activate p38 MAPK in immature thymocytes at the double negative 3 (DN3) stage of development (7, 8). Expression of a constitutively active mutant of MKK6 [MKK6(Glu)] in thymocytes of transgenic mice (MKK6 transgenic mice) activates a p53-mediated G2/M phase cell cycle checkpoint (8). Like recombination-activating gene (Rag) deficiency, persistent activation of p38 MAPK interferes with differentiation of thymocytes beyond the DN3 stage. However, MKK6 transgenic thymocytes but not $Rag^{-/-}$ thymocytes survive and accumulate in vivo (8), suggesting that p38 MAPK may also provide a survival signal. Gene expression profile analysis comparing $Rag^{-/-}$ and MKK6 DN3 thymocytes revealed that the MKK6 DN3 thymocytes expressed more c-myc and lef (FIG. 5), two transcription factors associated with cell survival (9-11).

Methods

Mice

The MKK6(Glu) transgenic mice have been previously described (7, 8). Wildtype and $Rag^{-/-}$ mice were purchased from Jackson Laboratory (Bar Harbor, Me.). Procedures that involved mice were approved by institutional guidelines for animal care.

Plasmids pGEX-GST-GSK3β and pGEX-GST-GSK3β $T^{43}A$ both with the $K^{84}A$ kinase inactivating mutation were gifts from Dr. Mien-Chie Hung. Site directed mutagensis using the Transformer kit (Clontech, Mountain View, Calif.) was used to generate kinase inactive pGEX-GST-GSK3β-$T^{390}A$ and pGEX-GST-GSK3β-$T^{390}A/T^{43}A$ double mutants for use as substrates. The same site directed mutagensis technique was used to reverse the $K^{84}A$ mutation to generate kinase active pGEX-GST-GSK3β wildtype and mutant constructs for their use in GSK3β in vitro kinase assays. Wildtype human GSK3β was subcloned into the expression vector pEGZ-HA, a gift from Ingolf Berberich (University of Wurzburg, Wurzburg, Germany). Expression plasmids for wildtype p38 MAPK and constitutively active MKK6 (24) were also used. Mouse GSK-3β with a C-terminal 3XFLAG tag was subcloned into the mammalian expression vector pEF5/FRT/V5/D-TOPO (Invitrogen, Carlsbad, Calif.). The point mutation at $S^{389}$ (Ala) was introduced using the QuikchangeII XL mutagenesis kit (Stratagene, La Jolla, Calif.).

Cell Cultures

Thymocytes were isolated from wildtype, $Rag^{-/-}$ or MKK6(Glu) transgenic mice. 293T cells were transiently transfected with the indicated expression constructs using calcium phosphate. When specified, 293T cells were treated with SB203580 (5 μM) and Wortmanin (1 μM) (Calbiochem, San Diego, Calif.). Wildtype, $GSK3\alpha^{-/-}$ and GSK3β$^{-/-}$ ES cells (17), as well as WT and MKK3$^{-/-}$ MKK6$^{-/-}$ MEF (22) have been previously described, and were also treated with SB203580 as described above for the indicated periods of time. For in vivo inhibition of p38 MAPK, wildtype mice were intraperitoneally (i.p.) injected with SB203580 or vehicle alone, and after 18 hours brain and thymocytes were harvested to prepare whole cell lysates.

Reverse Transcription-Polymerase Chain Reaction

Total RNA was extracted using RNAeasy mini kit (Qiagen, Valencia, Calif.) and transcribed into cDNA using oligo(dT) primers and reverse transcriptase (Invitrogen, Carlsbad, Calif.) that was used to examine β-catenin expression by semiquantitative RT-PCR. The primers for β-catenin were (5'ACAGCACCTTCAGCACTCT3' (SEQ ID NO:91) and 5'AAGTTCTTGGCTATTACGACA) (SEQ ID NO:92) and the primers for Actin were 5'GTGGGGGCGCCCCAGCGCACCA3' (SEQ ID NO:93) and 5'CTT CCT TAA TGT CAC GCA CGA TTT C 3' (SEQ ID NO:94)

Western Blots and Immunoprecipitations

Whole cell extracts were prepared in Triton lysis buffer (TLB) as previously described (25, 26). Nuclear extracts were made from cells as previously described (27). Immunoprecipitations and Western blotting was performed as described in (8). Anti-Akt, anti-p38 MAPK, anti-Lef, anti-c-Myc and anti-Histone (Santa Cruz Biotechnology, Santa Cruz, Calif.), anti-GSK3β, anti-β-catenin, anti-phospho-p38 MAPK and antiphospho-$S^9$ (Cell Signaling, Beverly, Mass.) and Anti-Flag (Stratagene, La Jolla, Calif.) were used for Western blot analysis. The phospho-$S^{389}$ GSK3β antibody was made by Proteintech, Chicago, Ill., using N-C-ARIQAAA(phos-S)PPANATA (SEQ ID NO:87) for immunization. Anti-Akt, anti-p38 MAPK and Anti-GSK3β were used for immunoprecipitations. Anti-rabbit-HRP, anti-mouse-HRP (Jackson ImmunoResearch Laboratories, West Grove, Pa.) and anti-goat-HRP (Santa Cruz Biotechnology, Santa Cruz, Calif.) were used as secondary antibodies.

In Vitro Kinase Assays

In vitro kinase assays for p38 MAPK and ERK were performed as described in (28) with immunoprecipitated p38 MAPK, purified recombinant active p38 MAPK (Cell Signaling, Beverly, Mass.) and ERK (Cell Signaling, Beverly, Mass.) Kinase using 2 μg inactive wildtype GST-GSK3β, GST-GSK3β $T^{43}$A mutant, GST-GSK3β $T^{390}$A mutant and GST-GSK3β $T^{390}$A/$T^{43}$A double mutant (2 μg), GST-GSK3α (2 μg) (Cell Signaling, Beverly, Mass.) (boiled to inactivate) and GST-ATF2 fusion protein (2 μg) (Cell Signaling, Beverly, Mass.) as substrates in the presence or absence of SB203580 (2.5 μM) (Calbiochem, San Diego, Calif.). The reactions were terminated after 30 min at 30° C. by addition of SDS-PAGE sample buffer, separated by SDS-PAGE and transferred to nitrocellulose. Protein was visualized by staining with PonceauS and incorporated $^{32}$P was visualized by autoradiography. In specific experiments, whole cell extracts were first depleted of Akt prior to p38 MAPK immunoprecipitation by being pre-incubated with anti-Akt antibody prebound to protein A-Sepharose followed by one incubation with protein A-sepharose alone.

Active GST-GSK3β and GST-GSK3β-$T^{43}$A and GST-GSK3β-$T^{390}$ mutants were expressed and purified as described in (29). The specific activity of the wildtype and the mutants was determined using the GSM substrate peptide (Upstate, Lake Placid, N.Y.) and were as follows: GST-GSK3β (91 μmol/μg×min) and GST-GSK3β-$T^{43}$A (53 μmol/μg×min) and GST-GSK3β-$T^{390}$A (65 μmol/μg×min). In vitro GSK3β kinase assays were performed by incubating purified active wildtype GST-GSK3β or GST-GSK3β-$T^{43}$A and GST-GSK3β-$T^{390}$A mutants (400 ng) at 30° C. for 10 minutes in kinase buffer supplemented with 1 mM ATP containing [γ-$^{32}$P] ATP and GSM substrate peptide (62.5 μM) (Upstate, Lake Placid, N.Y.). Reactions were terminated by spotting onto P81 filters. Filters were washed extensively and counted in a scintillation counter. To examine the effect of p38 MAPK and Akt on GSK3β activity, purified active GSK3β or mutants were preincubated for 15 minutes at 30° C. with 500 ng recombinant active p38 MAPK or active Akt (Cell Signaling, Beverly, Mass.) prior to performing the GSK3β activity assay as described above.

For peptide inhibition assays, Phospho-$S^9$ (GRPRTTS($PO_3H_2$)FAE) (SEQ ID NO:95) (20). Phospho-$T^{380}$ (RIQAAAST($PO_3H_2$)PTN) (SEQ ID NO:7) and non-phospho-$T^{390}$ (RIQAAASTPTN) (SEQ ID NO:96) peptides were synthesized and purified by UVM protein Core Facility. In vitro kinase assays were performed with purified GST-GSK3β (400 ng) in Kinase buffer supplement with 1 mM ATP containing [γ-$^{32}$P] ATP and the indicated concentrations of GSM and inhibitory peptide.

Mass Spectrometric Analysis by LC-MS/MS

Kinase-inactive GSK3β was preincubated with or without active recombinant p38 MAPK for 30 min in the presence of ATP. The reaction mix was treated with an ammonium bicarbonate buffer containing DTT (10 mM) to reduce cysteines, incubated with iodoacetamide and digested with trypsin (40 ng/μl). Digestion was stopped with acetic acid (10%), centrifuged and the supernatant was used for analysis by electrospray ionization (ESI) liquid chromatography-mass spectrometry (LC-MS). A fused-silica microcapillary LC column (12 cm×75 μm id) packed with C18 reversed phase resin (Magic C18AQ, 5-μm particle size, 20-nm pore size, Michrom Bioresources, Auburn, Calif.) was used with nanospray ESI. The nanospray-ESI was fitted onto a linear quadrupole ion trap (LTQ) mass spectrometer (Thermo Electron, San Jose, Calif.) that was operated in a collisional-induced dissociation mode to obtain both MS and MS/MS spectra. Samples of tryptic peptides were loaded onto the microcapillary column and separated by applying a gradient from 5-80% acetonitrile in 0.5% acetic acid at a flow rate of 250 nL/min for 55 min. Mass spectrometry data were acquired in data-dependent acquisition mode, in which a full MS scan was followed by 10 MS/MS spectra of the 10 most abundant ions. Spectra were searched against the human International Protein Index (IPI) database using SEQUEST (Bioworks software package, version 3.3, Thermo Electron, San Jose, Calif.). GSK3β (Swiss-Prot entry P49841) was identified. The search parameters permitted ±1.0 Da peptide MS tolerance, and ±1.0 Da MS/MS tolerance. Phosphorylation (a +80 mass increase) was sought on serine (S), threonine (T), and tyrosine (Y) residues, together with allowance of oxidation of methionine and carboxymethylation of cysteines. Up to two missed tryptic cleavages of peptides were considered. The cutoff for SEQUEST assignment was a cross-correlation score (Xcorr) greater than 1.9, 2.5, and 3.8 for peptide charge states of 1, 2, and 3, respectively; and a delta-correlation score (ΔCn)>0.10. Manual identifications were also performed to define the exact location of phosphorylation sites based upon the b- and y-ions of the corresponding identifying MS/MS spectra.

Results and Discussion

Figure 1B:
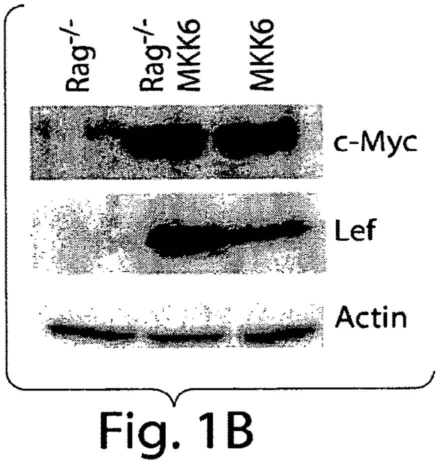
FIG. 1B is a Western blot showing c-Myc and Lef in thymocytes from $Rag^{-/-}$, MKK6 and $Rag^{-/-}$/MKK6 mice.
Figure 1C:
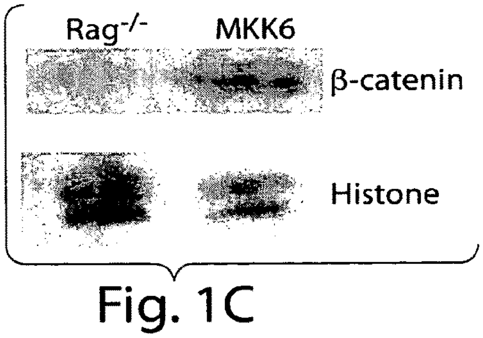
FIG. 1C is a Western blot showing β-catenin in nuclear extracts from $Rag^{-/-}$ and MKK6 thymocytes.
Figure 1D:
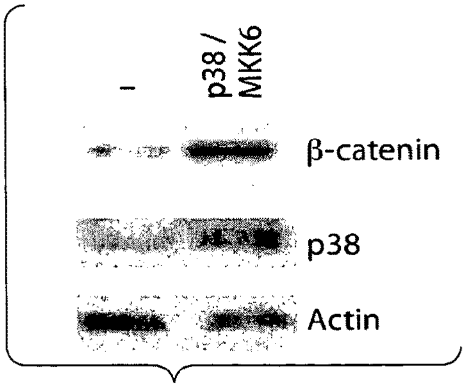
FIG. 1D is a Western blot showing β-catenin and p38 MAPK in whole cell extracts from 293T cells transfected with GSK3β (–) or GSK3β with p38 MAPK and MKK6 (p38/MKK6).
Figure 6:
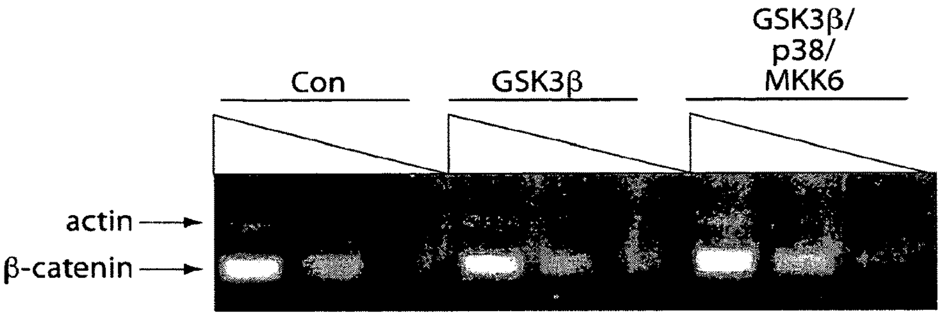
FIG. 6 presents a gel demonstrating through RT-PCR experiments that p38 MAPK does not affect β-catenin mRNA levels. The mRNA levels of β-catenin and actin in non-transfected control (Con) 293T cells and cells transiently transfected with expression constructs for GSK3β alone or in combination with p38 MAPK and MKK6 were examined by semi-quantitative RT-PCR. Three serial ½ dilutions of cDNA were used to examine β-catenin and actin expression.

The increased abundance of c-Myc and Lef proteins in the MKK6 transgenic thymocytes compared with Rag$^{-/-}$ thymocytes was confirmed by Western blot analysis (FIG. 1A). Thymocytes from Rag$^{-/-}$ crossed with MKK6 transgenic (Rag$^{-/-}$ MKK6) mice contained higher amounts of c-Myc and Lef proteins than did Rag$^{-/-}$ thymocytes, indicating that the activation of p38 MAPK, but not the pre-TCR signals, contribute to the enhanced expression of these transcription factors (FIG. 1B). The c-myc and lef genes are targets of the β-catenin signaling pathway in certain contests (12, 13). Nuclear accumulation of β-catenin was detected in MKK6 thymocytes, but not in $Rag^{-/-}$ thymocytes (FIG. 1C). Expression of constitutively active MKK6 in 293T cells was also sufficient to increase the amount of β-catenin protein (FIG. 1D), but had no effect on β-catenin mRNA (FIG. 6).

Figure 2A:
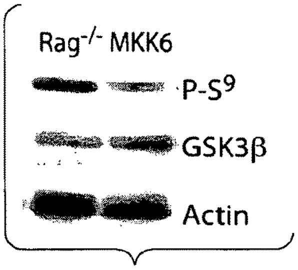
FIG. 2A is a Western blot showing phospho-$Ser^9$ GSK3β (P-$Ser^9$) and total GSK3β to $Rag^{-/-}$ and MKK6 thymocytes.
Figure 2B:
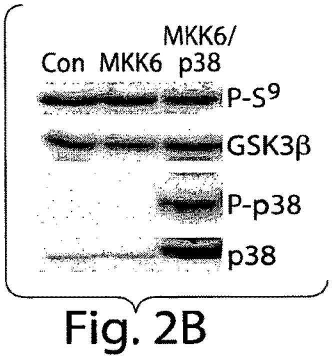
FIG. 2B is a Western blot showing P-$Ser^9$ GSK3β, GSK3β, phospho-p38 MAPK (P-p38) and p38 MAPK in 293T cells transfected with an empty vector (Con), MKK6 alone or MKK6 and p38 MAPK (MKK6/p38).
Figure 2C:
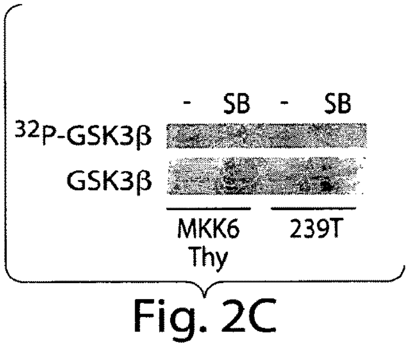
FIG. 2C is a Western blot showing results of an in vitro p38 MAP kinase assay with inactive recombinant GSK3β as the substrate, and p38 MAPK immunoprecipitated from MKK6-thymocytes (MKK6 Thy) or MKK6-transfected 293T cells (293T). In vitro reactions were incubated in the presence (SB) or absence (–) of the specific p38 MAPK inhibitor SB203580. Total GSK3β was visualized by PonceauS staining and phosphorylated GSK3β detected by autoradiography.
Figure 2D:
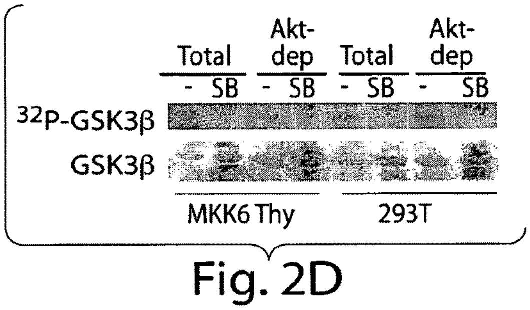
FIG. 2D is a Western blot showing results of an in vitro p38 MAPK kinase assay as described in FIG. 2C using total or Akt-depleted extracts (Akt-dep) from MKK6 thymocytes (MKK6 Thy) or MKK6-transfected 293T cells (293T).
Figure 2E:
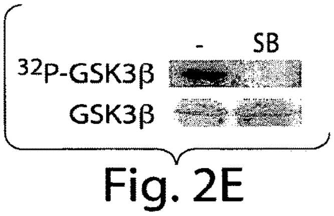
FIG. 2E is a Western blot showing results of an in vitro kinase assay as described in FIG. 2C with recombinant active p38 MAPK kinase.
Figure 2F:
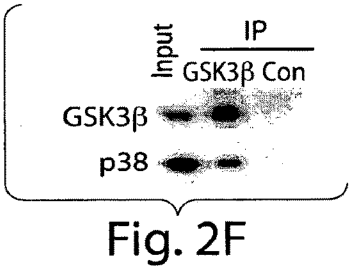
FIG. 2F is a Western blot showing GSK3β and p38 MAPK in the GSK3β and p21 (Con) immunoprecipitates (IP) and whole cell extracts from MKK6 thymocytes (Input).
Figure 2G:
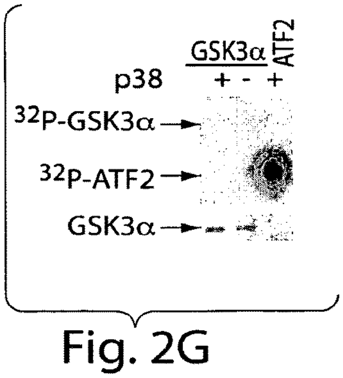
FIG. 2G is a Western blot showing results of an in vitro kinase assay for recombinant active p38 MAPK kinase using catalytically-inactive GSK3β as a substrate. Phosphorylation of ATF2 was examined as a positive control.
Figure 7:
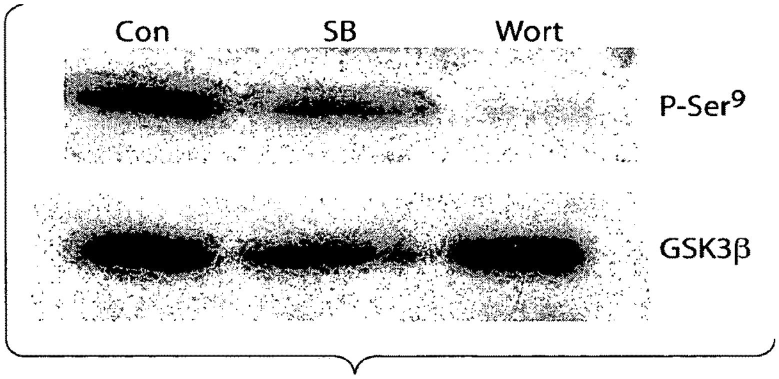
FIG. 7 presents a Western blot showing that p38 MAPK does not regulate AKT-mediated $Ser^9$ phosphorylation of GSK3β. 293T cells were treated with vehicle control (Con), SB203580 (SB) or Wortmanin (Wort) for 40 minutes. The levels of phosphoro-$Ser^9$ and GSK3β were determined by Western Blot analysis.
Figure 8:
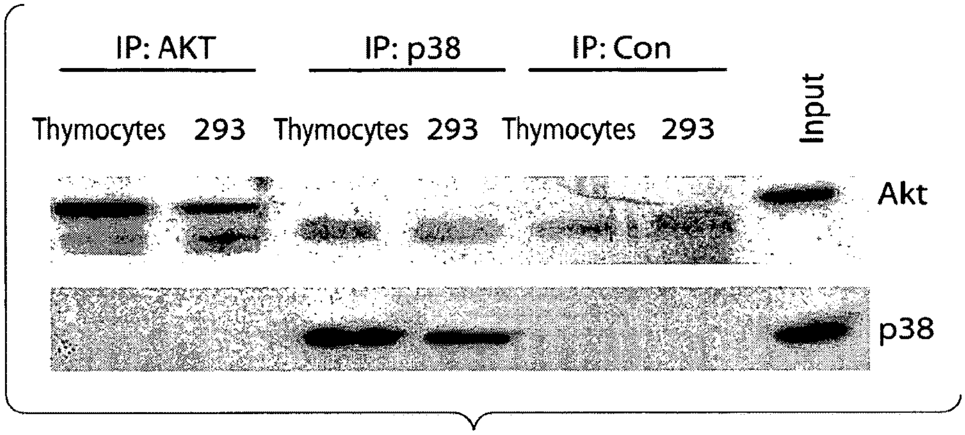
FIG. 8 presents a Western blot showing Akt and p38 levels. Akt and p38 MAPK were immunoprecipitated (IP) from whole cell extracts from MKK6 thymocytes (Thy) or MKK6-transfected 293T cells (293). Immunoprecipitation of p21 was included as a negative control (Con). Total cell lysate (Input) from MKK6 thymocytes and the immunoprecipitates were examined for Akt and p38 MAPK by Western blot analysis.
Figure 9:
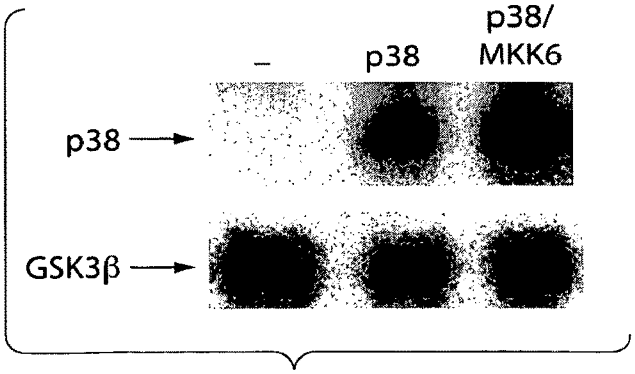
FIG. 9 presents a Western blot showing that p38 MAPK associates with GSK3β. GSK3β was immunoprecipated from whole cell lysates from 293T cells transiently transfected with expression constructs for GSK3β along (−), GSK3β and p38 MAPK (p38), or GSK3β, p38 MAPK and MKK6 (p38/MKK6). The levels of p38 and GSK3β in the immunoprecipitates were determined by Western blot analysis.

Phosphorylation of β-catenin by GSK3β targets β-catenin for ubiquitination and subsequent degradation (14, 15). The best characterised mechanism for the inactivation of GSK3β is through phosphorylation of its N-terminus at $Ser^9$ by Akt (16). No increase was observed in the amount of phospho-$Ser^9$ GSK3β in MKK6 thymocytes compared with that in $Rag^{-/-}$ thymocytes (FIG. 2A). Similarly, no increase in phospho-$Ser^9$ was observed in 293T cells transfected with constitutively active MKK6 (FIG. 2B). Phosphorylation of $Ser^9$ was impaired by Wortmanin, an inhibitor of the PI3K-Akt pathway, but it was not affected by the pharmacological inhibitor of p38 MAPK SB203580 (FIG. 7). Thus, p38 MAPK appears not to regulate the Akt-mediated phosphorylation of GSK3β on $Ser^9$. p38 MAPK immunoprecipitated from MKK6 thymocytes or MKK6-transfected 293T cells phosphorylated recombinant catalytically-inactive GSK3β in vitro and this phosphorylation was blocked by the p38 MAPK inhibitor (FIG. 2C). No Akt was detected in p38 MAPK immunoprecipitates and no p38 MAPK was detected in Akt immunoprecipitates (FIG. 8) ruling out the presence of residual AKT associated with p38 MAPK. Depletion of Akt before immunoprecipitating p38 MAPK, did not affect phosphorylation of GSK3β (FIG. 2D). A purified recombinant activated p38 MAPK also phosphorylated GSK3β in vitro and this phosphorylation was blocked by SB203580 (FIG. 2E). Co-immunoprecipitation analysis showed that p38 MAPK was present in GSK3β immunoprecipitates from MKK6 thymocytes (FIG. 2F) and 293T cells (FIG. 9). Thus, p38 MAPK physically associates with and phosphorylates GSK3β at a $Ser^9$-independent residue. Although GSK3α and GSK3β are thought to be similarly regulated and can compensate for each other for some functions (17, 18), GSK3α was not phosphorylated by recombinant p38 MAPK in vitro (FIG. 2G).

Figure 3A:
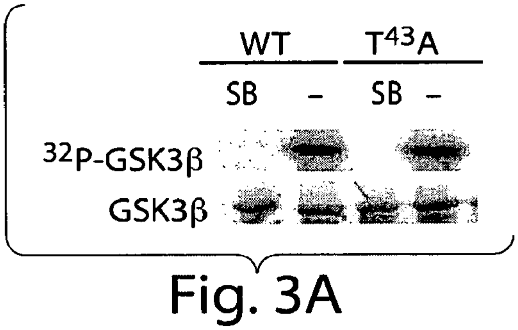
FIG. 3A is a Western blot showing results of an in vitro kinase assays for recombinant p38 MAPK using catalytically-inactive GSK3β and GSK3β-$T^{43}$A mutant as substrates.
Figure 3B:
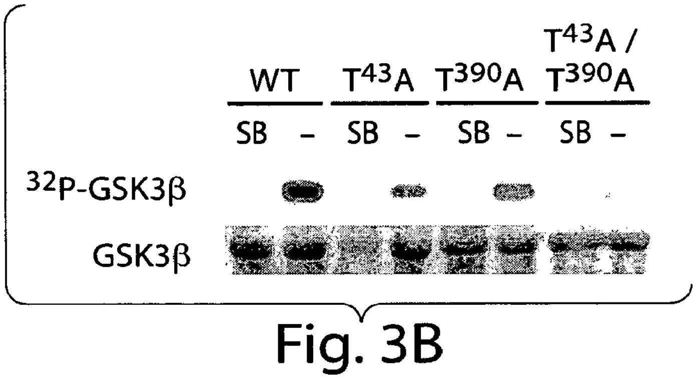
FIG. 3B is a Western blot showing results of an in vitro kinase assay for recombinant p38 MAPK using kinase-inactive GSK3β (WT) GSK3β-$T^{43}$A, GSK3β-$T^{390}$A and GSK3β-$T^{43}$A/$T^{390}$A mutants as substrates.
Figure 3C:
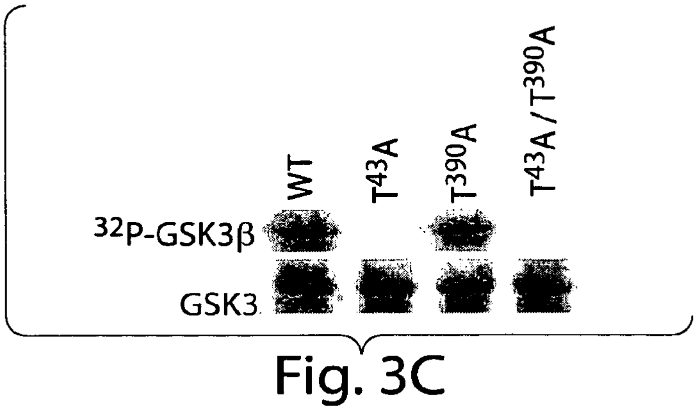
FIG. 3C is a Western blot showing results of an in vitro kinase assay for recombinant active ERK using catalytically-inactive GSK3β, GSK3β-$T^{43}$A, GSK3β-$T^{43}$A and GSK3β-$T^{43}$A/$T^{43}$A mutants as substrates.
Figure 10A:
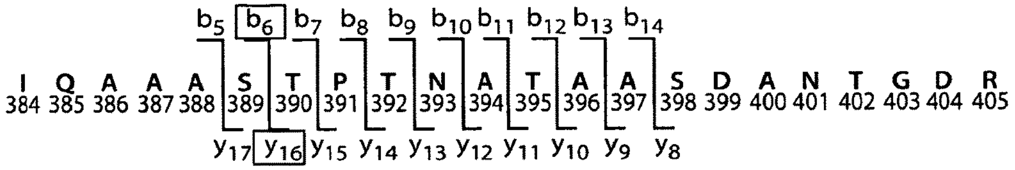
FIG. 10A-B show the b and y ion layout for the middle of the peptide. Phosphorylation of serine-389 ($S^{389}$) will produce a b6 ion that is 80 Da heavier, while phosphorylation of threonine-390 ($T^{390}$) will produce a y16 ion that is 80 Da heavier. These are the only ions that will differentiate the difference in phosphorylation of $S^{389}$ and $T^{390}$. All other b and y ions will be the same for both species. The b7, b8, y14, and y15 ions will differentiate between phosphorylation of $T^{390}$ and $T^{392}$ (or higher). Similar b and y ions can be used to differentiate phosphorylations of $T^{395}$, etc. The ions actually identified as b and y ions are indicated in the figure. There was no b6 ion present, but the y16 ion at m/z=1642.5 and the presence of the y15 ion at m/z=1461.6 defines that the phosphorylation site is at $T^{390}$ and not on any another serine or threonine.
Figure 10B:
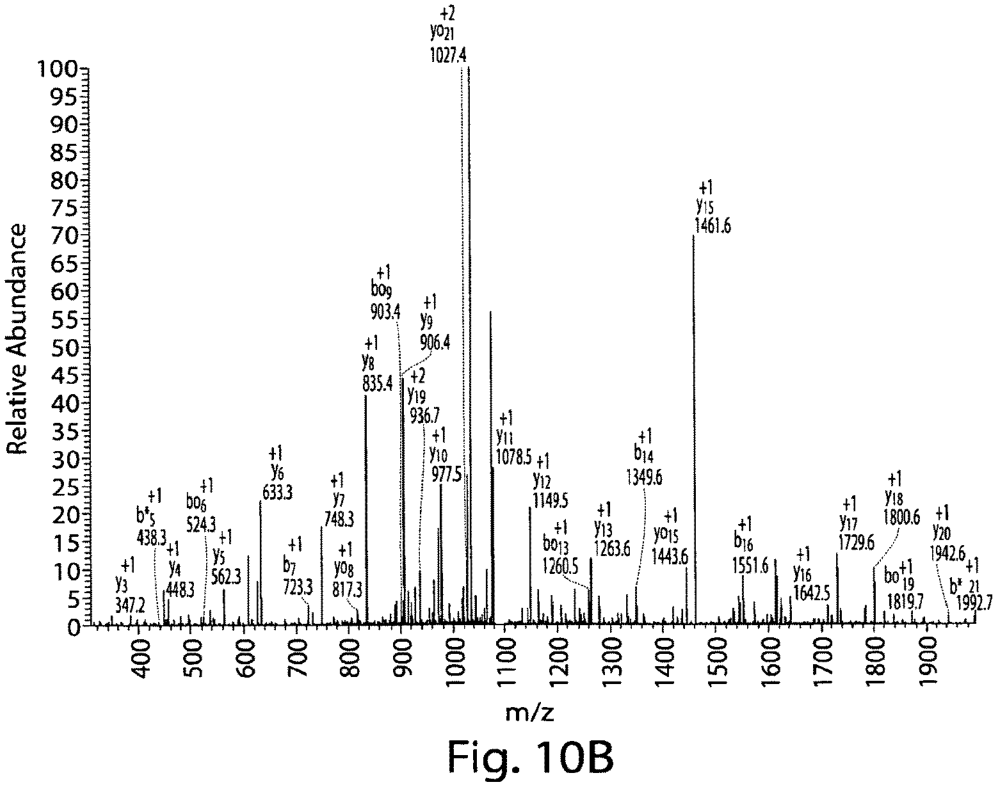
Figure 11A:
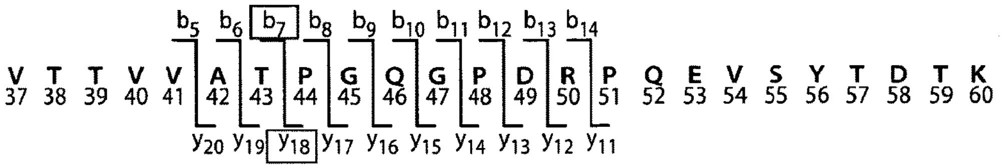
FIG. 11A-B present MS/MS spectra identifying a P-$Thr^{43}$Pro phosphopeptide VTTVVATPGQGPDRPQEVSTTDTK (SEQ ID NO:98) as a target for p38 MAPK as described in FIG. 10.
Figure 11B:
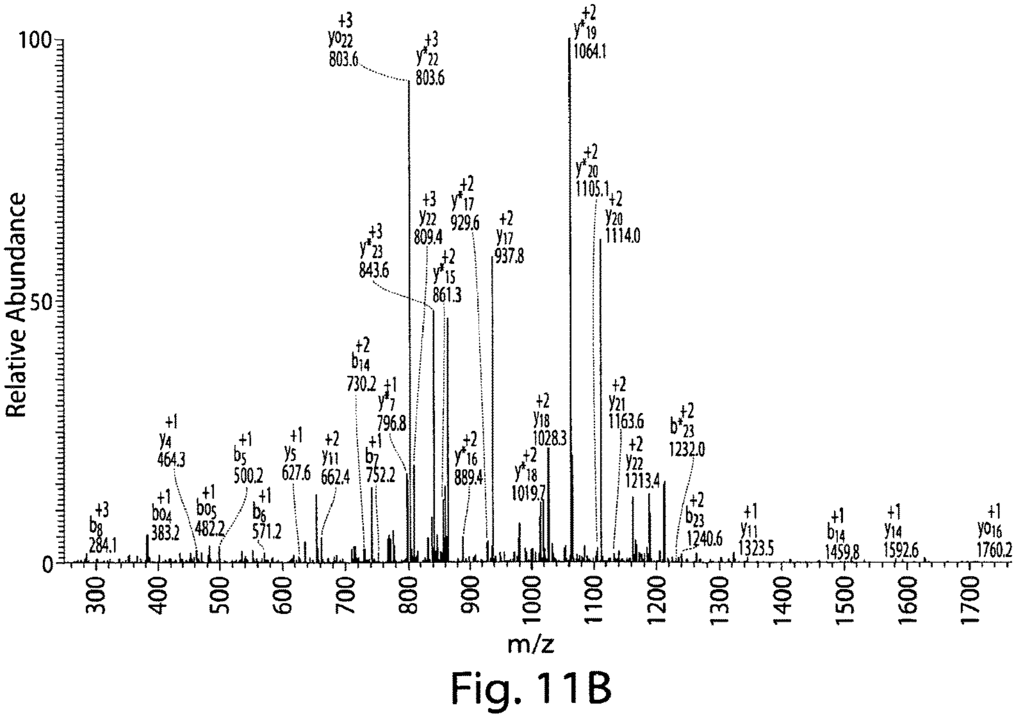

The MAPK extracellular signal regulated protein kinase (ERK) phosphorylates $Thr^{43}$ of GSK3β (19), but does not affect GSK3β activity. Although SerPro or ThrPro motifs recognized by ERK are also recognized by other MAPK groups, p38 MAPK was still able to partially phosphorylate a GSK3β-$T^{43}$A mutant (FIG. 3A), suggesting the existence of additional phosphorylation sites in GSK3β. Mass spectrometry analysis of recombinant GSK3β phosphorylated in vitro by p38 MAPK showed two GSK3β phosphopeptides containing phosphorylation within a consensus SerPro or ThrPro motif, a phospho-peptide containing $Thr^{43}$ and a C-terminal peptide (384-403) containing the $Thr^{390}$Pro motif (corresponding to $Ser^{389}$Pro in mouse GSK3β) (FIGS. 10 and 11). To confirm $Thr^{390}$ as a target of p38 MAPK in GSK3β, catalytically-inactive GSK3β-$T^{390}$A and GSK3β-$T^{43}$A/$T^{390}$A mutants were used as substrates for p38 MAPK in vitro. Phosphorylation of the GSK3β-$T^{390}$A mutant by p38 MAPK was partially reduced but not abrogated (FIG. 3B), but phosphorylation of the GSK3β-$T^{43}$A/$T^{390}$A mutant was abrogated, indicating that these two residues are likely the targets for p38 MAPK in GSK3β. The $T^{43}$A mutation but not the $T^{390}$A mutation abrogated phosphorylation of GSK3β by ERK (FIG. 3C). Thus, $Thr^{390}$ of GSK3β appears to be specifically phosphorylated by p38 MAPK.

Figure 3D:
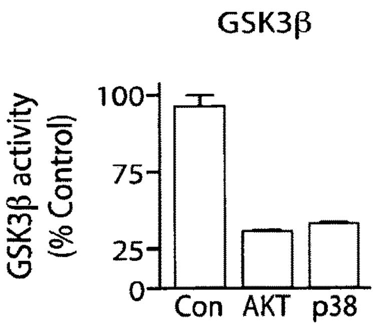
FIG. 3D-F present graphs showing results of an in vitro kinase assay for active GSK3β, GSK3β-$T^{43}$A and GSK3β-$T^{390}$A mutants before (Con) or after incubation with activated Akt or activated p38 MAPK. GSK3β activity relative to the activity without Akt or p38 MAPK (Con) is shown. Error bars represent SD (n=3).
Figure 3E:
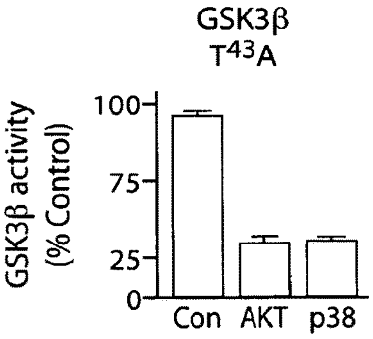
Figure 3F:
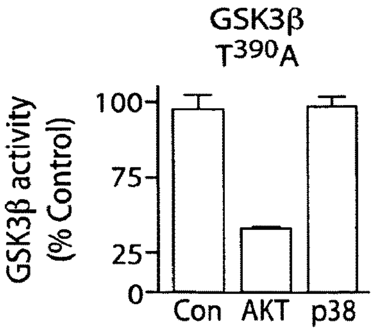
Figure 3G:
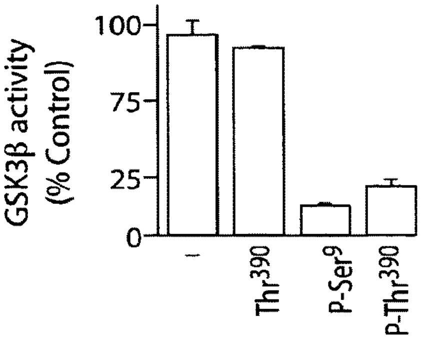
FIG. 3G is a graph showing results of in vitro GSK3β kinase reactions alone (–) or in the presence of unphosphorylated-$Thr^{390}$ ($Thr^{390}$), phospho-$Ser^9$ (P-$Ser^9$), or phospho-$Thr^{390}$ (P-$Thr^{390}$) peptides as described in FIG. 3D-F.
Figure 3H:
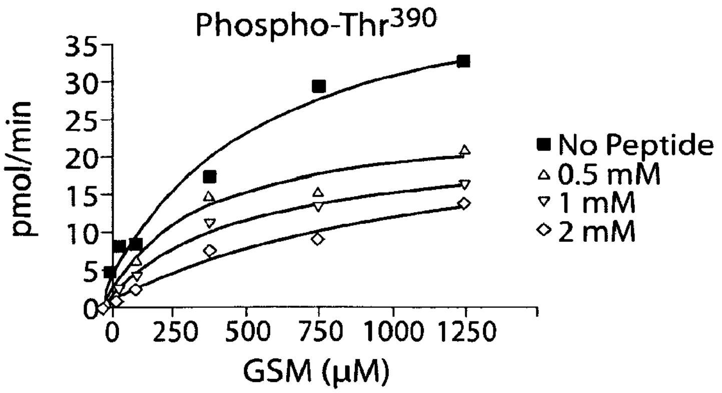
FIG. 3H-J present graphs showing results of GSK3β in vitro kinase assays as in FIG. 3D-F using various concentrations of phospho-$Thr^{390}$, phospho-$Ser^9$ and unphosphorylated-$Thr^{390}$ peptides. Each point is the average of two measurements.
Figure 3I:
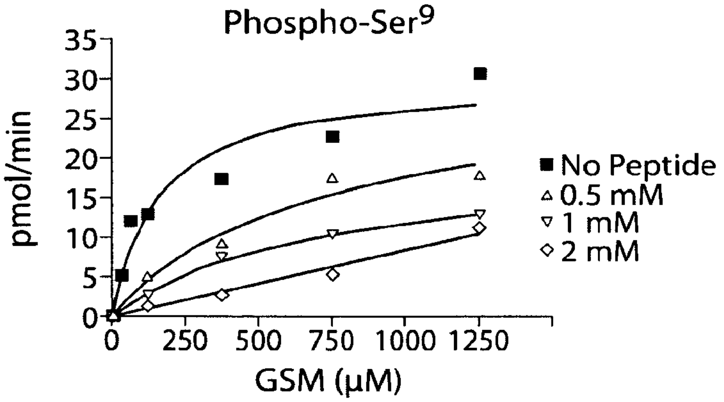
Figure 3J:
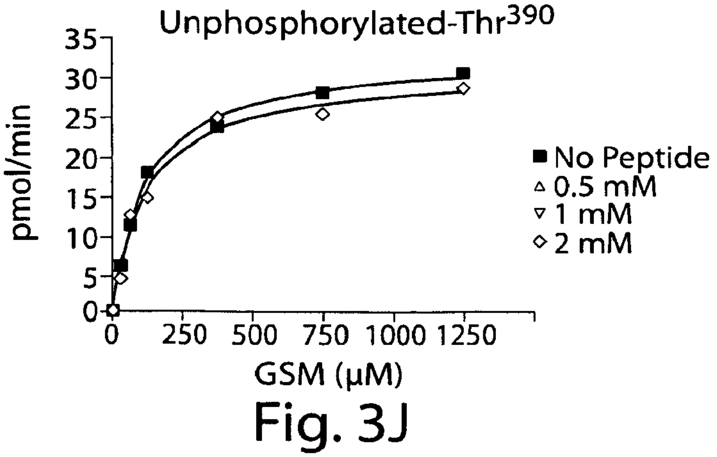
Figure 12:
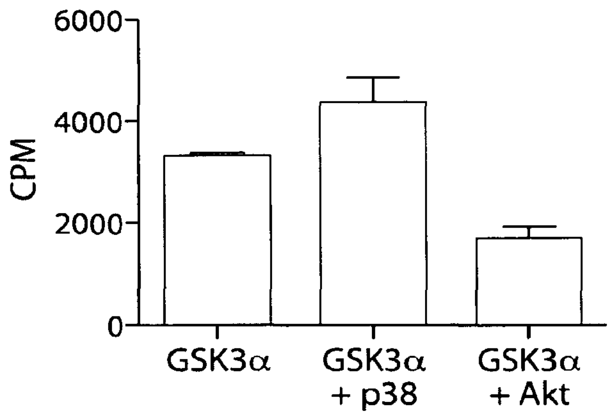
FIG. 12 presents a graph showing that p38 MAPK does not inhibit GSK3α activity in vitro. Recombinant kinase-active GSK3α was pre-incubated in the reaction buffer alone (GSKα), with activated p38 MAPK or activated Akt (15 min). In vitro GSK3α kinase assays were then performed using GSM as the substrate. Error bars represent SD (n=3).

The activity of wild-type GSK3β and GSK3β-$T^{43}$A and GSK3β-$T^{390}$A mutants, before or after incubation with p38 MAPK or Akt was examined. p38 MAPK inhibited both wild-type GSK3β and GSK3β-$T^{43}$A mutant (FIG. 3D-E), but not the GSK3β-$T^{390}$A mutant (FIG. 3F). Akt inhibited wild-type GSK3β and the two mutants (FIG. 3D-F). p38 MAPK did not affect the activity of GSK3α (FIG. 12) in which the $Thr^{390}$ residue from GSK3β is not conserved. Together, these results demonstrate that p38 MAPK-mediated phosphorylation of GSK3β at $Thr^{390}$ (but not $Thr^{43}$) is sufficient to inhibit GSK3β activity. A peptide derived from the N-terminus of GSK3β containing phospho-$Ser^9$ specifically inhibits GSK3β in vitro (20, 21). A phospho-$Thr^{390}$ peptide also inhibited GSK3β activity, while the unphosphorylated-$Thr^{390}$ peptide did not (FIG. 3G). The phospho-$Thr^{390}$ peptide inhibited GSK3β activity as efficiently as the phospho-$Ser^9$ peptide (FIG. 3H-J). Thus, phosphorylation at $Thr^{390}$ by p38 MAPK may cause an inhibition of GSK3β comparable to the phosphorylation of $Ser^9$ by Akt.

Figure 4A:
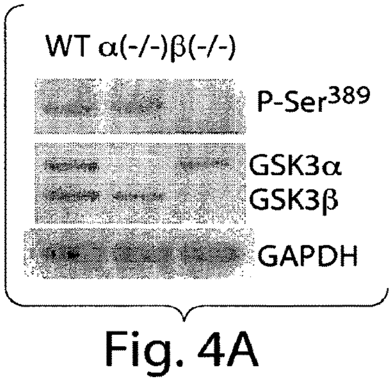
FIG. 4A is a Western blot showing the presence of endogenous phospho-$Ser^{389}$ GSK3β (P-$Ser^{389}$) in wild-type, GSK3$\alpha^{-/-}$ and GSK3$\beta^{-/-}$ ES cells. Total GSK3α, GSK3β and GAPDH were examined as controls.
Figure 4B:
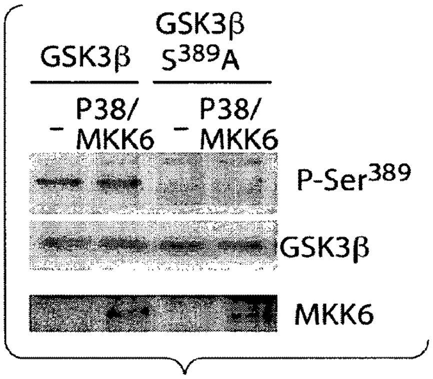
FIG. 4B is a Western blot showing P-$Ser^{389}$ in GSK3$\beta^{-/-}$ ES cells transfected with wild-type GSK3β or GSK3β-$S^{389}$A mutant alone or with p38 MAPK and MKK6 (p38/MKK6).
Figure 4C:
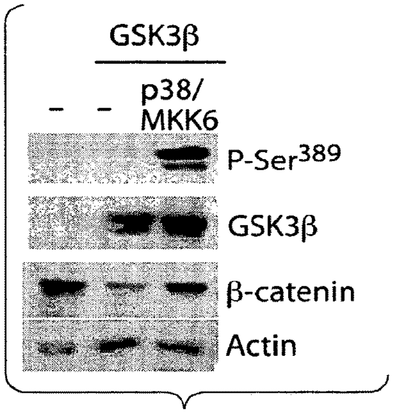
FIG. 4C is a Western blot showing P-$Ser^{389}$, Flag-tagged mouse GSK3β and β-catenin in non-transfected 293T cells (–) or cells transfected with mouse GSK3β alone or in combination with p38 MAPK and MKK6 (p38/MKK6).
Figure 13:
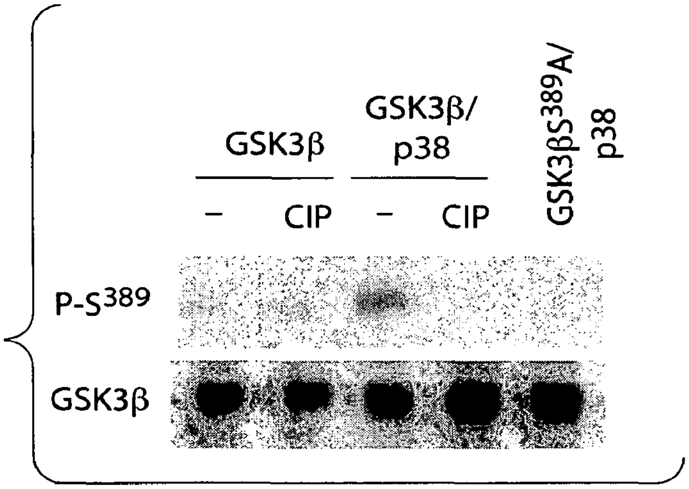
FIG. 13 is a Western blot showing that the phospho-$S^{389}$ Ab specifically recognized GSK3β phosphorylated at $S^{389}$ by p38 MAPK. Recombinant mouse wildtype GSK3β was incubated with or without recombinant active p38 MAPK for 15 min, followed by an incubation with or without (−) Calf Intestinal Phosphatase (CIP). Recombinant GSK3β-$S^{389}$A mutant was also incubated with active p38 MAPK as described for wildtype GSK3β, but not treated with CIP. The presence of phospho-$S^{389}$ was determined by Western blot analysis using the anti-phosphro-$S^{389}$ AB. Blots were reprobed for total GSK3β.

To demonstrate the phosphorylation of this residue in intact cells and in vivo, an antibody (Ab) specific to a mouse phospho-$Ser^{389}$ GSK3β peptide was generated. A band corresponding to GSK3β was detected with this Ab in wild-type and $GSK3\alpha^{-/-}$ embryonic stem (ES) cells, but not in the $GSK3\beta^{-/-}$ES cells by Western blot analysis (FIG. 4A). This specific band was also present in $GSK3\beta^{-/-}$ ES cells transacted with a wild-type GSK3β, but not with a GSK3β-$S^{389}$A mutant (FIG. 4B). Phospho-$Ser^{389}$ GSK3β was detected in mouse GSK3β-transfected 293T cells, but only if active MKK6 was present (FIG. 4C). The presence of the phospho-$Ser^{389}$ GSK3β in these cells correlated with an increased amount of β-catenin (FIG. 4C), indicative of an inhibition of GSK3β activity. $Ser^{389}$-phosphorylation was also detected in wild-type GSK3β, but not the GSK3β-$S^{389}$A mutant after in vitro incubation with activated p38 MAPK (FIG. 13). Phosphatase treatment of GSK3β previously incubated with activated p38 MAPK abrogated its recognition by the phospho-$Ser^{389}$ Ab (FIG. 13). Together, these results show the specificity of this Ab for phospho-$S^{389}$ GSK3β, and the phosphorylation of GSK3β as $S^{389}$ by p38 MAPK in vitro.

Figure 4D:
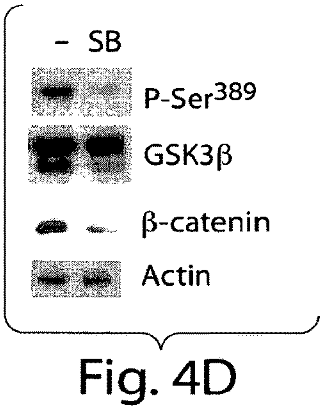
FIG. 4D is a Western bios showing P-$Ser^{389}$, total GSK3β and β-catenin in 293T cells transfected with GSK3β, p38 and MKK6 in the absence (–) or presence of SB203580.
Figure 4E:
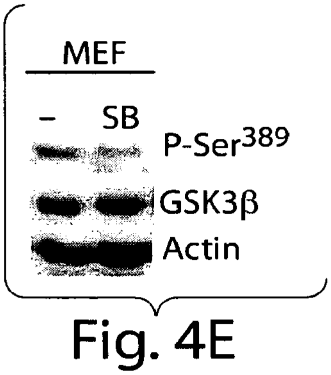
FIG. 4E-F present Western blots showing P-$Ser^{389}$ and total GSK3β in MEF or total GSK3α and GSK3β in ES cells non-treated (–) or treated with SB203580.
Figure 4F:
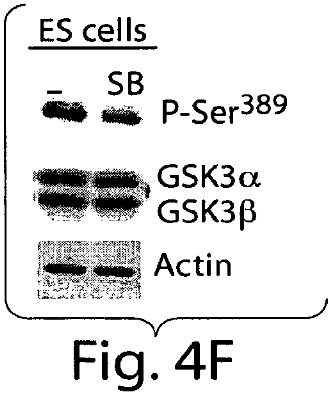
Figure 4G:
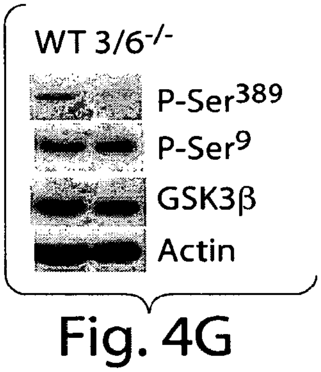
FIG. 4G-I present Western blots showing P-$Ser^{389}$, P-$Ser^9$, total GSK3β, P-p38, total p38 and β-catenin in WT and $MKK3^{-/-}MKK6^{-/-}$ ($3/6^{-/-}$) MEF.
Figure 4H:
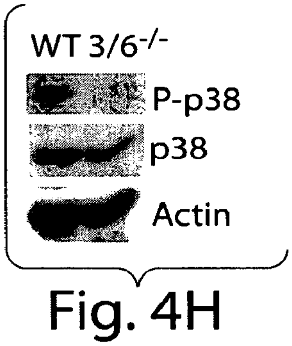
Figure 4I:
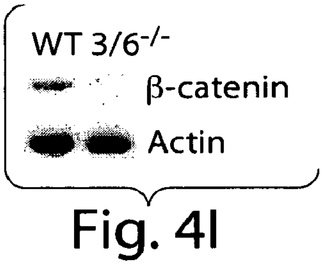

To determine whether activation of p38 MAPK was required for phosphorylation of GSK3β at $Ser^{389}$ in intact cells mouse GSKβ-transfected 293T cells were treated with SB203580. Inhibition of p38 MAPK abrogated the phosphorylation of $Ser^{389}$ (FIG. 4D). Similarly, treatment with SB203580 inhibited phosphorylation of endogenous GSK3β at $Ser^{389}$ in wild-type mouse embryonic fibroblasts (MEFs) and embryonic stem (ES) cells (FIG. 4E-F). The abundance of phospho-$Ser^{389}$ in MEFs deficient for the major upstream activators of p38 MAPK, MKK3 and MKK6 was also examined (22). Phospho-$Ser^{389}$ was barely detectable in $MKK3^{-/-}MKK6^{-/-}$ MEFs (FIG. 4G). In contrast, the amounts of phospho-$Ser^9$ were comparable in wildtype and $MKK3^{-/-}MKK6^{-/-}$ MEFs (FIG. 4G). Thus, activation of p38 MAPK appears to be required for phosphorylation of GSK3β at $Ser^{389}$. Inhibition of p38 MAPK either by SB203580 (FIG. 4D) or by the absence of MKK3 and MKK6 (FIG. 4I) also decreased the amount of β-catenin, consistent with the possibility that p38 MAPK activation is required for repressing GSK3β activity.

Figure 4J:
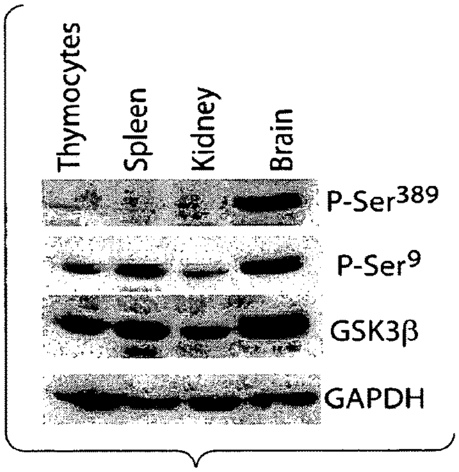
FIG. 4J presents a Western blot showing the tissue distribution of P-$Ser^{389}$, P-$Ser^9$ and total GSK3β.
Figure 4K:
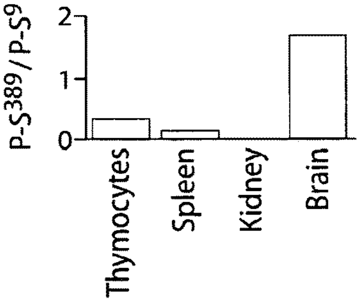
FIG. 4K presents a graph showing quantification of the levels of P-$Ser^{389}$ relative to P-$Ser^9$ in each tissue.
Figure 4L:
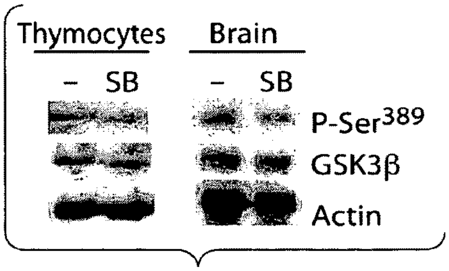
FIG. 4L presents Western blots showing P-$Ser^{389}$ and total GSK3β in thymocytes and brain from WT mice treated in vivo with vehicle (–) or SB203580 (SB).
Figure 4M:
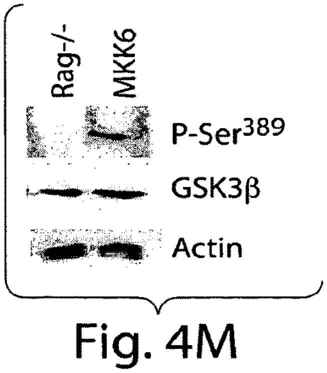
FIG. 4M is a Western blot showing P-$S^{389}$ and total GSK3β in thymocytes from $Rag^{-/-}$ and MKK6 transgenic mice.
Figure 14:
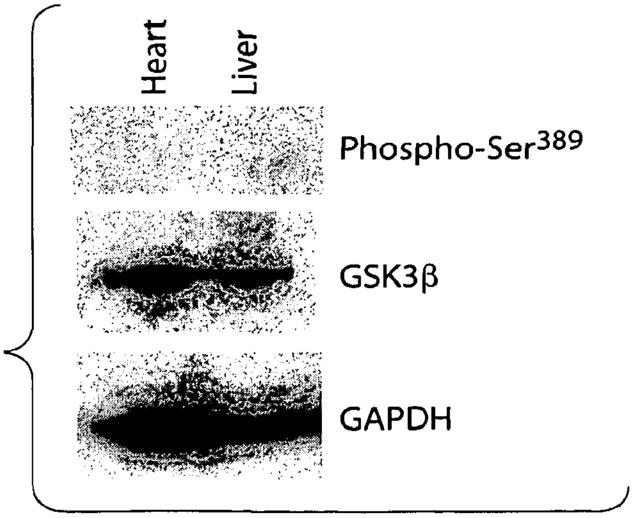
FIG. 14 is a Western blot showing phospho-$Ser^{389}$ GSK3β and total GSK3β in whole-cell lysates from mouse heart and liver. GAPDH was examined as a loading control.
Figure 15A:
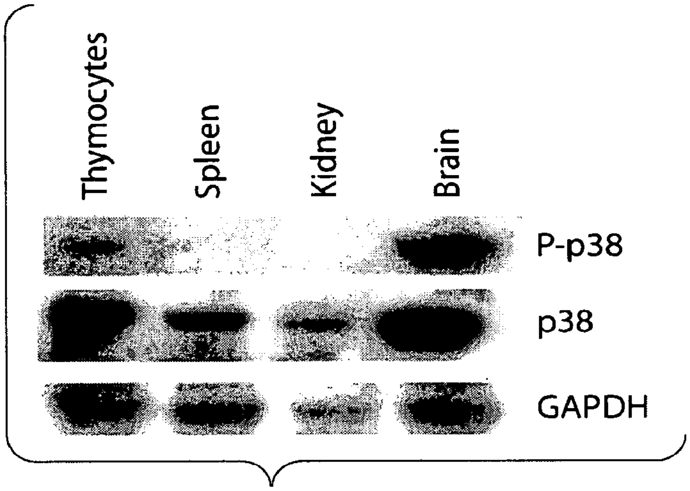
FIG. 15A presents a Western blot showing phospho-p38 (P-p38) and total p38 levels in whole cell extracts for thymocytes (Thy), splenocytes (Spl), kidney and brain. The level of GAPDH was examined as a loading control.
Figure 15B:
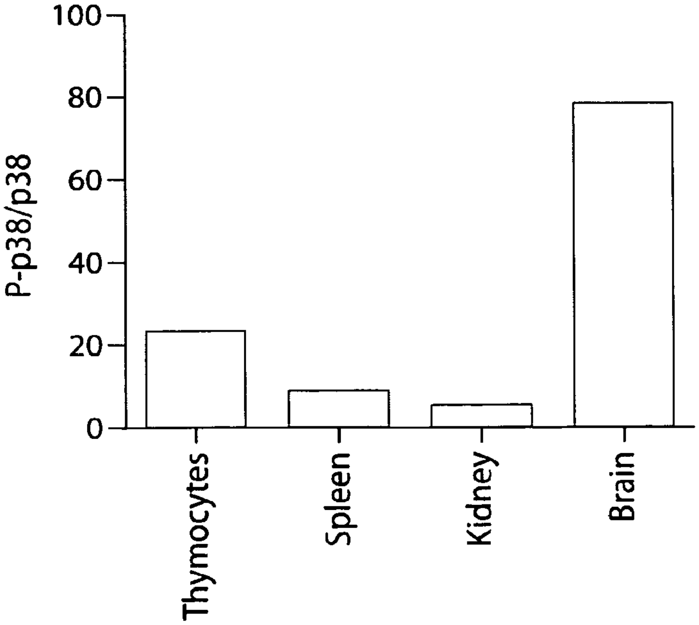
FIG. 15B presents a graph showing the ratio of phospho-p38 to total p38.

Phospho-$Ser^{389}$ was also examined in different mouse tissues. A high amount of phospho-$S^{389}$ was detected in brain and lesser amounts where detected in thymocytes and spleen cells (FIG. 4J-K). Phospho-$Ser^{389}$ was not detected in kidney (FIG. 4J-K), liver or heart (FIG. 14). Phosphorylation of GSK3β at $Ser^9$ was detected in practically all examined tissues (FIG. 4J-K). Analysis of the relative abundance of phospho-$S^{389}$ and phospho-$S^{9}$ showed a predominance of the former in brain and thymocytes (FIG. 4J-K), which correlated with the selective high activation of p38 MAPK in these tissues (FIG. 15). Inhibition of p38 MAPK by treating animals with SB203580 reduced the levels of phospho-$Ser^{389}$ GSK3β in both thymocytes and brain (FIG. 4L). Analysis of phospho-$Ser^{389}$ in MKK6 and $Rag^{-/-}$ thymocytes showed phospho-$S^{389}$ GSK3β was present selectively in MKK6 thymocytes (FIG. 4M). Together, there results support the proposal that GSK3β is phosphorylated at $S^{389}$ in vivo by p38 MAPK and that this alternative regulatory mechanism of GSK3β is tissue specific.

To date phosphorylation at $Ser^{9}$ by Akt is the best characterised mechanism for the inhibition of GSK3β activity. However, knockin mice where $Ser^{9}$ was replaced by Ala have only a subtle defect related to insulin regulation of glycogen synthase in skeletal muscle (23), indicating that alternative mechanisms may be involved in the negative regulation of GSK3β for certain functions. Herein it is proposed that phosphorylation of GSK3β at $S^{389}$ by p38 MAPK may be one such mechanism. Conditions that promote the activation of p38 MAPK promote the accumulation of β-catenin in certain scenarios, thus activation of the p38 MAPK pathway could be an alternative mechanism to regulate β-catenin/TCF signaling (and potentially, cell survival) through inactivation of GSK3β.

REFERENCES FOR EXAMPLE 1

1. T. Zarubin, J. Han, Cell Res 15, 11 (2005).
2. A. Mikhallov, M. Shinohara, C. L. Rieder, Cell Cycle 4, 57 (2005).
3. Q. B. She, N. Chen, Z. Dong, J Biol Chem 275, 20444 (2000).
4. T. Kurosu et al., Apoptosis 10, 1111 (2005).
5. H. C. Reinhardt, A. S. Aslanian, J. A. Lees, M. B. Yaffe, Cancer Cell 11, 175 (2007).
6. N. I. Dmitrieva, D. V. Bulavin, A. J. Fornace, Jr., M. B. Burg, Proc Natl Acad Sci USA 99, 194 (2002).
7. N. L. Diehl et al., J Exp Med 191, 321 (2000).
8. G. Pedraza-Alva et al., Embo J 25, 763 (2006).
9. V. Ioannidis, F. Beermann, H. Clevers, W. Held, Nat Immunol 2, 691 (2001).
10. F. Gounari et al., Nat Immunol 2, 863 (2001).
11. B. Hoffman, A. Amanullah, M. Shafarenko, D. A. Liebermann, Oncogene 21, 3414 (2002).
12. T. C. He et al., Science 281, 1509 (1998).
13. M. Filali, N. Cheng, D. Abbott, V. Leontiev, J. F. Engelhardt, J Biol Chem 277, 33398 (2002).
14. C. Liu et al., Cell 108, 837 (2002).
15. S. Salahshor, J. R. Woodgett, J Clin Pathol 58, 225 (2005).
16. D. A. Cross, D. R. Alessi, P. Cohen. M. Andjelkovich, B. A. Hemmings, Nature 378, 785 (1995).
17. B. W. Doble, S. Patel, G. A. Wood, L. K. Kockeritz, J. R. Woodgett, Dev Cell 12, 957 (2007).
18. B. W. Doble, J. R. Woodgett, J Cell Sci 116, 1175 (2003).
19. Q. Ding et al., Mol Cell 19, 159 (2005).
20. R. Dajani et al., Cell 105, 721 (2001).
21. S. Frame, P. Cohen, Biochem J 359, 1 (2001).
22. D. Brancho et al., Genes Dev. 17, 1969 (2003).
23. E. J. McManus et al., Embo J 24, 1571 (2005).
24. J. Raingeaud, A. J. Whitmarsh, T. Barrett, B. Derijard, R. J. Davis, Mol Cell Biol 16, 1247 (March 1996).
25. B. Derijard et al., Cell 76, 1025 (Mar. 25, 1994).
26. M. Rincon, B. Derijard, C. W. Chow, R. J. Davis, R. A. Flavell, Genes Funct 1, 51 (February 1997).
27. E. Schreiber, P. Matthias, M. M. Muller, W. Schaffner, Nucleic Acids Res 17, 6419 (Aug. 11, 1989).
28. N. Farley et al., Mol Cell Biol 26, 2118 (March 2006).
29. S. Kosuga et al., J Biol Chem 280, 42715 (Dec. 30, 2005).

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

The invention claimed is:

1. A method of reducing activity of GSK3β in a cell, the method comprising:

contacting a cell with a composition comprising an isolated GSK3β polypeptide and a carrier, wherein the polypeptide is a full-length GSK3β protein or a fragment of a full-length GSK3β protein and comprises a phosphorylated residue that corresponds to residue Thr390 in a full-length, wild-type, human GSK3β amino acid sequence, or corresponds to residue Ser389 in a full-length, wild-type, mouse GSK3β amino acid sequence, wherein the contacting results in the isolated GSK3β polypeptide in the cell and reduces GSK3β activity in the cell.

2. The method of claim 1, wherein the GSK3β polypeptide is a human GSK3β polypeptide and the phosphorylated residue corresponds to the Thr390 residue.

3. The method of claim 2, wherein the GSK3β polypeptide comprises the amino acid sequence set forth as: RIQAAAST($PO_3H_2$)PTN (SEQ ID NO:7).

4. The method of claim 1, wherein the GSK3β polypeptide is a mouse GSK3β polypeptide and the phosphorylated residue corresponds to the Ser389 residue.

5. The method of claim 4, wherein the GSK3β polypeptide comprises the amino acid sequence set forth as ARIQAAAS($PO_3H_2$)PPANATA (SEQ ID NO:87).

6. The method of claim 1, further comprising contacting the cell with a composition comprising a compound that results in the phosphorylation of a GSK3β residue that corresponds to residue Thr390 in a full-length, wild-type, human GSK3β amino acid sequence, or corresponds to the residue Ser389 in a full-length, wild-type, mouse GSK3β amino acid sequence.

* * * * *